(12) United States Patent
Lee et al.

(10) Patent No.: US 11,371,068 B2
(45) Date of Patent: Jun. 28, 2022

(54) EXTRACELLULAR HEME PRODUCTION METHOD USING METABOLICALLY ENGINEERED MICROORGANISM

(71) Applicant: KOREA ADVANCED INSTITUTE OF SCIENCE AND TECHNOLOGY, Daejeon (KR)

(72) Inventors: Sang Yup Lee, Daejeon (KR); Xin Rui Zhao, Daejeon (KR); Kyeong Rok Choi, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 250 days.

(21) Appl. No.: 16/483,430

(22) PCT Filed: Dec. 12, 2018

(86) PCT No.: PCT/KR2018/015748
§ 371 (c)(1),
(2) Date: Aug. 5, 2019

(87) PCT Pub. No.: WO2019/117612
PCT Pub. Date: Jun. 20, 2019

(65) Prior Publication Data
US 2019/0382817 A1 Dec. 19, 2019

(30) Foreign Application Priority Data

Dec. 12, 2017 (KR) .................. 10-2017-0170185
Dec. 10, 2018 (KR) .................. 10-2018-0158452

(51) Int. Cl.
| | |
|---|---|
| C12N 1/22 | (2006.01) |
| C12P 17/18 | (2006.01) |
| C12N 9/02 | (2006.01) |
| C12N 9/10 | (2006.01) |
| C12N 9/88 | (2006.01) |
| C12N 9/90 | (2006.01) |
| C12N 9/00 | (2006.01) |
| C12N 15/67 | (2006.01) |
| C12P 13/00 | (2006.01) |

(52) U.S. Cl.
CPC ............ *C12P 17/182* (2013.01); *C12N 9/001* (2013.01); *C12N 9/0008* (2013.01); *C12N 9/1085* (2013.01); *C12N 9/88* (2013.01); *C12N 9/90* (2013.01); *C12N 9/93* (2013.01); *C12N 15/67* (2013.01); *C12P 13/005* (2013.01); *C12Y 102/0107* (2013.01); *C12Y 103/03* (2013.01); *C12Y 103/03004* (2013.01); *C12Y 205/01061* (2013.01); *C12Y 401/01037* (2013.01); *C12Y 402/01024* (2013.01); *C12Y 402/01075* (2013.01); *C12Y 499/01001* (2013.01); *C12Y 504/03008* (2013.01); *C12Y 603/05007* (2013.01)

(58) Field of Classification Search
None
See application file for complete search history.

(56) References Cited

U.S. PATENT DOCUMENTS

| | | |
|---|---|---|
| 5,681,725 A | 10/1997 | Jensen |
| 2016/0340411 A1 | 11/2016 | Fraser et al. |

FOREIGN PATENT DOCUMENTS

| | | |
|---|---|---|
| KR | 1020080061801 A | 7/2008 |
| KR | 1020110070977 A | 7/2011 |
| KR | 1020140107025 A | 8/2014 |
| KR | 1020180127239 A | 11/2018 |
| KR | 1020180127239 A | 11/2020 |
| WO | 9319195 A1 | 9/1993 |

OTHER PUBLICATIONS

Choby et al. (J. Mol. Biol., vol. 428, No. 17, 2016, p. 3408-3428).*
Choby et al. (J. Mol. Biol., 2016, vol. 428 (17), pp. 3408-3428).*
Anzaldi, L., et al., "Overcoming the Heme Paradox: Heme Toxicity and Tolerance in Bactrial Pathogens", "Infection and Immunity", Dec. 2010, pp. 4977-4989, vol. 78, No. 12, Publisher: American Society for Microbiology.
Bu, W., et al., "Simultaneous determination of six urinary porphyrins using liquid chromatography-tandem mass spectrometry", "Journal of Chromatography B", 2003, pp. 411-423, vol. 783, Publisher: Elsevier.
Dailey, H., et al., "The *Escherichia coli* Protein YfeX Functions as a Porphyrinogen Oxidase, Not a Heme Dechelatase", "mBio", 2011, pp. e00248-11, 1-8, vol. 2, No. 6, Publisher: mbio.asm.org.
Datsenko, K., et al., "One-step inactivation of chromosomal genes in *Escherichia coli* K-12 using PCR products", "PNAS", 2000, pp. 6640-6645, vol. 97, No. 12.
Ding, W., et al., "5-Aminolevulinic acid production from inexpensive glucose by engineering the C4 pathway in *Escherichia coli*", "J. Ind Microbiol Biotechnol", Apr. 5, 2017, pp. 1127-1135, vol. 44, Publisher: Society for Industrial Microbiology and Biotechnology.
Feissner, C., et al., "ABC transportr-mediated release of a haem chaperone allows cytochrome c biogenesis", "Molecular Microbiology", 2006, pp. 219-231, vol. 61, No. 1, Publisher: Blackwell Publishing Ltd.

(Continued)

*Primary Examiner* — Hope A Robinson
(74) *Attorney, Agent, or Firm* — Hultquist, PLLC; Steven J. Hultquist

(57) ABSTRACT

The present invention relates to a microorganism variant having the ability to extracellularly produce heme, and more particularly to a metabolically engineered microorganism variant having the ability to extracellularly produce heme and a method of producing heme using the same. According to the present invention, heme, an organometallic compound which is increasingly used as a health food or food supplement for the treatment of *porphyria*, can be extracellularly secreted and produced in high yield using the microorganism variant, but not conventional chemical synthesis or enzymatic synthesis.

12 Claims, 8 Drawing Sheets
(8 of 8 Drawing Sheet(s) Filed in Color)
Specification includes a Sequence Listing.

(56) References Cited

OTHER PUBLICATIONS

Kang, Z., et al., "Recent advances in production of 5-aminolevulinic acid using biological strategies", "World J. Microbiol Biotechnol", 2017, Page(s) DOI 10.1007/s11274-2366-7, vol. 33, No. 200, Publisher: CrossMark.

Kim, J.M., et al., "Development of a markerless gene knock-out system for Mannheimia succiniciproducens using a temperature-sensitive plasmid", "FEMS Microbiol. Lett", 2008, pp. 78-85, vol. 278, Publisher: FEMS.

Kwon, S.J., et al., "High-Level Production of Porphyrins in Metabolically Engineered *Escherichia coli*: Systematic Extension of a Pathway Assembled from Overexpressed Genes Invlved in Heme Biosynthesis", "Applied and Environmental Microbiology", 2003, pp. 4875-4883, vol. 69, No. 8, Publisher: American Society for Microbiology.

Kwon, O.H., et al., "Potential Application of the Recombinant *Escherichia coli*-Synthesized Heme as a Bioavailable Iron Source", "Journal of Microbiology and Biotechnology", 2009, pp. 604-609, vol. 19, No. 6, Publisher: The Korean Society for Microbiology and Biotechnology.

Layer, G., et al., "Structure and function of ensymes in heme biosynthesis", "Protein Science 2010", 2010, pp. 1137-1161, vol. 19, Publisher: Wiley-Blackwell.

Lee, M.J., et al., "Porphrin Derivatives from a Recombinant *Escherichia coli* Grown on Chemically Defined Medium", "Journal of Microbiology and Biotechnology", 2012, pp. 1653-1658, vol. 22, No. 12, Publisher: The Korean Society for Microbiology and Biotechnology.

Lee, M.J., et al., "Effect of Gene Amplifications in Porphyrin Pathway on Heme Biosynthesis in a Recombinant *Escherichia coli*", "Journal of Microbiology and Biotechnology", 2013, pp. 668-673, vol. 23, No. 5, Publisher: The Korean Society for Microbiology and Biotechnology.

Letoffe, S., et al., "Bacteria capture iron from heme by keeping tetrapyrrol skeleton intact", "PNAS", 2009, pp. 11719-11724, vol. 106, No. 28.

Li, F., et al., "Constitutive expression of RyhB regulates the heme biosynthesis pathway and increases the 5-aminolevulnic acid accumulation in *Escherichia coli*", "FEMS Microbiol Lett", 2014, pp. 209-215, vol. 350, Publisher: FEMS.

Pranawidjaja, S., et al., "Analysis of Heme Biosynthetic Pathways in a Recombinant *Escherichia coli*", "J. Microbiol. Biotechnol.", Jun. 2015, pp. 880-886, vol. 25, No. 6, Publisher: The Korean Society for Microbiology and Biotechnology.

Schulz, H., et al., "Heme transfer to the heme chaperone CcmE during cytochrome c maturation requires CcmC protein, which may function independently of the ABC-transporter CcmAB", "Proc. Natl. Acad. Sci. USA", May 1999, pp. 6462-6467, vol. 96, Publisher: PNAS.

Studier, F.W., et al., "Use of Bacteriophage T7 RNA Polymerase to Direct Selective High-level Expression of Cloned Genes", "J. Mol. Biol.", 1986, pp. 113-130, vol. 189, Publisher: 1986 Academic Press Inc.

Turlin, E., et al., "Protoporphyrin (PPIX) efflux by the MacAB-TolC pump in *Escherichia coli*", "MicrobiologyOpen", 2014, pp. 849-859, vol. 3, No. 6, Publisher: John Wiley & Son Ltd.

Vuoristo, K., et al., "Metabolic engineering of the mixed-acid fermentation pathway of *Escherichia coli* for anaerobic production of glutamate and itaconate", "AMB Express", 2015, Page(s) DOI 10.1186/s13568-015-0147-y, vol. 5, No. 61, Publisher: Springer.

Wild, J., et al., "Targeting and retrofitting pre-existing libraries of transposon insertions with FRT and oriV elements for in-vivo generation of large quantities of any genomic fragement", "GENE", 1998, pp. 55-66, vol. 223, Publisher: Elsevier.

Zhang, J., et al., "Optimization of the heme biosynthesis pathway for the production of 5-aminolevulinic acid in *Escherichia coli*", "Scientific Reports", Feb. 2015, pp. 1-7, vol. 5, No. 8584.

Zhang, X.R., et al., "Metabolic engineering of *Escherichia coli* for secretory production of free haem", "Nature Catalysis", Aug. 2018, pp. 720-728, vol. 1, Publisher: www.nature.com/natacatal.

Mourer, T., et al., "Heme Assimilation in Schizosaccharomyces pombe Requires Cell-surface-anchored Protein Shu1 and Vacuolar Transporter Abc3", "Journal of Biological Chemistry", 2017, pp. 4898-4912, vol. 292, Publisher: www.jbc.org.

\* cited by examiner (a) 24°C (b) 30°C (c) 37°C

EXTRACELLULAR HEME PRODUCTION METHOD USING METABOLICALLY ENGINEERED MICROORGANISM

CROSS-REFERENCE TO RELATED APPLICATIONS

This application is a U.S. national phase under the provisions of 35 U.S.C. § 371 of International Patent Application No. PCT/KR18/15748 filed Dec. 12, 2018, which in turn claims priority of Korean Patent Application No. 10-2017-0170185 filed Dec. 12, 2017 and the priority of Korean Patent Application No. 10-2018-0158452 filed Dec. 10, 2018. The disclosures of such international patent application and Korean priority patent applications are hereby incorporated herein by reference in their respective entireties, for all purposes.

TECHNICAL FIELD

The present invention relates to a microorganism variant having the ability to extracellularly produce heme, and more particularly to a metabolically engineered microorganism variant having the ability to extracellularly produce heme and a method of producing heme using the same.

BACKGROUND ART

Heme, a porphyrin derivative comprising ferrous ion ($Fe^{2+}$) and protoporphyrin, is an organometallic compound that is found in most prokaryotic and eukaryotic cells, functions to carry oxygen, eliminate reactive oxygen species, and produce energy by transferring electrons. Heme is widely used as a bioavailable iron source in the health care and food supplement industries. In particular, hemin is a heme derivative of oxidized form that contains ferric ions ($Fe^{3+}$) possessing chloride ligands, and is used for the treatment of acute intermittent *porphyria*, and thus the demand for heme is increasing. Therefore, efficient production of heme has been of great interest for several decades. Conventional methods of synthesizing heme by chemical synthesis and separating heme from plant tissue and animal blood by organic extraction or enzymatic hydrolysis have disadvantages in that they are complicated, have a low yield, are time-consuming, and not environmentally friendly. Thus, there have been several attempts to produce heme by biosynthetic methods using recombinant microorganisms, particularly *E. coli*. However, since produced heme accumulates in cells, extraction of the heme from the cells is inevitable for future use of the heme, and thus these attempts did not overcome the limitations of conventional heme production. Although there have been attempts to extracellularly produce heme protein or heme peptide from the heme produced using microorganisms (EP 0,631,631; U.S. Pat. No. 5,681,725; and US2016-0340411), extraction of free heme from the extracellularly secreted heme protein or heme peptide is still required for the production of free heme. Thus, for the environmentally friendly, economical, industrial production of free heme, the extracellular production of free heme needs to be achieved.

Heme is an essential compound for almost all microorganisms, but when heme is present at high concentrations, it causes toxicity in various microorganisms (Anzaldi et al., *Infect.Immun.* 78, 4977-4989, 2010). Some microorganisms acquire heme resistance by actively transporting heme or toxic metabolites, generated by heme accumulation, to the outside of the cells. In *E. coli*, the ccmABC genes are known to encode a heme exporter that directly delivers intracellularly synthesized free heme to proteins involved in cytochrome c biosynthesis in the periplasm (Feissner et al., *Mol. Microbiol.* 61:219-231, 2006). Although it has not been reported whether the genes are involved in resistance to toxicity caused by free heme, the present inventors have determined that enhancement of the biosynthesis of free heme can promote the extracellular secretion of heme by the heme exporter expressed from the ccmABC genes, thereby enabling extracellular production of free heme.

The biosynthesis of heme begins with the biosynthesis of 5-aminolevulinate (ALA) (FIG. 1) (Layer G. et al., *Protein Sci.* 19:1137-1161, 2010). ALA is synthesized via two different pathways (C4 and C5 pathways) depending on species. Archaea, plants and most bacteria have the C5 pathway that converts L-glutamate to ALA through a series of reactions that are catalyzed by glutamyl-tRNA synthase (GluRS), glutamyl-tRNA reductase (GluTR) and glutamate-1-semialdehyde 2,1-aminomutase (GSAM). On the other hand, animals (including humans), fungi and purple nonsulfur phototrophic bacteria have the C4 pathway that converts L-glycine and succinyl-CoA to ALA by ALA synthase (ALAS). The two pathways have been actively studied to produce ALA using microorganisms (Ding et al., *J. Ind. Microbiol. Biotechnol.* 44:1127-1135, 2017; Zhang et al., *Sci. Rep.* 5:8584, 2015; Kang et al., *World J. Microbiol. Biotechnol.* 33 doi: 10.1007/s11274-017-2366-7, 2017), but there has been no report on the use of the C5 ALA biosynthetic pathway for the production of heme.

Downstream of the heme biosynthetic pathway, two molecules of ALA synthesized via the C4 or C5 pathway are condensed by porphobilinogen synthase (PBGS) to form porphobilinogen (PBG). Four molecules of PBG are condensed into 1-hydroxymethylbutane (HMB) by porphobilinogen deaminase (PBGD), and HMB is cyclized by uroporphyrinogen III synthase (UROS) (FIG. 1). Then, uroporphyrinogen III is converted to protoporphyrin IX by subsequent reactions, including decarboxylation catalyzed by uroporphyrinogen III decarboxylase (UROD), coproporphyrinogen III oxidase (CPO) and protoporphyrinogen oxidase (PPO), and an oxidation reaction. Finally, ferrochelatase (FECH) converts protoporphyrin IX to heme by insertion of ferrous ion ($Fe^{2+}$).

There have been several attempts to produce heme by engineering *E. coli*. In the first study, an *E. coli* variant was constructed, which constitutively overexpressed 7 genes, including *Rhodobacter capsulatus*-derived hemA gene (hemA$_{Rca}$) encoding ALAS of the C4 pathway, *E. coli*-derived hemB, hemC and hemD, and hemF genes, *Synechocystis* sp.-derived hemE, and *Bacillus subtilis*-derived hemH. The *E. coli* variant produced 3.3±0.3 μM (2.03±0.18 mg/L) of heme in LB medium (Kwon S. J. et al., *Appl. Environ. Microbiol.* 69: 4875-4883, 2003). However, this method had a low yield, because the supply of precursors (L-glycine and succinyl-CoA) was limited and a non-optimal heme biosynthetic pathway was used.

In another study, *Rhodobacter sphaeroides*-derived hemA gene (hemA$_{Rsp}$) encoding ALAS, endogenous maeB encoding NADP-dependent malate dehydrogenase, and endogenous dctA encoding dicarboxylate transporter were coexpressed in *E. coli*. This strain produced 6.4 mg/L of heme in LB medium supplemented with 10 g/L of succinate and 2 g/L of glycine (Kwon O. H. et al., *J. Microbiol. Biotechnol.* 19:604-609, 2009). In an additional study conducted using this strain, when endogenous coaA (encoding pantothenate kinase), hemB, hemC, hemD and hemE genes were overexpressed, 0.49 μmol gDCW$^{-1}$ of heme was produced, but the actual heme concentration could not been seen, because the biomass concentration was not described (Lee M. J. et al. *J. Microbiol. Biotechnol.* 23:668-673, 2013). In a recent study, the researchers produced 9.1 μmol gDCW$^{-1}$ of heme in a 250 mL incubator by continuous culture (here, the biomass concentration cannot also be seen) (Pranawidjaja S. et al., *J. Microbiol. Biotechnol.* 25:880-886, 2015). Although heme could be produced by the above-described recombinant *E. coli* strain, the final titer of heme was very low, and the extracellular secretion of free heme has not been reported. The reason for the low production of heme is mainly because a suboptimal pathway was used to supply heme precursors for heme biosynthesis. In addition, the addition of L-glycine and succinate is not desirable for large-scale production.

Therefore, it is necessary to generate a recombinant microorganism, which effectively produces extracellular free heme, by generating a high-performance heme-producing microorganism for efficient production of heme and confirming extracellular heme secretion caused by an increase in the production of heme.

Accordingly, the present inventors have made extensive efforts to develop a microorganism variant which is capable of producing heme in high yield and secreting the produced heme extracellularly, and as a result, have found that a variant overexpressing the heme biosynthetic pathway and the C5 pathway capable of increasing the production of the heme precursor 5-aminolevulinic acid in *E. coli* that produces heme in a higher yield than conventional heme-producing strains and also extracellularly produces heme. The present inventors also have found that additional overexpression of the gene ccmABC that secretes heme extracellularly further increases the production of heme and also increases extracellular free heme secretion, thereby completing the present invention.

DISCLOSURE OF INVENTION

Technical Problem

It is an object of the present invention to provide a microorganism variant which is capable of producing heme in high yield and secreting the produced heme extracellularly.

Another object of the present invention is to provide a method for producing heme by use of the microorganism variant.

Technical Solution

To achieve the above objects, the present invention provides a microorganism variant capable of producing heme extracellularly, in which a gene encoding a heme exporter is overexpressed in a microorganism having a gene involved in a biosynthetic pathway that produces 5-aminolevulinate (ALA), and a gene involved in a pathway that synthesizes heme from ALA.

The present invention also provides a method of producing heme comprising the steps of: (a) culturing the above-described microorganism variant to produce heme; and (b) obtaining the produced heme.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Unless defined otherwise, all the technical and scientific terms used herein have the same meaning as those generally understood by one of ordinary skill in the art to which the invention pertains. Generally, the nomenclature used herein and the experiment methods, which will be described below, are those well known and commonly employed in the art.

Heme is an organometallic compound which is widely used in the health care and food supplement industries. In a conventional art, heme was produced by chemical synthesis, organic extraction or enzymatic hydrolysis, but this method is complicated and has a low yield. For this reason, an *E. coli* variant was constructed to produce heme in high yield. In addition, an *E. coli* variant was constructed which secretes produced heme extracellularly, making it easy to recover free heme later, unlike a conventional *E. coli* strain that accumulates produced heme in the cells.

Heme is an essential compound for microorganisms, but when heme is present at high concentrations, it causes toxicity. Thus, some microorganisms acquire heme resistance by actively transporting heme or toxic metabolites that are generated by heme accumulation to the outside of the cells. In the case of *E. coli*, the genes ccmABC are known to encode a heme exporter that supplies heme to proteins involved in cytochrome c biosynthesis (Feissner et al., *Mol. Microbiol.* 61:219-231, 2006). However, it has not been reported whether the gene is involved in resistance to toxicity caused by free heme. Nevertheless, the present inventors have determined that enhancement of the biosynthesis of free heme can promote the extracellular secretion of heme by the heme exporter expressed from the ccmABC genes, thereby enabling extracellular production of free heme.

Figure 2:
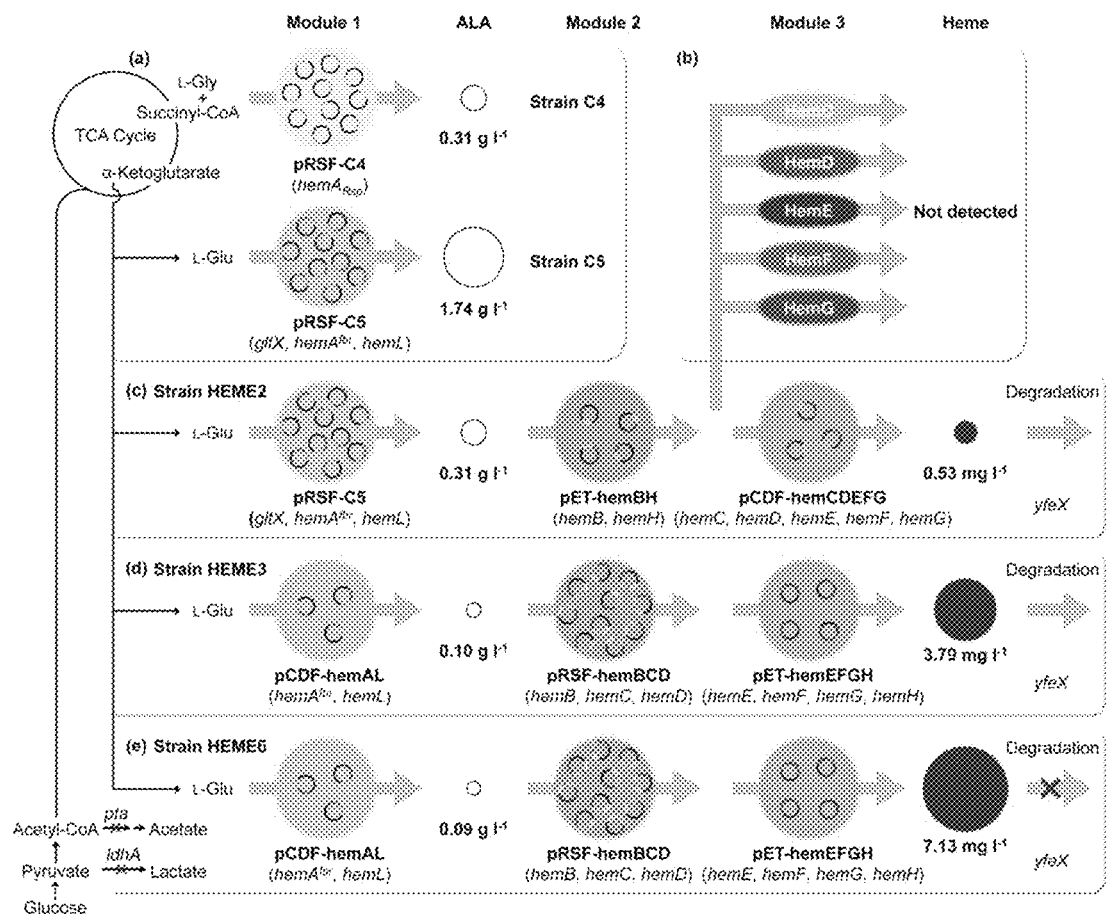
FIG. 2 shows a strategy for producing heme in high yield in an *E. coli* strain according to the present invention.

A conventional heme-producing variant using *E. coli* was designed to produce heme from 5-aminolevulinic acid via the C4 pathway together with the supply of L-glycine and succinate, but the final titer of heme in this variant was very low. To more efficiently produce heme, the present inventors have constructed a metabolically engineered *E. coli* strain utilizing the C5 pathway that converts L-glutamate to 5-aminolevulinic acid, and have increased the production of heme in *E. coli* by using various strategies (FIG. 2).

First, the capacities of the C4 and C5 pathways to produce ALA without feeding precursors were examined. After confirming the superior performance of the C5 pathway over that of the C4 pathway, the metabolic genes of the C5 pathway and downstream pathways for heme biosynthesis were overexpressed. Then, the metabolic pathways associated with heme biosynthesis were optimized by adjusting the expression levels of the relevant genes. To further increase the production of heme, the yfeX gene, which is suspected to encode a heme-degrading enzyme, and lactate and acetate biosynthetic pathways were deleted, and it was confirmed that heme was produced in high titer by batch fermentation. In addition, it was confirmed that the produced heme was secreted extracellularly.

Furthermore, an *E. coli* variant overexpressing the ccmABC genes encoding the heme exporter that secretes heme extracellularly was constructed, and it was confirmed that heme was produced with higher efficiency by batch fermentation. In addition, it was confirmed that a higher proportion of the produced heme was secreted extracellularly.

Therefore, the present invention is directed to a microorganism variant capable of secreting heme extracellularly in which the genes encoding a heme exporter is overexpressed in a microorganism having genes involved in biosynthesis of 5-aminolevulinate (ALA), and genes involved in biosynthesis of heme from ALA.

In the present invention, the microorganism having genes involved in biosynthesis of 5-aminolevulinate (ALA) and genes involved in biosynthesis of heme from ALA includes a microorganism introduced with such genes as well as the microorganism naturally having the genes.

In the present invention, the microorganism variant may be characterized in that the genes involved in biosynthesis of 5-aminolevulinate (ALA) and the genes involved in biosynthesis of heme from ALA are overexpressed.

The precursor 5-aminolevulinate (ALA) is required to biosynthesize heme, and both the C4 pathway and the C5 pathway can supply ALA. Although examples were reported in which both the C4 pathway and the C5 pathway were used to produce ALA, the present invention is the first to apply the C5 pathway to variants for biosynthesis of heme.

The microorganism that can be used in the present invention may be a microorganism capable of producing glutamic acid from a carbon source, but is not limited thereto.

Conventional microorganisms having the ability to biosynthesize heme using the C4 pathway had problems in that AIA precursors (succinate and glycine) need to be added during culture and it is not permitted to add glycine at high concentration, due to its cytotoxicity. In addition, even when succinate and glycine were added, the final titer of heme was no higher than about 6.4 mg/L.

In the present invention, in order to construct a microorganism variant having a high ability to produce heme, microorganism variants having the C4 pathway and the C5 pathway, respectively, were constructed, and their abilities to produce heme were examined.

Examples of the microorganism variants that can be used in the present invention may include bacteria, archaea, yeasts, fungi, protozoa (flagellate, amoebozoa, choanoflagellate, rhizaria, chromalveolata), animal cells, microalgae, and plant cells, more preferably, *Escherichia coli*, *Bacillus* sp., *Corynebacterium* sp., *Lactobacillus* sp., *Lactococcus* sp., *Pseudomonas* sp., *Anacystis* sp., *Anabaena* sp., *Chlorobium* sp., *Chloroflexus* sp., *Clostridium* sp., Methanobacteria, *Propionibacterium* sp., *Rhodopseudomonas* sp., *Rhodobacter* sp., Rhodovulum sp., *Streptococcus* sp., *Saccharomyces* sp., *Schizosaccharomyces* sp., *Yarrowia* sp., and *Aspergillus* sp., further preferably, *Escherichia coli*, *Bacillus subtilis*, *Corynebacterium glutamicum*, *Lactobacillus brevis*, *Lactobacillus casei*, *Lactobacillus reuteri*, *Lactococcus lactis*, *Aspergillus niger*, *Saccharomyceses cerevisiae*, and *Saccharomyces pombe*, but are not limited thereto.

In one example of the present invention, when *E. coli* strains introduced with the C4 pathway and the C5 pathway, respectively, were cultured without adding the precursors, more ALA was produced in the C5 pathway. Thus, in the present invention, the C5 pathway was used for heme biosynthesis.

In the present invention, the genes involved in the C5 biosynthetic pathway may be selected from the group consisting of gltX encoding glutamyl-tRNA synthase (GluRS), hemA encoding glutamyl-tRNA reductase (GluTR), and hemL encoding glutamate-1-semialdehyde 2,1-aminomutase (GSAM), and the gene involved in a pathway that synthesizes heme from ALA may be selected from the group consisting of hemB encoding porphobilinogen synthase (PBGS), hemC encoding porphobilinogen deaminase (PBGD), hemD encoding uroporphyrinogen III synthase (UROS), hemE encoding uroporphyrinogen III decarboxylase (UROD), hemF encoding coproporphyrinogen III oxidase (CPO), hemG encoding protoporphyrinogen oxidase (PPO), and hemH encoding ferrochelatase (FECH).

In the present invention, the variant may be characterized in that a gene encoding a heme exporter is overexpressed.

In the present invention, the variant may lack a gene that encodes a heme or heme intermediate-degrading enzyme, and the gene that encodes a heme or heme intermediate-degrading enzyme may be the yfeX gene.

In another example, an *E. coli* variant was constructed by co-overexpressing the genes of the heme biosynthetic pathway in an *E. coli* strain with the C5 pathway genes overexpressed, optimizing a vector used for expression of each enzyme, deleting genes involved in acetate and lactate production, and deleting the yfeX gene of which involvement in degradation of heme has been controversial. This *E. coli* variant produced 7.13 mg/L of heme in flask culture using LB medium supplemented with 7.5 mg/L of $FeSO_4 7H_2O$.

Therefore, in the present invention, it was first confirmed that the knockout of the yfeX gene increases the production of heme.

Another aspect of the present invention is directed to a variant in which the yfeX gene is deleted in a microorganism in which the C4 pathway of ALA is overexpressed.

In addition, in another example of the present invention, the E. coli variant strain constructed as described above was flask-cultured in an MR medium containing 5 g/L of yeast extract and a $FeSO_4 7H_2O$ concentration adjusted to 7.5 mg/L, and as a result, 7.45 mg/L of heme was produced. Furthermore, the optimization of culture time and temperature was performed, protein overexpression was induced by IPTG, and then culture was performed at 30° C. for 60 hours, and as a result, 7.78 mg/L of heme was produced.

In still another example of the present invention, batch fermentation was performed using the above-described E. coli variant under optimized conditions, and as a result, a total of 14.24 mg/L of heme was produced at 56 hours of culture, and 1.18 mg/L (8.29%) of the produced heme was found extracellularly.

In still another example of the present invention, the E. coli variant was cultured in a fed-batch culture process, and as a result, 49.18 mg/L of heme was produced at 56 hours of culture, and 16.77 mg/L (34.10%) of the produced heme was found extracellularly.

In yet another example of the present invention, fed-batch culture was performed using a medium supplemented with $(NH_4)_2SO_4$ in order to overcome concerns about nitrogen deficiency, because 4 nitrogen (N) atoms were required per mole of heme, and as a result, 104.90 mg/L of heme was produced. 54.61 mg/L (52.06%) of the produced heme was found extracellularly.

In yet another example of the present invention, fed-batch culture was performed using a medium supplemented with 1-glutamate, a precursor of the C5 ALA biosynthesis pathway instead of $(NH_4)_2SO_4$, and as a result, 228.46 mg/L of heme was produced at 64 hours of culture, and 131.90 mg/L (57.734%) of the produced heme was found extracellularly.

Considering the above results, it can be seen that the proportion of extracellularly secreted heme increases as the total amount of heme produced increases. Therefore, it was concluded that, because a high intracellular concentration of heme is cytotoxic, the function or expression of the heme exporter could be promoted, like the hypothesis established by the present inventors. Thus, it was concluded that when the ccmABC gene known to encode the heme exporter is overexpressed, the extracellular secretion of heme will further be promoted, and as a result, toxicity caused by intracellular free heme will decrease and the production of heme will also increase. Based on this conclusion, a method for overexpressing the ccmABC genes was attempted.

Therefore, in another aspect, the present invention is directed to a method for producing heme comprising the steps of: culturing the microorganism variant capable of secreting heme extracellularly, in which genes involved in a C5 biosynthetic pathway that produces 5-aminolevulinate (ALA), and genes involved in a pathway that synthesizes heme from ALA are overexpressed and genes encoding heme exporter is overexpressed, to produce heme; and recovering the produced heme.

In one example of the present invention, a strain constructed by overexpressing the heme exporter-encoding ccmABC genes in the above-described heme-producing E. coli strain was cultured in a fed-batch process in the presence of $(NH_4)_2SO_4$, and as a result, 114.79 mg/L of heme was produced at 64 hours of culture, and 71.91 mg/L (62.64%) of the produced heme was found extracellularly.

In another example of the present invention, the strain of the present invention was cultured in a fed-batch process in the presence of glutamate, and as a result, 246.69 mg/L of heme was produced at 72 hours of culture, and 164.12 mg/L (66.53%) of the produced heme was found extracellularly.

When heme was produced using the microorganism variant of the present invention, in one example, heme was produced in an amount of 114.79 mg/L or 246.69 mg/L, depending on whether the precursors were added. This amount corresponds to a 17.9-fold higher or 38.5-fold higher yield than that of a conventional heme-producing E. coli variant that produced 6.4 mg/L of heme.

In addition, in the present invention, it was first confirmed that as the amount of heme produced by a microorganism increases, the proportion of extracellular heme also increases. Furthermore, it was first confirmed that when the heme exporter genes ccmABC are overexpressed, the proportion of extracellular heme increases and the total amount of heme produced by the cells also increases.

Hereinafter, the present invention will be described in further detail with reference to examples. It will be obvious to a person having ordinary skill in the art that these examples are for illustrative purposes only and are not to be construed to limit the scope of the present invention.

The restriction enzymes used in these examples and the following examples were purchased from New England Biolabs (USA) and Enzynomics (Korea), and the PCR polymerase was purchased from BIOFACT (Korea), and the DNA ligase was purchased from Elpis Biotech (Korea). Others were indicated separately.

Example 1: Selection of an ALA Biosynthetic Pathway for Highly Efficient Production of Heme

1-1: Construction of Vectors (pRSF-C4 and pRSF-05) Expressing C4 and C5 ALA Biosynthetic Genes pRSF-C4 and pRSF-05 vectors capable of expressing C4 and C5 ALA biosynthetic genes in the E. coli strain BL21 (DE3) (Studier et al., J. Mol. Biol. 189:113-130, 1986) were constructed through the following procedures.

The plasmid pRSF-C4 capable of expressing the C4 ALA biosynthetic genes was constructed by inserting an aminolevulinic acid synthase (ALAS) gene (hemA$_{Rsp}$) derived from Rhodobacter sphaeroides 2.4.1 and maeB and coaA genes derived from E. coli into a plasmid pRSFDuet-1 (Novagen, USA). To amplify the hemA$_{Rsp}$ gene derived from Rhodobacter sphaeroides 2.4.1, the hemA$_{Rsp}$ gene (SEQ ID NO: 1) codon-optimized according to the codon usage of E. coli was synthesized (Genotech, Korea), thereby preparing a template, and PCR was performed using the template and the primers of SEQ ID NOs: 2 and 3. The maeB gene (SEQ ID NO: 4) and coaA gene (SEQ ID NO: 5) derived from E. coli were amplified using the genomic DNA of E. coli BL21 (DE3) as a template and also using the primers of SEQ ID NOs: 6 and 7 and the primers of SEQ ID NOs: 8 and 9, respectively. At this time, the sequence of a ribosome binding site (RBS) was added to the 5' end of the amplified coaA gene by the sequence of the ribosome binding site (RBS) contained in the primer of SEQ ID NO: 7 used in the amplification process.

TABLE 1

| SEQ ID NOs | Nucleotide sequences |
|---|---|
| SEQ ID NO: 2 | 5'-CATGCCATGG ATTATAACCT GGCACTGG-3' |
| SEQ ID NO: 3 | 5'-CCGGAATTCT TAGGCAACCA CTTCCGC-3' |

TABLE 1-continued

| SEQ ID NOs | Nucleotide sequences |
|---|---|
| SEQ ID NO: 6 | 5'-GAAGATCTAT GGATGACCAG TTAAAACAAA G-3' |
| SEQ ID NO: 7 | 5'-CCGCTCGAGT TACAGCGGTT GGGTTTG-3' |
| SEQ ID NO: 8 | 5'-CGAGCTCATA AAAGGAGGAA AATATATGAG TATAAAAGAG CAAACGTT-3' |
| SEQ ID NO: 9 | 5'-ACGCGTCGAC TTATTTGCGT AGTCTGACCT CT-3' |

The amplified sequences were cleaved with BglII and XhoI, SacI and SalI, and NcoI and EcoRI, respectively, and then sequentially inserted into a pRSFDuet-1 vector (Novagen, USA) cleaved with the same restriction enzymes, thereby constructing pRSF-C4.

The vector pRSF-C5 capable of expressing the C5 ALA biosynthetic genes was constructed by inserting the gltX gene (SEQ ID NO: 10), hemL gene (SEQ ID NO: 11) and negative feedback resistance hemA (hemA$^{fbr}$) gene (SEQ ID NO: 12), which are derived from E. coli. Each of the genes was amplified using the genomic DNA of E. coli BL21 (DE3) as a template, and also using the primers of SEQ ID NO: 13 and SEQ ID NO: 14, the primers of SEQ ID NO: 15 and SEQ ID NO: 16, and the primers of SEQ ID NO: 17 and SEQ ID NO: 18, respectively.

At this time, the sequence of a ribosome binding site (RBS) was added to the 5' end of the amplified hemL gene by the sequence of the ribosome binding site (RBS) contained in the primer of SEQ ID NO: 15 used in the amplification process. In addition, the hemA gene derived from BL21(DE3) was converted to the negative feedback resistance hemA (hemA$^{fbr}$) by the nucleotide sequence encoding threonine and leucine, contained in the primer of SEQ ID NO: 17.

TABLE 2

| SEQ ID NOs | Nucleotide sequences |
|---|---|
| SEQ ID NO: 13 | 5'-GGAATTCCAT ATGAAAATCA AAACTCGCTT C-3' |
| SEQ ID NO: 14 | 5'-CCGCTCGAGT TACTGCTGAT TTTCGCGT-3' |
| SEQ ID NO: 15 | 5'-CGAGCTCATA AAAGGAGGAA AATATATGAG TAAGTCTGAA AATCTTTACA G-3' |
| SEQ ID NO: 16 | 5'-AAGGAAAAAA GCGGCCGCTC ACAACTTCGC AAACACC-3' |
| SEQ ID NO: 17 | 5'-CATGCCATGG GTACCAAGAA GCTTTTAGCA CTCGGTATCA ACC-3' |
| SEQ ID NO: 18 | 5'-CGCGGATCCC TACTCCAGCC CGAGGCT-3' |

The amplified gltX, hemA$^{fbr}$ and hemL gene sequences were cleaved with NdeI and XhoI, NcoI and BamHI, and SacI and NotI, respectively, and then sequentially inserted into a pRSFDuet-1 vector (Novagen, USA) cleaved with the same restriction enzymes, thereby constructing pRSF-05.

1-2: Comparison of ALA Production Between E. coli BL21(DE3) Strains that Overexpressed the C4 and C5 ALA Biosynthetic Genes To compare ALA production obtained when strains introduced with the C4 and C5 ALA biosynthetic pathways, respectively, were cultured without feeding precursors which are used by the respective pathways (glycine and succinate for the C4 ALA biosynthetic pathway, and glutamate for the C5 ALA biosynthetic pathway), each of the pRSF-C4 and pRSF-05 vectors constructed in Example 1-1 was introduced into an E. coli BL21(DE3) strain, thereby constructing an E. coli C4 strain and an E. coli C5 strain (Table 3). As a negative control, E. coli BL21(DE3) was used (Table 3).

TABLE 3

| Strain | Description |
|---|---|
| BL21(DE3) | E. coli BL21(DE3) |
| C4 | E. coli BL21(DE3) harboring pRSF-C4 |
| C5 | E. coli BL21(DE3) harboring pRSF-C5 |

Each of the strains shown in Table 3 was used to inoculate 5 mL of LB medium (10 g/L NaCl, 10 g/L tryptone, g/L yeast extract) supplemented with 25 μg/mL of kanamycin, and was then cultured at 37° C. and 220 rpm for 12 hours. To produce ALA using the strains, 1 mL of the pre-culture was transferred to 50 mL of the same fresh medium, and then cultured in a 250-mL Erlenmeyer flask at 37° C. and 200 rpm until the $OD_{600}$ reached about 0.6. Next, 1 mM IPTG was added to the medium, and then the cells were cultured at 30° C. and 200 rpm for 48 hours.

After the culture, samples were collected to analyze the production of ALA, and then the samples were pretreated and analyzed by a previously reported method (Burnham, *Methods Enzymol.* 17A, 195-204, 1970). As a result, it was shown that 0.02 g/L, 0.31 g/L and 1.74 g/L of ALA were produced in the BL21(DE3) strain (negative control), the C4 strain and the C5 strain, respectively, indicating that when the precursors are not fed, the production of ALA by the C5 ALA biosynthetic pathway is at least 5-fold higher than that by the C4 ALA biosynthetic pathway (FIG. 2 in diagram (a)). Therefore, it was decided to use the C5 ALA biosynthetic pathway for ALA biosynthesis in the subsequent construction of a heme-producing strain.

Figure 1:
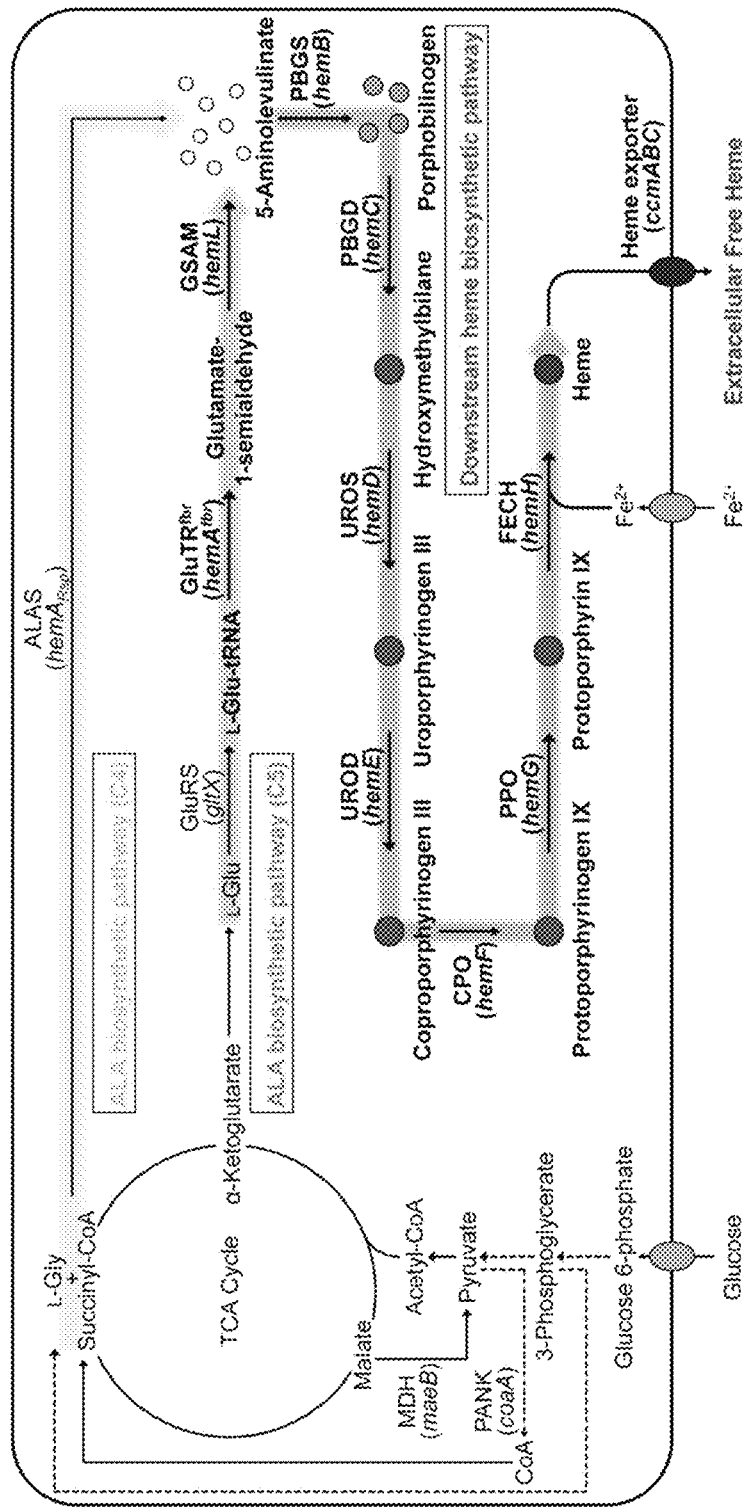
FIG. 1 shows a biosynthetic pathway for heme production according to the present invention. The items in bold indicate that the corresponding genes overexpressed in a HEME7 strain according to the present invention.

Example 2: Construction of Heme-Producing Strain Introduced with C5 ALA Biosynthetic Pathway 2-1: Selection of Overexpressing Target Gene for Heme Production To produce heme from the ALA produced via the ALA biosynthetic pathway, the enzymes expressed from hemB, hemC, hemD, hemE, hemF, hemG and hemH genes are required (FIG. 1). Since E. coli endogenously has the genes, wild-type strains can also produce heme, but produce heme only in an amount necessary for their survival. For this reason, the produced heme is mostly present in a form bound to protein, and thus it is difficult to detect free heme in wild-type strains. Thus, in order to overproduce free heme, the metabolic fluxes involved in producing heme from ALA by overexpressing the genes need to be increased. However, it was concluded that when the genes are all overexpressed, an overload can be placed on the metabolism of the heme-producing strain due to overexpression of the proteins. Accordingly, only genes whose additional overexpression is necessary due to their insufficient expression intensities for overproducing heme in the *E. coli* BL21(DE3) strain were selected, and only minimal heme biosynthetic genes were selectively overexpressed to minimize the strain's overload caused by protein overexpression and maximize the overproduction of heme.

(a) Confirmation of the Need for Overexpression of hemB and hemH Genes for Heme Production It was reported that when the hemB gene (SEQ ID NO: 19) and hemH gene (SEQ ID NO: 20) among the heme biosynthetic genes are overexpressed, the production of ALA used as a precursor in heme production decreases (Zhang et al., *Sci. Rep.* 5, 8584, 2015), and on the contrary, when the expression levels of the two genes are decreased, the metabolism of the metabolic pathway that produces heme from ALA decreases (Li et al., *FETES Microbiol. Lett.* 350, 209-215, 2014). Thus, it was concluded that overexpression of the hemB and hemH genes is necessary for effective heme overproduction.

The vector pET-hemBH, which overexpresses the two genes and does not interfere with a plasmid overexpressing the C5 ALA biosynthetic pathway, was constructed through the following procedure.

The primers of SEQ ID NOs: 21 and 22 and the primers of SEQ ID NOs: 23 and 24 were respectively used to amplify the hemB and hemH genes from the genomic DNA of the *E. coli* BL21(DE3) strain.

TABLE 4

| SEQ ID NOs: | Nucleotide sequences |
|---|---|
| SEQ ID NO: 21 | 5'-GGAATTCCAT ATGACAGACT TAATCCAACG C-3' |
| SEQ ID NO: 22 | 5'-CCGCTCGAGT TAACGCAGAA TCTTCTTCTC AG-3' |
| SEQ ID NO: 23 | 5'-GGAATTCCAT ATGCGTCAGA CTAAAACCGG-3' |
| SEQ ID NO: 24 | 5'-CCGCTCGAGT TAGCGATACG CGGCAAC-3' |

Each of the amplified sequences was cleaved with NdeI and XhoI, and then inserted into a pETDuet-1 vector (Novagen, USA) cleaved with the same restriction enzymes, thereby constructing pET-hemB and pET-hemH.

The primers of SEQ ID NOs: 25 and 26 were used to amplify the hemB gene from the genomic DNA of the *E. coli* BL21(DE3) strain, and each of the amplified sequences was cleaved with NcoI and BamHI, and then inserted into a pET-hemH vector (Novagen, USA) cleaved with the same restriction enzymes, thereby constructing pET-hemBH.

TABLE 5

| SEQ ID NOs | Nucleotide sequences |
|---|---|
| SEQ ID NO: 25 | 5'-CATGCCATGG GTACAGACTT AATCCAACGC-3' |
| SEQ ID NO: 26 | 5'-CGCGGATCCT TAACGCAGAA TCTTCTTCTC AG-3' |

Each of the constructed pET-hemB, pET-hemH and pET-hemBH was introduced into a recombinant *E. coli* C5 strain, thereby constructing *E. coli* C5-B, C5-H and C5-BH strains (Table 6).

TABLE 6

| Strain | Description |
|---|---|
| C5-B | *E. coli* BL21(DE3) harboring pRSF-C5 and pET-hemB |
| C5-H | *E. coli* BL21(DE3) harboring pRSF-C5 and pET-hemH |
| C5-BH | *E. coli* BL21(DE3) harboring pRSF-C5 and pET-hemBH |

In order to identify the profiles of ALA production, heme and heme biosynthetic intermediates (uroporphyrinogen III, coproporphyrinogen III, and protoporphyrin IX) in the constructed *E. coli* strains, each of the strains shown in Table 6 above was used to inoculate 5 mL of LB medium (10 g/L NaCl, 10 g/L tryptone, 5 g/L yeast extract) containing 25 μg/mL of kanamycin and 50 μg/mL of ampicillin, and was then cultured at 37° C. and 220 rpm for 12 hours. For main culture for heme production, 1 mL of the pre-culture was transferred to 50 mL of LB-Fe7.5 medium (10 g/L NaCl, 10 g/L tryptone, 5 g/L yeast extract, 7.5 mg/L FeSO$_4$7H$_2$O) containing the same antibiotics, and then the cells were cultured in a 250-mL Erlenmeyer flask at 37° C. and 200 rpm until the OD$_{600}$ reached about 0.6. Next, 1 mM IPTG was added to the culture medium, and then the cells were cultured at 30° C. and 200 rpm for 48 hours.

After the culture, samples were collected to analyze the production of ALA, and then the samples were pretreated and analyzed by a previously reported method (Burnham, *Methods Enzymol.* 17A, 195-204, 1970).

In addition, in order to analyze the production of heme, 1 mL of a sample was collected from each culture medium and centrifuged, and the collected cells were resuspended in 500 μL of 1 M NaOH aqueous solution and lysed by ultrasonic disruption. The prepared samples were filtered, and then the concentrations of heme therein were measured by a previously known method using HPLC (Lee et al., *J. Microbiol. Biotechnol.* 22, 1653-1658, 2012).

To confirm the heme biosynthetic intermediates, the same samples as used to analyze the production of heme were used, but a previously reported method using HPLC-MS was used (Pranawidjaja et al., *J. Microbiol. Biotechnol.* 25, 880-886, 2015; Bu et al., *J. Chromatogr. B Analyt. Technol. Biomed. Life Sci.* 783, 411-423, 2003).

As a result, as expected, the C5-BH strain produced large amounts of the heme biosynthetic intermediates (uroporphyrinogen III and coproporphyrinogen III) than the other two strains (Table 7). In addition, the amount of ALA found was smaller in C5-BH than in C5-B and C5-H. However, free heme could not be detected in all the three strains.

TABLE 7

| Strains | ALA (g l$^{-1}$) | Uroporphyrinogen III (AU)$^b$ | Coproporphyrinogen III (AU)$^b$ | Protoporphyrin IX (AU)$^b$ | Heme (g l$^{-1}$) |
|---|---|---|---|---|---|
| C5-B | 0.712 | 153 | 119 | — | — |
| C5-H | 1.409 | — | — | — | — |
| C5-BH | 0.726 | 787 | 158 | — | — |

(b) Confirmation of the Need for Overexpression of hemC, hemD, hemE, hemF and hemG Genes for Overproduction of Heme In order to select genes of which overexpression is necessary for overproduction of heme among the remaining five genes (hemC(SEQ ID NO: 27), hemD(SEQ ID NO: 28), hemE(SEQ ID NO: 29), hemF(SEQ ID NO: 30), hemG (SEQ ID NO: 31)) other than the hemB and hemH genes among the heme biosynthetic genes, each of the five genes was overexpressed in the C5-BH strain, and then the production of heme and the profiles of production of heme biosynthetic intermediates were analyzed. Plasmids pCDF-hemC, pCDF-hemD, pCDF-hemE, pCDF-hemF and pCDF-hemG respectively overexpressing the five genes were constructed through the following procedure.

The primers of SEQ ID NOs: 32 and 33, the primers of SEQ ID NOs: 34 and 35, the primers of SEQ ID NOs: 36 and 37, the primers of SEQ ID NOs: 38 and 39, and the primers of SEQ ID NOs: 40 and 41 were respectively used to amplify the hemC, hemD, hemE, hemF, and hemG genes from the genomic DNA of the *E. coli* BL21(DE3) strain.

TABLE 8

| SEQ ID NOs | Nucleotide sequences |
|---|---|
| SEQ ID NO: 32 | 5'-CATGCCATGG GTATGTTAGA CAATGTTTTA AGAATTGC-3' |
| SEQ ID NO: 33 | 5'-CGCGGATCCT CATGCCGGAG CGTCTC-3' |
| SEQ ID NO: 34 | 5'-CATGCCATGG GTATGAGTAT CCTGGTCACC CG-3' |
| SEQ ID NO: 35 | 5'-CGCGGATCCT TATTGTAATG CCCGTAAAAG C-3' |
| SEQ ID NO: 36 | 5'-CATGCCATGG GTATGACCGA ACTTAAAAAC GATC-3' |
| SEQ ID NO: 37 | 5'-CCGGAATTCT TAGCGGTGAT ATTGTTCAGA C-3' |
| SEQ ID NO: 38 | 5'-CATGCCATGG GTATGAAACC CGACGCACAC-3' |
| SEQ ID NO: 39 | 5'-CGCGGATCCT TACACCCAAT CCCTGACCT-3' |
| SEQ ID NO: 40 | 5'-CATGCCATGG GTGTGAAAAC ATTAATTCTT TTCTCAAC-3' |
| SEQ ID NO: 41 | 5'-CGAGCTCTTA TTTCAGCGTC GGTTTGTC-3' |

Each of the amplified genes was cleaved with NcoI and BamHI, NcoI and BamHI, NcoI and EcoRI, NcoI and BamHI, and NcoI and SacI, and then inserted into a pCDF-Duet-1 vector (Novagen, USA) cleaved with the same restriction enzymes, thereby constructing pCDF-hemC, pCDF-hemD, pCDF-hemE, pCDF-hemF, and pCDF-hemG, respectively.

Each of the constructed pCDF-hemC, pCDF-hemD, pCDF-hemE, pCDF-hemF, and pCDF-hemG was introduced into a recombinant *E. coli* C5-BH strain, thereby constructing *E. coli* C5-BCH, C5-BDH, C5-BEH, C5-BFH, and C5-BGH strains (Table 9).

TABLE 9

| Strain | Description |
|---|---|
| C5-BCH | *E. coli* BL21(DE3) harboring pRSF-C5, pET-hemBH, and pCDF-hemC |
| C5-BDH | *E. coli* BL21(DE3) harboring pRSF-C5, pET-hemBH, and pCDF-hemD |
| C5-BEH | *E. coli* BL21(DE3) harboring pRSF-C5, pET-hemBH, and pCDF-hemE |
| C5-BFH | *E. coli* BL21(DE3) harboring pRSF-C5, pET-hemBH, and pCDF-hemF |
| C5-BGH | *E. coli* BL21(DE3) harboring pRSF-C5, pET-hemBH, and pCDF-hemG |

In order to identify the profiles of production of ALA, heme and heme biosynthetic intermediates (uroporphyrinogen III, coproporphyrinogen III, and protoporphyrin IX) in the constructed *E. coli* strains, each of the strains shown in Table 9 above was used to inoculate 5 mL of LB medium (10 g/L NaCl, 10 g/L tryptone, 5 g/L yeast extract) containing 25 µg/mL of kanamycin and 50 µg/mL of ampicillin, and was then cultured at 37° C. and 220 rpm for 12 hours. For main culture for heme production, 1 mL of the pre-culture was transferred to 50 mL of LB-Fe7.5 medium (10 g/L NaCl, 10 g/L tryptone, 5 g/L yeast extract, 7.5 mg/L FeSO$_4$7H$_2$O) containing the same antibiotics, and then the cells were cultured in a 250-mL Erlenmeyer flask at 37° C. and 200 rpm until the OD$_{600}$ reached about 0.6. Next, 1 mM IPTG was added to the culture medium, and then the cells were cultured at 30° C. and 200 rpm for 48 hours.

After the culture, samples were collected to analyze the production of ALA, and then the samples were pretreated and analyzed by a previously reported method (Burnham, *Methods Enzymol.* 17A, 195-204, 1970).

In addition, in order to analyze the production of heme, 1 mL of a sample was collected from each culture medium and centrifuged, and the collected cells were resuspended in 500 µL of 1 M NaOH aqueous solution and lysed by ultrasonic disruption. The prepared samples were filtered, and then the concentrations of heme therein were measured by a previously known method using HPLC (Lee et al., *J. Microbiol. Biotechnol.* 22, 1653-1658, 2012).

To confirm the heme biosynthetic intermediates, the same samples as used to analyze the production of heme were used, but a previously reported method using HPLC-MS was used (Pranawidjaja et al., *J. Microbiol. Biotechnol.* 25, 880-886, 2015; Bu et al., *J. Chromatogr. B Analyt. Technol. Biomed. Life Sci.* 783, 411-423, 2003).

As a result, although heme was not detected in all the five strains (FIG. 2 in diamgram (b)), the signal of uroporphyrinogen III detected was higher in the C5-BCH and C5-BDH strains than in the C5-BH strain (Table 7), and the signal of coproporphyrinogen III detected was higher in the C5-BDH, C5-BEH and C5-BFH strains than in the C5-BH strain. In particular, in the C5-BDH strain, protoporphyrin IX that was not detected in the C5-BH strain was detected. Based on the above results, it was concluded that overexpression of the hemC, hemD, hemE and hemF genes is essential for the effective production of heme.

TABLE 10

| Strains | ALA (g l$^{-1}$) | Uroporphyrinogen III (AU)$^b$ | Coproporphyrinogen III (AU)$^b$ | Protoporphyrin IX (AU)$^b$ | Heme (g l$^{-1}$) |
|---|---|---|---|---|---|
| C5-BCH | 0.553 | 1259 | 164 | — | — |
| C5-BDH | 0.459 | 1460 | 429 | 89 | — |
| C5-BEH | 0.494 | 693 | 549 | — | — |
| C5-BFH | 0.462 | 680 | 525 | — | — |
| C5-BGH | 0.463 | 717 | 134 | — | — |

However, the C5-BGH strain did not significantly differ from the C5-BH strain (Table 7) in terms of the production of ALA and heme biosynthetic intermediates (Table 10). In order to confirm again whether overexpression of hemG is essential for heme overproduction, the strain HEME1 overexpressing the hemC, hemD, hemE and hemF genes was constructed based on the C5-BH strain, and the strain HEME2 overexpressing all the hemC, hemD, hemE, hemF and hemG genes was constructed based on the C5-BH strain through the following procedures.

A plasmid pCDF-hemCDEF overexpressing the hemC, hemD, hemE and hemF genes was constructed through the following procedure.

The primers of SEQ ID NOs: 42 and 43, the primers of SEQ ID NOs: 44 and 45, the primers of SEQ ID NOs: 46 and 47, and the primers of SEQ ID NOs: 48 and 49 were respectively used to amplify the hemC, hemD, hemE and hemF genes from the genomic DNA of the *E. coli* BL21 (DE3) strain.

At this time, the sequence of a ribosome binding site (RBS) was added to the 5' ends of the amplified hemD and hemF genes by the sequence of the ribosome binding site (RBS) contained in the primers of SEQ ID NOs: 44 and 48 used in the amplification process.

TABLE 11

| SEQ ID NOs | Nucleotide sequences |
|---|---|
| SEQ ID NO: 42 | 5'-GGGAATTCCA TATGTTAGAC AATGTTTTAA GAATTGC-3' |
| SEQ ID NO: 43 | 5'-GAAGATCTTC ATGCCGGAGC GTCTC-3' |
| SEQ ID NO: 44 | 5'-GAAGATCTAT AAAAGGAGGA AAATATATGA GTATCCTGGT CACCCG-3' |
| SEQ ID NO: 45 | 5'-CCGCTCGAGT TATTGTAATG CCCGTAAAAG C-3' |
| SEQ ID NO: 46 | 5'-CATGCCATGG GTACCGAACT TAAAAACGAT C-3' |
| SEQ ID NO: 47 | 5'-CGAGCTCTTA GCGGTGATAT TGTTCAGAC-3' |
| SEQ ID NO: 48 | 5'-CGAGCTCATA AAAGGAGGAA AATATATGAA ACCCGACGCA CAC-3' |
| SEQ ID NO: 49 | 5'-AAAACTGCAG TTACACCCAA TCCCTGACCT-3' |

Each of the amplified sequences was cleaved with NdeI and BglII, BglII and XhoI, NcoI and SacI, and SacI and PstI, and then sequentially inserted into a pCDFDuet-1 vector (Novagen, USA) cleaved with the same restriction enzymes, thereby constructing pCDF-hemCDEF.

A plasmid pCDF-hemCDEFG overexpressing the hemC, hemD, hemE, hemF, and hemG genes was constructed through the following procedure.

The primers of SEQ ID NOs: 50 and 51 were respectively used to amplify the hemG gene from the genomic DNA of the *E. coli* BL21(DE3) strain. At this time, the sequence of a ribosome binding site (RBS) was added to the 5' end of the amplified hemG gene by the sequence of the ribosome binding site (RBS) contained in the primer of SEQ ID NO: 50 used in the amplification process.

TABLE 12

| SEQ ID NOs | Nucleotide sequences |
|---|---|
| SEQ ID NO: 50 | 5'-AAAACTGCAG ATAAAAGGAG GAAAATATGT GAAAACATTA ATTCTTTTCT CAAC-3' |
| SEQ ID NO: 51 | 5'-AAGGAAAAAA GCGGCCGCTT ATTTCAGCGT CGGTTTGTC-3' |

Each of the amplified sequences was cleaved with PstI and NotI, and then inserted into a pCDF-hemCDEF vector (Novagen, USA) cleaved with the same restriction enzymes, thereby constructing pCDF-hemCDEFG.

Each of the constructed pCDF-hemCDEF and pCDF-hemCDEFG was introduced into a recombinant *E. coli* C5-BH strain, thereby constructing *E. coli* HEME1 and HEME2 strains (FIG. 2 in diagram (c) and Table 13).

TABLE 13

| Strain | Description |
|---|---|
| HEME1 | *E. coli* BL21(DE3) harboring pRSF-C5, pET-hemBH, and pCDF-hemCDEF |
| HEME2 | *E. coli* BL21(DE3) harboring pRSF-C5, pET-hemBH, and pCDF-hemCDEFG |

In order to identify the profiles of production of ALA and heme in the constructed *E. coli* strains, each of the strains shown in Table 13 above was used to inoculate 5 mL of LB medium (10 g/L NaCl, 10 g/L tryptone, 5 g/L yeast extract) containing 25 μg/mL of kanamycin, 50 μg/mL of ampicillin, and 100 μg/mL streptomycin, and was then cultured at 37° C. and 220 rpm for 12 hours. For main culture for heme production, 1 mL of the culture medium in which the cultured cells were growing was used to inoculate 50 mL of LB-Fe7.5 medium (10 g/L NaCl, 10 g/L tryptone, 5 g/L yeast extract, 7.5 mg/L $FeSO_4 7H_2O$) containing the same antibiotics, and then the cells were cultured in a 250-mL Erlenmeyer flask at 37° C. and 200 rpm until the $OD_{600}$ reached about 0.6. Next, 1 mM IPTG was added to the culture medium, and then the cells were cultured at 30° C. and 200 rpm for 48 hours.

After the culture, samples were collected to analyze the production of ALA, and then the samples were pretreated and analyzed.

In addition, in order to analyze the production of heme, 1 mL of a sample was collected from each culture medium and centrifuged, and the collected cells were resuspended in 500 μL of 1 M NaOH aqueous solution and lysed by ultrasonic disruption. The prepared samples were filtered, and then the concentrations of heme therein were measured using HPLC.

Figure 3:
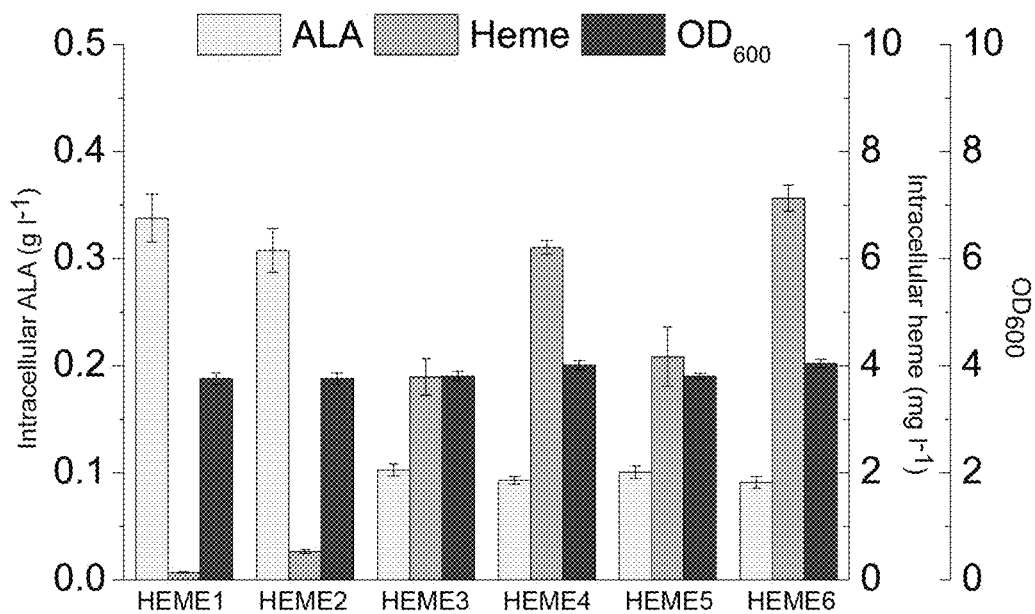
FIG. 3 shows the amounts of ALA and heme produced by flask culture of HEME1, HEME2, HEME3, HEME4, HEME5 and HEME6 strains according to the present invention.

As a result, 0.14 mg/L and 0.53 mg/L of heme were detected in the HEME1 and HEME2 strains, respectively (FIG. 3). From the fact that the production of heme in the HEME2 strain in which the hemG gene was additionally overexpressed was at least 3-fold higher than that in the HEME1 strain, it was concluded that the hemC, hemD, hemE, hemF and hemG genes all need to be overexpressed in the C5-BH strain to effectively overproduce heme.

2-2: Regulation of Overexpression Levels of Heme Biosynthetic Genes for Increased Production of Heme Since the production of ALA (308 mg/L) in the HEME2 strain constructed in Example 2-1 was significantly higher than the production of heme (0.53 mg/L), it was considered that the metabolic flux of the ALA biosynthetic pathway is excessive. Under the assumption that the total amount of proteins that can be overexpressed in a strain is limited, the production of heme was increased by enhancing the expression of metabolic proteins responsible for production of heme from ALA and reducing the expression of metabolic proteins responsible for the relatively excessive ALA-producing pathway, through the following procedures.

(a) Construction of plasmid pCDF-hemAL

Based on the plasmid pCDFDuet-1 having a lower copy number than the plasmid pRSFDuet-1 (Novagen, USA), the genes of the C5 ALA biosynthetic pathway were overexpressed, so that the expression levels of the ALA biosynthetic pathway could be reduced compared to when pRSF-C5 was used, and as a result, the metabolism of the corresponding pathway could also be reduced. In addition, the gene gltX encoding glutamyl tRNA synthetase (GluRS) that converts glutamate to glutamyl-tRNA in the C5 ALA biosynthetic pathway was not overexpressed so that the overexpression levels of other proteins could be increased. Based on pCDFDuet-1, the plasmid pCDF-hemAL overexpressing the C5 ALA biosynthetic pathway was constructed through the following procedures.

The primers of SEQ ID NOs: 15 and 16 and the primers of SEQ ID NOs: 17 and 18 were respectively used to amplify the hemL and negative feedback-resistant hemA (hemA$^{fbr}$) genes from the genomic DNA of the *E. coli* BL21(DE3) strain.

At this time, the sequence of a ribosome binding site (RBS) was added to the 5' end of the amplified hemL gene by the sequence of the ribosome binding site (RBS) contained in the primer of SEQ ID NO: 15 used in the amplification process. In addition, the hemA gene derived from BL21(DE3) was converted to the negative feedback-resistant hemA (hemA$^{fbr}$) by inserting the nucleotide sequence encoding threonine and leucine, contained in the primer of SEQ ID NO: 17.

The amplified DNA fragments were cleaved with NcoI and BamHI, and SacI and NotI, respectively, and then sequentially inserted into plasmid pCDFDuet-1 (Novagen, USA) cleaved with the same restriction enzymes, thereby constructing pCDF-hemAL.

(b) Construction of plasmid pRSF-hemBCD

Based on the plasmid pRSFDuet-1 having a higher copy number than the plasmid pETDuet-1, the hemB, hemC and hemD genes involved in the upstream of the metabolic pathway that produces heme from ALA were overexpressed so that the flux of the metabolic pathway that produces heme from ALA would be increased. Based on pRSFDuet-1, the plasmid pRSF-hemBCD overexpressing the hemB, hemC, hemD genes was constructed through the following procedures.

The primers of SEQ ID NOs: 25 and 26, the primers of SEQ ID NOs: 42 and 43, and the primers of SEQ ID NOs: 44 and 45 were respectively used to amplify the hemB, hemC, and hemD genes from the genomic DNA of the *E. coli* BL21(DE3) strain.

At this time, the sequence of a ribosome binding site (RBS) was added to the 5' end of the amplified hemD gene by the sequence of the ribosome binding site (RBS) contained in the primer of SEQ ID NO: 44 used in the amplification process.

The amplified DNA fragments were cleaved with NcoI and BamHI, NdeI and BglII, and BglII and XhoI, respectively, and then sequentially inserted into a pRSFDuet-1 vector (Novagen, USA) cleaved with the same restriction enzymes, thereby constructing pRSF-hemBCD.

(c) Construction of Plasmid pET-hemEFGH

Based on the plasmid pETDuet-1 having a higher copy number than the plasmid pCDFDuet-1, the hemE, hemF, hemG and hemH genes involved in the downstream of the metabolic pathway that produces heme from ALA were overexpressed so that the flux of the metabolic pathway that produces heme from ALA would be increased. Based on pETDuet-1, the plasmid pET-hemEFGH overexpressing the hemE, hemF, hemG and hemH genes was constructed through the following procedures.

The primers of SEQ ID NOs: 46 and 47, the primers of SEQ ID NOs: 48 and 49, the primers of SEQ ID NOs: 50 and 51, and the primers of SEQ ID NOs: 23 and 24 were respectively used to amplify the hemE, hemF, hemG and hemH genes from the genomic DNA of the *E. coli* BL21 (DE3) strain.

At this time, the sequence of a ribosome binding site (RBS) was added to the 5' ends of the amplified hemF and hemG genes by the sequence of the ribosome binding site (RBS) contained in the primers of SEQ ID NOs: 48 and 50 used in the amplification process.

The amplified sequences were cleaved with NcoI and SacI, SacI and PstI, PstI and NotI, and NdeI and XhoI, respectively, and then sequentially inserted into a pET-Duet-1 vector (Novagen, USA) cleaved with the same restriction enzymes, thereby constructing pET-hemEFGH.

(d) Construction of Recombinant *E. coli* HEME3

The constructed pCDF-hemAL, pRSF-hemBCD and pET-hemEFGH plasmids were introduced together into the *E. coli* BL21(DE3) strain, thereby constructing an *E. coli* HEME3 strain (FIG. 2 in diagram (d) and Table 14).

TABLE 14

| Strain | Description |
| --- | --- |
| HEME3 | *E. coli* BL21(DE3) harboring pCDF-hemAL, pRSF-hemBCD, and pET-hemEFGH |

In order to identify the profiles of ALA and heme production in the constructed *E. coli* strains, each of the strains shown in Table 14 above was used to inoculate 5 mL of LB medium (10 g/L NaCl, 10 g/L tryptone, 5 g/L yeast extract) containing 25 μg/mL of kanamycin, 50 μg/mL of ampicillin, and 100 μg/mL streptomycin, and was then cultured at 37° C. and 220 rpm for 12 hours. For main culture for heme production, 1 mL of the pre-culture was transferred to 50 mL of LB-Fe7.5 medium (10 g/L NaCl, 10 g/L tryptone, 5 g/L yeast extract, 7.5 mg/L FeSO$_4$7H$_2$O) containing the same antibiotics, and then the cells were cultured in a 250-mL Erlenmeyer flask at 37° C. and 200 rpm until the OD$_{600}$ reached about 0.6. Next, 1 mM IPTG was added to the culture medium, and then the cells were cultured at 30° C. and 200 rpm for 48 hours.

After the culture, samples were collected to analyze the production of ALA, and then the samples were pretreated and analyzed by a previously reported method (Burnham, *Methods Enzymol.* 17A, 195-204, 1970).

In addition, in order to analyze the production of heme, 1 mL of a sample was collected from each culture medium and centrifuged, and the collected cells were resuspended in 500 μL of 1 M NaOH aqueous solution and lysed by ultrasonic disruption. The prepared samples were filtered, and then the concentrations of heme therein were measured by a previously known method using HPLC (Lee et al., *J. Microbiol. Biotechnol.* 22, 1653-1658, 2012).

As a result, the production of heme in the HEME3 strain was increased to 3.79 mg/L, compared to the HEME2 strain (0.53 mg/L) (FIGS. 2 (diagram (d) and 3). In other words, the production of heme could be increased by regulating the expression levels of the genes of the heme biosynthetic pathway.

Example 3: Deletion of Competitive Metabolic Pathways for Increased Production of Heme For increased production of heme, metabolic pathways competing with the heme biosynthetic pathway can be deleted. First, to increase the metabolic flux from glucose to glutamate, metabolites of glycolysis that serve as precursors of C5 ALA biosynthesis can be prevented from being converted to by-products such as acetate or lactate. In addition, the produced heme can be prevented from being degraded, thereby increasing the production of heme.

3-1: Deletion of ldhA and Pta Genes for Increased Production of Heme

In order to increase the yield and metabolism for conversion of glucose to glutamate in the strain of the present invention that uses the C5 ALA biosynthetic pathway, pyruvate and acetyl-CoA, which are metabolites of glycolysis, need to be prevented from being converted to lactate and acetate, respectively. Based on a previous report indicating that the production of glutamate can be increased by deleting the ldhA gene involved in the conversion of pyruvate to lactate and the pta gene involved in the conversion of acetyl-CoA to acetate (Vuoristo et al., *AMB Express* 5, 61, 2015), the ldhA and pta genes were deleted from HEME3 through the following procedures.

(a) Construction of DNA Fragments for Gene Deletion

To delete the ldhA and pta genes using a previously reported λ Red recombineering technique (Datsenko et al., *Proc. Natl. Acad. Sci. USA* 97, 6640-6645, 2000), DNA fragments required for gene deletion were constructed. A DNA fragment (ΔldhA::cat) to be used to delete the ldhA gene from the plasmid pECmulox (Kim et al., *FEMS Microbiol. Lett.* 278, 78-85, 2008) and a DNA fragment (Δpta::cat) to be used to delete the pta gene were amplified using the primers of SEQ ID NOs: 52 and 53 and the primers of SEQ ID NOs: 54 and 55, respectively.

TABLE 15

| SEQ ID NOs | Nucleotides |
|---|---|
| SEQ ID NO: 52 | 5'-TATTTTTAGT AGCTTAAATG TGATTCAACA TCACTGGAGA AAGTCTTATG TAGGTGACAC TATAGAACGC G-3' |
| SEQ ID NO: 53 | 5'-CTCCCCTGGG TTGCAGGGGA GCGGCAAGAT TAAACCAGTT CGTTCGGGCA TAGTGGATCT GATGGGTACC-3' |
| SEQ ID NO: 54 | 5'-GCTGTTTGT AACCCGCCAA ATCGGCGGTA ACGAAAGAGG ATAAACCGTG TAGGTGACAC TATAGAACGC G-3' |
| SEQ ID NO: 55 | 5'-GCAGCGCAAA GCTGCGGATG ATGACGAGAT TACTGCTGCT GTGCAGACTG TAGTGGATCT GATGGGTACC-3' |

(b) Deletion of ldhA Gene from BL21(DE3)

In order to delete the ldhA gene using the above-constructed DNA fragment, the plasmid pKD46 (Datsenko et al., *Proc. Natl. Acad. Sci. USA* 97, 6640-6645, 2000) was introduced into the BL21(DE3) strain which was then inoculated into 5 mL of LB medium (10 g/L NaCl, 10 g/L tryptone, 5 g/L yeast extract) containing 50 μg/mL ampicillin, and was cultured overnight at 30° C. and 200 rpm. The cultured cells in 1 mL of the culture broth were used to inoculate 100 mL of LB medium supplemented with 50 μg/mL of ampicillin and 1 mM of arabinose, and were then cultured at 30° C. and 200 rpm until the $OD_{600}$ reached about 0.6. The cultured cells were harvested, washed twice with 10% glycerol cooled to 0° C., and were then resuspended in 150 μL of the same aqueous solution. Next, the constructed DNA fragment (ΔldhA::cat) for deletion of the ldhA gene was introduced into the cells by electroporation, and then a colony introduced with chloramphenicol resistance gene (cat) while lacking the ldhA gene was selected by culture on LB-agar medium (10 g/L NaCl, 10 g/L tryptone, 5 g/L yeast extract, 15 g/L agar) containing 8.5 μg/mL of chloramphenicol at 37° C.

After removal of the plasmid pKD46 from the selected colonies during the culture at 37° C. for colony selection was confirmed, the plasmid pJW168 (Wild et al., *Gene* 223, 55-66, 1998) was introduced again into the colony which was then cultured on LB-agar medium (10 g/L NaCl, 10 g/L tryptone, 5 g/L yeast extract, 15 g/L agar) containing 50 μg/mL of ampicillin and 1 mM IPTG at 30° C., thereby removing the chloramphenicol resistance gene (cat). Deletion of the ldhA gene from the constructed strain BL21 (DE3) ΔldhA (Table 16) was confirmed by sequencing.

TABLE 16

| Strain | Description |
|---|---|
| Bl21(DE3) ΔldhA | *E. coli* BL21(DE3) ΔldhA |

(c) Deletion of Pta Gene from BL21(DE3) ΔldhA

In order to delete the pta gene using the above-constructed DNA fragment, the plasmid pKD46 (Datsenko et al., *Proc. Natl. Acad. Sci. USA* 97, 6640-6645, 2000) was introduced into the BL21(DE3) strain which was then used to inoculate 5 mL of LB medium (10 g/L NaCl, 10 g/L tryptone, 5 g/L yeast extract) containing 50 μg/mL ampicillin, and was cultured overnight at 30° C. and 200 rpm. The cultured cells in 1 mL of the culture broth were transferred to 100 mL of LB medium supplemented with 50 μg/mL of ampicillin and 1 mM of arabinose, and were then cultured at 30° C. and 200 rpm until the $OD_{600}$ reached about 0.6. The cultured cells were harvested, washed twice with 10% glycerol cooled to 0° C., and were then resuspended in 150 μL of the same aqueous solution. Next, the constructed DNA fragment (Δpta::cat) for deletion of the pta gene was introduced into the cells by electroporation, and then a colony introduced with chloramphenicol resistance gene (cat) while lacking the pta gene was selected by culture on LB-agar medium (10 g/L NaCl, 10 g/L tryptone, 5 g/L yeast extract, 15 g/L agar) containing 8.5 μg/mL of chloramphenicol at 37° C.

After removal of the plasmid pKD46 from the selected colonies during the culture at 37° C. for colony selection was confirmed, the plasmid pJW168 (Wild et al., *Gene* 223, 55-66, 1998) was introduced again into the colony which was then cultured on LB-agar medium (10 g/L NaCl, 10 g/L tryptone, 5 g/L yeast extract, 15 g/L agar) containing 50 μg/mL of ampicillin and 1 mM IPTG at 30° C., thereby removing the chloramphenicol resistance gene (cat). Deletion of the pta gene from the constructed strain BL21(DE3) Δpta ΔldhA was confirmed by sequencing.

TABLE 17

| Strain | Description |
| --- | --- |
| Bl21(DE3) Δpta ΔldhA | E. coli BL21(DE3) Δpta ΔldhA |

(d) Construction of Recombinant E. coli HEME5

The pCDF-hemAL, pRSF-hemBCD and pET-hemEFGH plasmids constructed in Example 2-2 were introduced together into the strain BL21(DE3) Δpta ΔldhA shown in Table 17, thereby constructing an E. coli HEME5 strain (Table 18).

TABLE 18

| Strain | Description |
| --- | --- |
| HEME5 | E. coli BL21(DE3) Δpta ΔldhA harboring pCDF-hemAL, pRSF-hemBCD, and pET-hemEFGH |

In order to identify the profiles of ALA and heme production in the constructed E. coli strain, the strain shown in Table 18 above was used to inoculate 5 mL of LB medium (10 g/L NaCl, 10 g/L tryptone, 5 g/L yeast extract) containing 25 μg/mL of kanamycin, 50 μg/mL of ampicillin, and 100 μg/mL streptomycin, and was then cultured at 37° C. and 220 rpm for 12 hours. For main culture for heme production, 1 mL of the pre-culture was transferred to 50 mL of LB-Fe7.5 medium (10 g/L NaCl, 10 g/L tryptone, 5 g/L yeast extract, 7.5 mg/L FeSO$_4$7H$_2$O) containing the same antibiotics, and then the cells were cultured in a 250-mL Erlenmeyer flask at 37° C. and 200 rpm until the OD$_{600}$ reached about 0.6. Next, 1 mM IPTG was added to the culture medium, and then the cells were cultured at 30° C. and 200 rpm for 48 hours.

After the culture, samples were collected to analyze the production of ALA, and then the samples were pretreated and analyzed by a previously reported method (Burnham, *Methods Enzymol.* 17A, 195-204, 1970).

In addition, in order to analyze the production of heme, 1 mL of a sample was collected from each culture medium and centrifuged, and the collected cells were resuspended in 500 μL of 1 M NaOH aqueous solution and lysed by ultrasonic disruption. The prepared samples were filtered, and then the concentrations of heme therein were measured by a previously known method using HPLC (Lee et al., *J. Microbiol. Biotechnol.* 22, 1653-1658, 2012).

As a result, the production of heme in the HEME5 strain was increased to 4.17 mg/L, compared to the HEME3 strain (3.79 mg/L) (FIG. 3).

3-2: Deletion of yfeX Gene for Increased Production of Heme

A previous study reported that the protein expressed from the yfeX gene is heme dechelatase that removes $Fe^{2+}$ ions from heme (Letoffe et al., *Proc. Natl. Acad. Sci. USA* 106, 11719-11724, 2009), but another study reported that the expression product of the yfeX gene is not heme dechelatase, but peroxidase that converts porphyrinogen to porphyrin (Dailey et al., *mBio* 2, e00248-00211, 2011). However, still another study reported that overexpression of the yfeX gene disrupts the homeostasis of heme (Turlin et al., *Microbiology Open* 3, 849-859, 2014). Although the exact function of the yfeX gene has not yet been found, it was considered that deletion of the yfeX gene can increase the production of heme. Thus, the effect of deleting the yfeX gene on the production of heme was examined through the following procedures.

(a) Construction of DNA Fragments for Gene Deletion

To delete the yfeX gene using a previously reported λ Red recombineering technique (Datsenko et al., *Proc. Natl. Acad. Sci. USA* 97, 6640-6645, 2000), DNA fragments required for gene deletion were constructed. A DNA fragment (ΔyfeX::cat) to be used to delete the yfeX gene was amplified from the plasmid pECmulox (Kim et al., *FEMS Microbiol. Lett.* 278, 78-85, 2008) using the primers of SEQ ID NOs: 56 and 57.

TABLE 19

| SEQ ID NOs | Nucleotide sequences |
| --- | --- |
| SEQ ID NO: 56 | 5'-TCAACAATGC CACGGATTGC GTGGCATTCT TATTTTCAGG AGGAACAATG TAGGTGACAC TATAGAACGC G-3' |
| SEQ ID NO: 57 | 5'-CTGGCCTTTA ATCAATGAAT CAGAAACGCT TACAGCGCCA TCAACTTGTC TAGTGGATCT GATGGGTACC-3' |

(b) Deletion of yfeX Gene from BL21(DE3)

In order to delete the yfeX gene using the above-constructed DNA fragment, the plasmid pKD46 (Datsenko et al., *Proc. Natl. Acad. Sci. USA* 97, 6640-6645, 2000) was introduced into the BL21(DE3) strain which was then used to inoculate 5 mL of LB medium (10 g/L NaCl, 10 g/L tryptone, 5 g/L yeast extract) containing 50 μg/mL ampicillin, and was cultured overnight at 30° C. and 200 rpm. The cultured cells in 1 mL of the culture broth were transferred to 100 mL of LB medium supplemented with 50 μg/mL of ampicillin and 1 mM of arabinose, and were then cultured at 30° C. and 200 rpm until the OD$_{600}$ reached about 0.6. The cultured cells were harvested, washed twice with 10% glycerol cooled to 0° C., and were then resuspended in 150 μL of the same aqueous solution. Next, the constructed DNA fragment (ΔyfeX::cat) for deletion of the yfeX gene was introduced into the cells by electroporation, and then a colony introduced with chloramphenicol resistance gene (cat) while lacking the yfeX gene was selected by culture on LB-agar medium (10 g/L NaCl, 10 g/L tryptone, 5 g/L yeast extract, 15 g/L agar) containing 8.5 μg/mL of chloramphenicol at 37° C.

After removal of the plasmid pKD46 from the selected colonies during culture at 37° C. for colony selection was confirmed, the plasmid pJW168 (Wild et al., *Gene* 223, 55-66, 1998) was introduced again into the colony which was then cultured on LB-agar medium (10 g/L NaCl, 10 g/L tryptone, 5 g/L yeast extract, 15 g/L agar) containing 50 μg/mL of ampicillin and 1 mM IPTG at 30° C., thereby removing the chloramphenicol resistance gene (cat). Deletion of the yfeX gene from the constructed strain BL21 (DE3) ΔyfeX (table 20) was confirmed by sequencing.

TABLE 20

| Strain | Description |
| --- | --- |
| Bl21(DE3) ΔyfeX | E. coli BL21(DE3) ΔyfeX |

(c) Construction of Recombinant *E. coli* HEME4

The pCDF-hemAL, pRSF-hemBCD and pET-hemEFGH plasmids constructed in Example 2-2 were introduced together into the strain BL21(DE3) ΔyfeX shown in Table 20, thereby constructing an *E. coli* HEME4 strain (Table 21).

TABLE 21

| Strain | Description |
| --- | --- |
| HEME4 | *E. coli* BL21(DE3) ΔyfeX harboring pCDF-hemAL, pRSF-hemBCD, and pET-hemEFGH |

In order to identify the profiles of ALA and heme production in the constructed *E. coli* strains, the strain shown in Table 21 above was used to inoculate 5 mL of LB medium (10 g/L NaCl, 10 g/L tryptone, 5 g/L yeast extract) containing 25 µg/mL of kanamycin, 50 µg/mL of ampicillin, and 100 µg/mL streptomycin, and was then cultured at 37° C. and 220 rpm for 12 hours. For main culture for heme production, 1 mL of the pre-culture was transferred to 50 mL of LB-Fe7.5 medium (10 g/L NaCl, 10 g/L tryptone, 5 g/L yeast extract, 7.5 mg/L FeSO$_4$7H$_2$O) containing the same antibiotics, and then the cells were cultured in a 250-mL Erlenmeyer flask at 37° C. and 200 rpm until the OD$_{600}$ reached about 0.6. Next, 1 mM IPTG was added to the culture medium, and then the cells were cultured at 30° C. and 200 rpm for 48 hours.

After the culture, samples were collected to analyze the production of ALA, and then the samples were pretreated and analyzed by a previously reported method (Burnham, *Methods Enzymol.* 17A, 195-204, 1970).

In addition, in order to analyze the production of heme, 1 mL of a sample was collected from each culture medium and centrifuged, and the collected cells were resuspended in 500 µL of 1 M NaOH aqueous solution and lysed by ultrasonic disruption. The prepared samples were filtered, and then the concentrations of heme therein were measured by a previously known method using HPLC (Lee et al., *J. Microbiol. Biotechnol.* 22, 1653-1658, 2012).

As a result, the production of heme in the HEME4 strain was increased to 6.21 mg/L, compared to the HEME3 strain (3.79 mg/L) (FIG. 3).

3-3: Deletion of Pta, ldhA and yfeX Genes for Increased Production of Heme

As described in Examples 3-1 and 3-2, the production of heme in each of the HEME5 strain (4.17 mg/mL heme) lacking the pta and ldhA genes and the HEME4 strain (6.21 mg/mL heme) lacking the yfeX gene was increased compared to that in the HEME3 strain (3.79 mg/L). Thus, in order to examine whether the production of heme can further be increased when the gene deletion strategies of Examples 3-1 and Example 3-2 are used together, a strain lacking all the three genes was constructed and analyzed through the following procedures.

(a) Construction of DNA Fragments for Gene Deletion

To delete the yfeX gene using a previously reported A Red recombineering technique (Datsenko et al., *Proc. Natl. Acad. Sci. USA* 97, 6640-6645, 2000), DNA fragments required for gene deletion were constructed. A DNA fragment (ΔyfeX::cat) to be used to delete the yfeX gene was amplified from the plasmid pECmulox (Kim et al., *FEMS Microbiol. Lett.* 278, 78-85, 2008) using the primers of SEQ ID NOs: 56 and 57.

(b) Deletion of yfeX Gene from BL21(DE3) ΔPL

In order to delete the yfeX gene using the above-constructed DNA fragment, the plasmid pKD46 (Datsenko et al., *Proc. Natl. Acad. Sci. USA* 97, 6640-6645, 2000) was introduced into the BL21(DE3) APL strain which was then used to inoculate 5 mL of LB medium (10 g/L NaCl, 10 g/L tryptone, 5 g/L yeast extract) containing 50 µg/mL ampicillin, and was cultured overnight at 30° C. and 200 rpm. The cultured cells in 1 mL of the culture broth were transferred to 100 mL of LB medium supplemented with 50 µg/mL of ampicillin and 1 mM of arabinose, and were then cultured at 30° C. and 200 rpm until the OD$_{600}$ reached about 0.6. The cultured cells were harvested, washed twice with 10% glycerol cooled to 0° C., and were then resuspended in 150 µL of the same aqueous solution. Next, the constructed DNA fragment (ΔyfeX::cat) for deletion of the yfeX gene was introduced into the cells by electroporation, and then a colony introduced with chloramphenicol resistance gene (cat) while lacking the yfeX gene was selected by culture on LB-agar medium (10 g/L NaCl, 10 g/L tryptone, 5 g/L yeast extract, 15 g/L agar) containing 8.5 µg/mL of chloramphenicol at 37° C.

After removal of the plasmid pKD46 from the selected colonies during the culture at 37° C. for colony selection was confirmed, the plasmid pJW168 (Wild et al., *Gene* 223, 55-66, 1998) was introduced again into the colony which was then cultured on LB-agar medium (10 g/L NaCl, 10 g/L tryptone, 5 g/L yeast extract, 15 g/L agar) containing 50 µg/mL of ampicillin and 1 mM IPTG at 30° C., thereby removing the chloramphenicol resistance gene (cat).

Deletion of the yfeX gene from the constructed strain BL21(DE3) Δpta ΔldhA ΔyfeX (table 22) was confirmed by sequencing.

TABLE 22

| Strain | Description |
| --- | --- |
| Bl21(DE3) Δpta ΔldhA ΔyfeX | *E. coli* BL21(DE3) Δpta ΔldhA ΔyfeX |

(c) Construction of Recombinant *E. coli* HEME6

The pCDF-hemAL, pRSF-hemBCD and pET-hemEFGH plasmids constructed in Example 2-2 were introduced together into the strain BL21(DE3) Δpta ΔldhA ΔyfeX shown in Table 22, thereby constructing an *E. coli* HEME6 strain (FIG. 2 in diagram (e) and Table 23).

TABLE 23

| Strain | Description |
| --- | --- |
| HEME6 | *E. coli* BL21(DE3) Δpta ΔldhA ΔyfeX harboring pCDF-hemAL, pRSF-hemBCD, and pET-hemEFGH |

In order to identify the profiles of production of ALA and heme in the constructed *E. coli* strains, the strain shown in Table 23 above was used to inoculate 5 mL of LB medium (10 g/L NaCl, 10 g/L tryptone, 5 g/L yeast extract) containing 25 µg/mL of kanamycin, 50 µg/mL of ampicillin, and 100 µg/mL streptomycin, and was then cultured at 37° C. and 220 rpm for 12 hours. For main culture for heme production, 1 mL of the pre-culture was transferred to 50 mL of LB-Fe7.5 medium (10 g/L NaCl, 10 g/L tryptone, 5 g/L yeast extract, 7.5 mg/L FeSO$_4$7H$_2$O) containing the same antibiotics, and then the cells were cultured in a 250-mL Erlenmeyer flask at 37° C. and 200 rpm until the OD$_{600}$ reached about 0.6. Next, 1 mM IPTG was added to the culture medium, and then the cells were cultured at 30° C. and 200 rpm for 48 hours.

After the culture, samples were collected to analyze the production of ALA, and then the samples were pretreated and analyzed by a previously reported method (Burnham, *Methods Enzymol.* 17A, 195-204, 1970).

In addition, in order to analyze the production of heme, 1 mL of a sample was collected from each culture broth and centrifuged, and the collected cells were resuspended in 500 µL of 1 M NaOH aqueous solution and lysed by ultrasonic disruption. The prepared samples were filtered, and then the concentrations of heme therein were measured by a previously known method using HPLC (Lee et al., *J. Microbiol. Biotechnol.* 22, 1653-1658, 2012).

As a result, the production of heme in the HEME6 strain was increased to 7.13 mg/L, compared to the HEME3 strain (3.79 mg/L), HEME5 strain (4.17 mg/mL) and HEME4 strain (6.21 mg/mL) (FIGS. 2 (diagram (e) and 3).

Example 4: Culture Condition Optimization for Increased Production of Heme

4-1: Optimization of Heme-Producing Medium: Selection of Basal Medium Composition To further increase the production of heme in the HEME6 strain constructed in Example 3, the composition of a medium which is used in culture of the strain was optimized. The HEME6 strain was cultured in each of LB-Fe7.5, TB-Fe7.5 and MR-Fe7.5 media obtained by adding 7.5 mg/L of $FeSO_4 7H_2O$ to LB medium (10 g/L NaCl, 10 g/L tryptone, 5 g/L yeast extract), TB medium (16.43 g/L $K_2HPO_4.3H_2O$, 2.31 g/L, $KH_2PO_4$, 4 g/L glycerol, 12 g/L tryptone, 24 g/L yeast extract) and MR-Fe0 medium (6.67 g/L $KH_2PO_4$, 4 g/L $(NH_4)_2HPO_4$, 0.8 g/L $MgSO_4 7H2O$, 0.8 g/L citric acid, 5 g/L yeast extract, 5 mL/L trace metal solution, pH7.0), respectively, and the production of heme in each of the media was measured. The composition of trace metal solution I is as follows: 0.5 M HCl, 2 g/L $CaCl_2$, 2.2 g/L $ZnSO_4 7H_2O$, 0.5 g/L $MnSO_4 4H_2O$, 1 g/L $CuSO_4 5H_2O$, 0.1 g/L $(NH_4)_6Mo_7O_{24} 4H_2O$, and 0.02 g/L $Na_2B_4O_7 10H_2O$.

In order to identify the profiles of production of heme in the HEME6 strain cultured in the medium, the strain shown in Table 23 above was used to inoculate 5 mL of LB medium (10 g/L NaCl, 10 g/L tryptone, 5 g/L yeast extract) containing 25 µg/mL of kanamycin, 50 µg/mL of ampicillin, and 100 µg/mL streptomycin, and was then cultured at 37° C. and 220 rpm for 12 hours. For main culture for heme production, 1 mL of the pre-culture was transferred to 50 mL of fresh six media supplemented with 25 µg/mL of kanamycin, 50 µg/mL of ampicillin and 100 µg/mL streptomycin, and then the cells were cultured in a 250-mL Erlenmeyer flask at 37° C. and 200 rpm until the $OD_{600}$ reached about 0.6. Next, 1 mM IPTG was added to the culture medium, and then the cells were cultured at 30° C. and 200 rpm for 48 hours.

In order to analyze the production of heme, 1 mL of a sample was collected from each culture broth and centrifuged, and the collected cells were resuspended in 500 µL of 1 M NaOH aqueous solution and lysed by ultrasonic disruption. The prepared samples were filtered, and then the concentrations of heme therein were measured by a previously known method using HPLC (Lee et al., *J. Microbiol. Biotechnol.* 22, 1653-1658, 2012).

Figure 4:
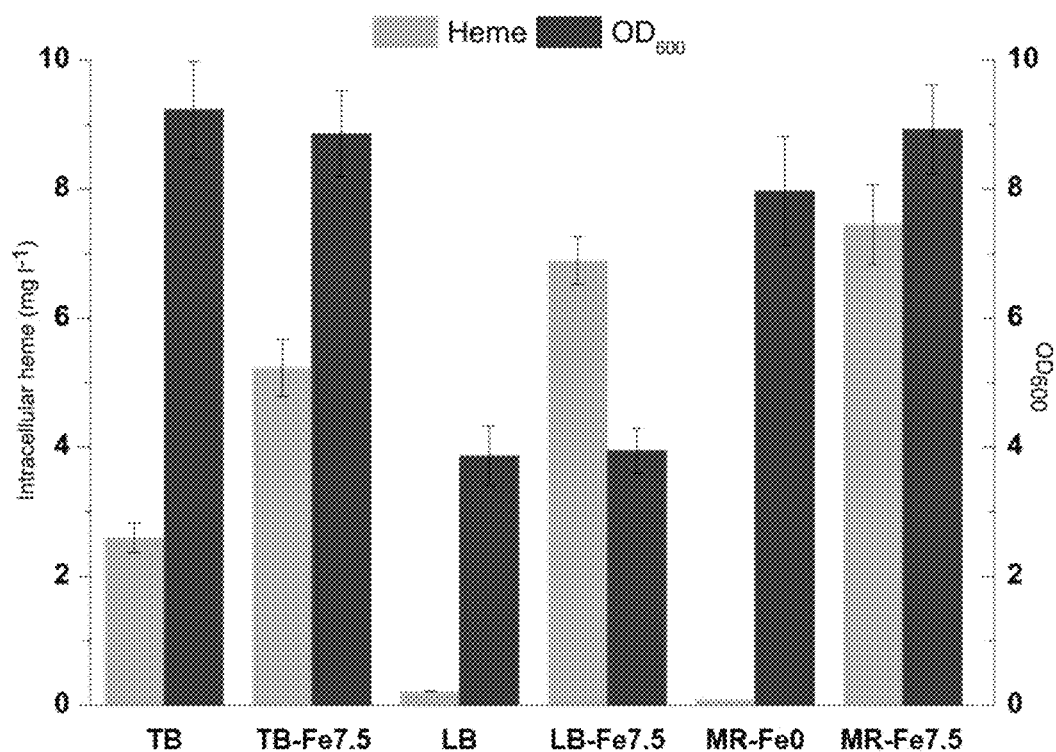
FIG. 4 shows the amounts of heme produced by flask culture of a HEME6 strain according to the present invention in TB, TB-Fe7.5, LB, LB-Fe7.5, MR-Fe0, and MR-Fe7.5 media.

As a result, it was confirmed that when the HEME6 strain was cultured in the MR-Fe7.5 medium, the largest amount of heme (7.45 mg/L) was produced (FIG. 4).

4-2: Optimization of Heme-Producing Medium: Selection of Iron Ion Concentration Based on the fact that the production of heme in the MR-Fe7.5 medium selected in Example 4-1 significantly differs from the production of heme in the MR-Fe0 medium, whether the concentration of iron ions has a great effect on the production of heme was examined. Thus, the iron ion concentration was optimized to further increase the production of heme in the HEME6 strain. Based on the MR-Fe0 medium of Example 4-1, 0, 10, 20, 40, 60 and 100 mg/L of $FeSO_4 7H_2O$ were added to the medium, thereby preparing MR-Fe0, MR-Fe10, MR-Fe20, MR-Fe40, MR-FE60 and MR-Fe100 media, respectively.

In order to identify the profiles of production of heme in the HEME6 strain cultured in the medium, the strain shown in Table 23 above was used to inoculate 5 mL of LB medium (10 g/L NaCl, 10 g/L tryptone, 5 g/L yeast extract) containing 25 µg/mL of kanamycin, 50 µg/mL of ampicillin, and 100 µg/mL streptomycin, and was then cultured at 37° C. and 220 rpm for 12 hours. For main culture for heme production, 1 mL of the pre-culture was transferred to 50 mL of fresh six media supplemented with µg/mL of kanamycin, 50 µg/mL of ampicillin and 100 µg/mL streptomycin, and then the cells were cultured in a 250-mL Erlenmeyer flask at 37° C. and 200 rpm until the $OD_{600}$ reached about 0.6. Next, 1 mM IPTG was added to the culture medium, and then the cells were cultured at 30° C. and 200 rpm for 48 hours.

In order to analyze the production of heme, 1 mL of a sample was collected from each culture medium and centrifuged, and the collected cells were resuspended in 500 µL of 1 M NaOH aqueous solution and lysed by ultrasonic disruption. The prepared samples were filtered, and then the concentrations of heme therein were measured by a previously known method using HPLC (Lee et al., *J. Microbiol. Biotechnol.* 22, 1653-1658, 2012).

Figure 5:
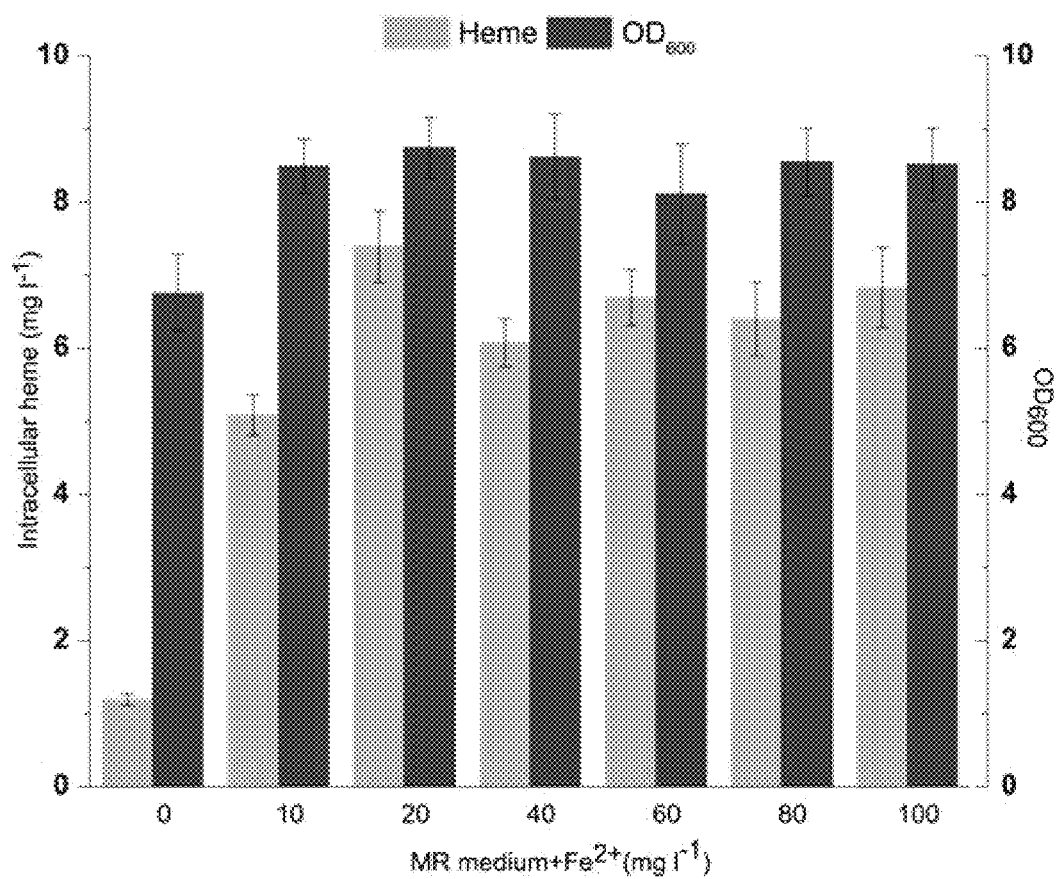
FIG. 5 shows the amounts of heme produced by flask culture of a HEME6 strain according to the present invention in media having various concentrations of $FeSO_4 \cdot 7H_2O$.

As a result, it was confirmed that when the medium contains 20 mg/L $FeSO_4 7H_2O$ (MR-Fe20 medium), the largest amount of heme was produced (FIG. 5).

4-3: Culture Temperature Optimization

To select the optimum culture temperature to be used to produce heme by the HEME6 strain, the strain was cultured through the following procedure.

The strain shown in Table 23 above was used to inoculate 5 mL of LB medium (10 g/L NaCl, 10 g/L tryptone, 5 g/L yeast extract) containing 25 µg/mL of kanamycin, 50 µg/mL of ampicillin, and 100 µg/mL streptomycin, and was then cultured at 37° C. and 220 rpm for 12 hours. For main culture for heme production, 1 mL of the pre-culture was transferred to 50 mL of fresh MR-Fe20 medium supplemented with 25 µg/mL of kanamycin, 50 µg/mL of ampicillin and 100 µg/mL streptomycin, and then the cells were cultured in a 250-mL Erlenmeyer flask at 37° C. and 200 rpm until the $OD_{600}$ reached about 0.6. Next, 1 mM IPTG was added to the culture medium, and then the cells were cultured at 24° C., 30° C. and 37° C. and 200 rpm for 72 hours, and sampling was performed at 6-hour intervals for the first 24 hours and at 12-hour intervals after the first 24 hours.

In order to analyze the production of heme, 1 mL of a sample was collected from the culture broth and centrifuged, and the collected cells were resuspended in 500 μL of 1 M NaOH aqueous solution and lysed by ultrasonic disruption. The prepared samples were filtered, and then the concentrations of heme therein were measured by a previously known method using HPLC (Lee et al., *J. Microbiol. Biotechnol.* 22, 1653-1658, 2012).

Figure 6:
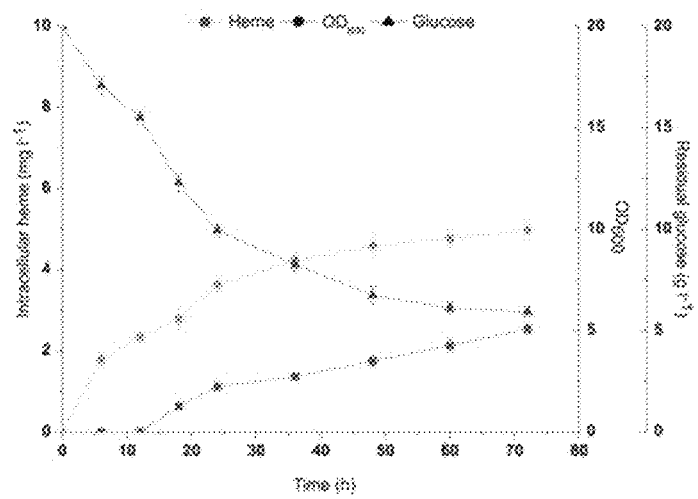
FIG. 6 shows the amounts of heme produced by flask culture of a HEME6 strain according to the present invention at various culture temperatures.
Figure 6:
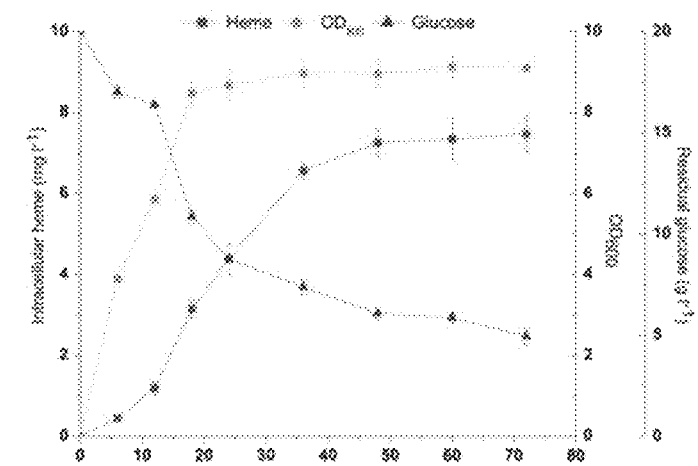
Figure 6:
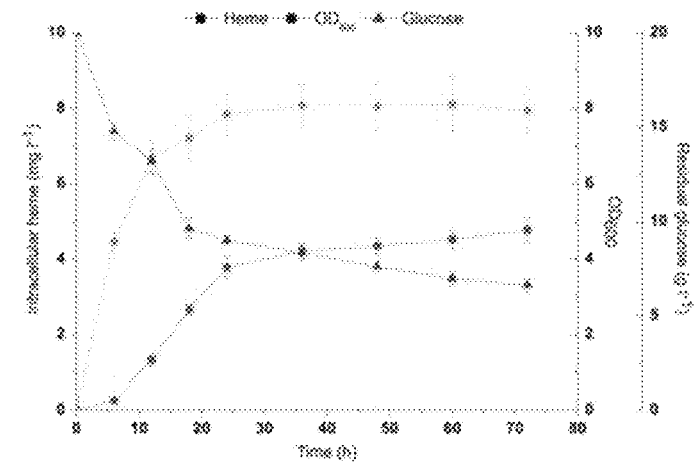

As a result, it was confirmed that when the strain was cultured in the presence of 1 mM IPTG at 30° C. for 60 hours, the largest amount of heme (7.78 g/L) was produced (FIG. 6).

Example 5: Extracellular Free Heme Production by Batch Fermentation and Fed-Batch Fermentation 5-1: Extracellular Free Heme Production by Batch Fermentation An example in which fermentation was performed using a fermenter for heme production has not been reported.

Thus, based on the culture conditions optimized in Example 4, batch fermentation was performed using the HEME6 strain.

The strain shown in Table 23 was used to inoculate 5 mL of LB medium (10 g/L NaCl, 10 g/L tryptone, 5 g/L yeast extract) supplemented with 25 μg/mL of kanamycin, 50 μg/mL of ampicillin and 100 μg/mL of streptomycin, and was then cultured at 37° C. and 220 rpm for 12 hours. For main culture for heme production, 1 mL of the pre-culture was transferred to 200 mL of fresh MR-Fe20 medium supplemented with 25 μg/mL of kanamycin, 50 of μg/mL ampicillin and 100 μg/mL of streptomycin, and then the cells were cultured in a 500-mL Erlenmeyer flask at 37° C. and 200 rpm for 12 hours. Next, the culture was transferred to a 6.6-L Bioflo3000 fermenter (New Brunswick Scientific Co., Edison, N.J.) containing 1.8 L of MR-Fe20 medium (pH7.0; air-saturated with stirring at 200 rpm and supply of 2 L/min of air at 30° C.) supplemented with 25 μg/mL of kanamycin, 50 μg/mL of ampicillin, 100 μg/mL of streptomycin and 20 g/L of glucose. During fermentation, the temperature was maintained at 30° C., and the pH was maintained at 7.0 by 50% $NH_4OH$. In addition, the dissolved oxygen (DO) level was maintained at 40% of the initial DO level by increasing the agitation speed up to 1000 rpm. When the $OD_{600}$ reached 5, 1 mM IPTG was added to the cells, and for analysis of heme production, sampling was performed at 8-hour intervals.

In order to analyze the production of heme, 1 mL of a sample was collected from the culture broth and centrifuged, and the collected cells were resuspended in 500 μL of 1 M NaOH aqueous solution and lysed by ultrasonic disruption. The prepared medium and lysed cell samples were filtered, and then the concentrations of heme therein were measured by a previously known method using HPLC (Lee et al., *J. Microbiol. Biotechnol.* 22, 1653-1658, 2012).

Figure 7:
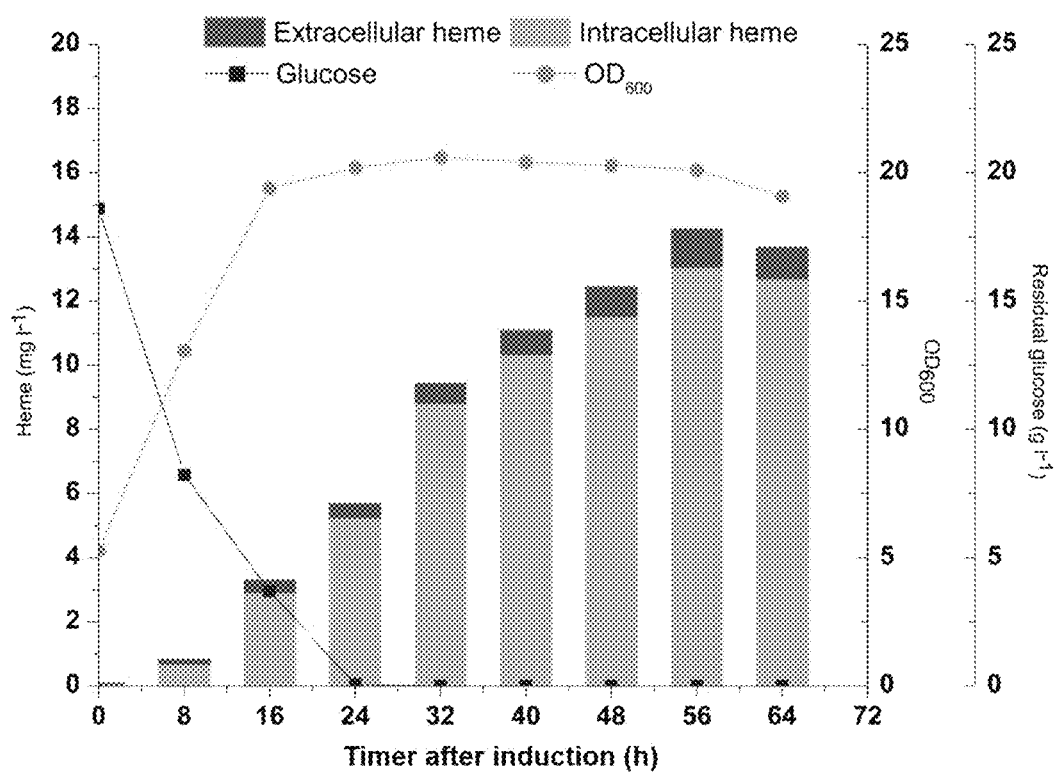
FIG. 7 shows the amounts of heme produced by batch culture of a HEME6 strain according to the present invention.

As a result, the largest amount of heme (a total of 14.24 mg/L) was produced at 56 hours, and 1.18 mg/L (8.29%) of the produced heme was detected in the medium. The overall productivity for 56 hours was 0.25 mg/L/h (FIG. 7). It is significant that 1 mg/L or more of extracellular free heme could be detected through the batch fermentation in this Example.

5-2: Extracellular Free Heme Production by Fed-Batch Fermentation

Based on the batch fermentation results obtained in Example 5-1, fed-batch fermentation was performed to produce a larger amount of heme.

The strain shown in Table 23 was used to inoculate 5 mL of LB medium (10 g/L NaCl, 10 g/L tryptone, 5 g/L yeast extract) supplemented with 25 μg/mL of kanamycin, 50 μg/mL of ampicillin and 100 μg/mL of streptomycin, and was then cultured at 37° C. and 220 rpm for 12 hours. For main culture for heme production, 1 mL of the pre-culture was transferred to 200 mL of fresh MR-Fe20 medium supplemented with 25 μg/mL of kanamycin, 50 of μg/mL ampicillin and 100 μg/mL of streptomycin, and then the cells were cultured in a 500-mL Erlenmeyer flask at 37° C. and 200 rpm for 12 hours. Next, the culture was transferred to a 6.6-L Bioflo3000 fermenter (New Brunswick Scientific Co., Edison, N.J.) containing 1.8 L of MR-Fe20 medium (pH7.0; air-saturated with stirring at 200 rpm and supply of 2 L/min of air at 30° C.) supplemented with 25 μg/mL of kanamycin, 50 μg/mL of ampicillin, 100 μg/mL of streptomycin and 20 g/L of glucose. During fermentation, the temperature was maintained at 30° C., and the pH was maintained at 7.0 by 50% $NH_4OH$. In addition, the dissolved oxygen (DO) level of was maintained at 40% of the initial DO level by increasing the agitation speed up to 1000 rpm. During the fed-batch fermentation, a feeding solution (700 g/L glucose, 8 g/L $MgSO_4 7H_2O$, 20 mg/L $FeSO_4 7H_2O$) was supplied using a pH-stat method. When the $OD_{600}$ reached 5, 1 mM IPTG was added to the culture medium, and for analysis of heme production, sampling was performed at 8-hour intervals.

In order to analyze the production of heme, 1 mL of a sample was collected from the culture medium and centrifuged, and the collected cells were resuspended in 500 μL of 1 M NaOH aqueous solution and lysed by ultrasonic disruption. The prepared medium and lysed cell samples were filtered, and then the concentrations of heme therein were measured by a previously known method using HPLC (Lee et al., *J. Microbiol. Biotechnol.* 22, 1653-1658, 2012).

Figure 8:
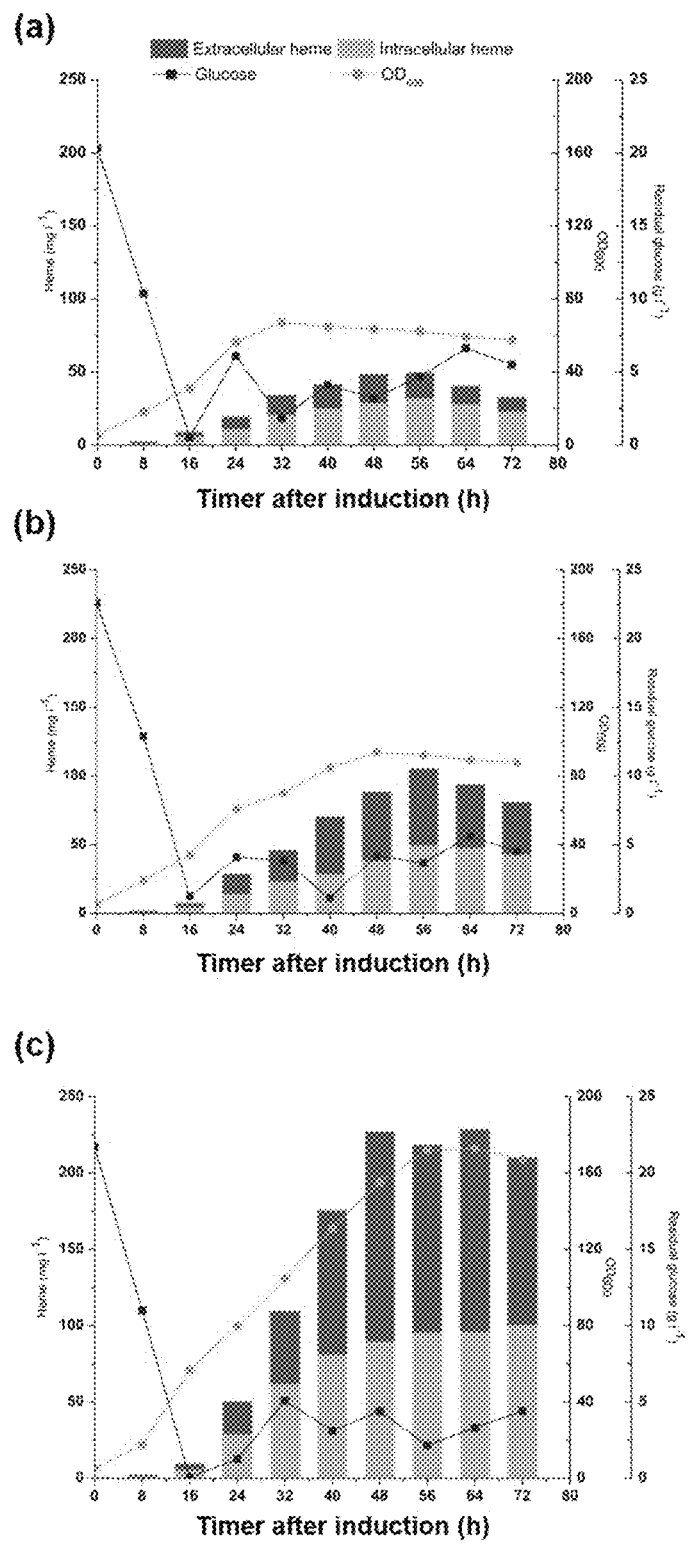
FIG. 8 shows the amount of heme produced by fed-batch culture of a HEME6 strain according to the present invention while changing the components introduced during the culture as follows: (a) 700 g/L glucose, 8 g/L $MgSO_4 \cdot 7H_2O$, 20 mg/L $FeSO_4 \cdot 7H_2O$; (b) 700 g/L glucose, 8 g/L $MgSO_4 \cdot 7H_2O$, 20 mg/L $FeSO_4 \cdot 7H_2O$, 5 g/L $(NH_4)_2SO_4$; and (c) 700 g/L glucose, 8 g/L $MgSO_4 \cdot 7H_2O$, 20 mg/L $FeSO_4 \cdot 7H_2O$, 20 g/L 1-glutamate.

As a result, the largest amount of heme (a total of 49.18 mg/L) was produced at 56 hours, and 16.77 mg/L (34.10%) of the produced heme was detected in the medium. The $OD_{600}$ reached the maximum value (67.2) at 32 hours (FIG. 8 in graph (a)).

5-3: Extracellular Free Heme Production by Fed-Batch Fermentation of Strain Supplied with $(NH_4)_2SO_4$ Based on the fact that 4 nitrogen atoms are required to produce one molecule of heme, it was concluded that the production of heme can be increased by supplying a nitrogen source. To verify the hypothesis, fed-hatch fermentation was performed while supplying $(NH_4)_2SO_4$ as a nitrogen source.

The strain shown in Table 23 was inoculated into 5 mL of LB medium (10 g/L NaCl, 10 g/L tryptone, 5 g/L yeast extract) supplemented with 25 μg/mL of kanamycin, 50 μg/mL of ampicillin and 100 μg/mL of streptomycin, and was then cultured at 37° C. and 220 rpm for 12 hours. For main culture for heme production, 1 mL of the medium in which the cultured cells were growing was inoculated into 200 mL of fresh MR-Fe20 medium supplemented with 25 μg/mL of kanamycin, 50 of μg/mL ampicillin and 100 μg/mL of streptomycin, and then the cells were cultured in a 500-mL Erlenmeyer flask at 37° C. and 200 rpm for 12 hours. Next, the culture was inoculated into a 6.6-L Bioflo3000 fermenter (New Brunswick Scientific Co., Edison, N.J.) containing 1.8 L of MR-Fe20 medium (pH7.0; air-saturated with stirring at 200 rpm and supply of 2 L/min of air at 30° C.) supplemented with 25 μg/mL of kanamycin, 50 μg/mL of ampicillin, 100 μg/mL of streptomycin and 20 g/L of glucose. During fermentation, the temperature was maintained at 30° C., and the pH was maintained at 7.0 by 50% NH$_4$OH. In addition, the dissolved oxygen (DO) level was maintained at 40% of the initial DO level by increasing the agitation speed up to 1000 rpm. During the fed-batch fermentation, a feeding solution (700 g/L glucose, 8 g/L MgSO$_4$7H$_2$O, 20 mg/L FeSO$_4$7H$_2$O) was supplied using a pH-stat method. When the OD$_{600}$ reached 5, 1 mM IPTG was added to the culture medium, and for analysis of heme production, sampling was performed at 8-hour intervals. In order to analyze the production of heme, 1 mL of a sample was collected from the culture medium and centrifuged, and the collected cells were resuspended in 500 μL of 1 M NaOH aqueous solution and lysed by ultrasonic disruption. The prepared medium and lysed cell samples were filtered, and then the concentrations of heme therein were measured by a previously known method using HPLC (Lee et al., *J. Microbiol. Biotechnol.* 22, 1653-1658, 2012).

As a result, the largest amount of heme (a total of 104.90 mg/L) was produced at 56 hours, and 54.61 mg/L (52.06%) of the produced heme was detected in the medium. The OD$_{600}$ reached the maximum value (93.8) at 48 hours (FIG. 8 in graph (b)).

5-4: Extracellular Free Heme Production by Fed-Batch Fermentation of Strain Supplied with Glutamate The HEME6 strain constructed in the present invention has the advantage of showing the world's highest heme production without supplying ALA production precursors as proven in the above Examples. Glutamate, precursor of the C5 ALA biosynthetic pathway, is relatively inexpensive and shows no cytotoxicity, unlike glycine, precursor of the C4 ALA biosynthetic pathway, which is relatively expensive and cytotoxic. Therefore, in order to examine the maximum heme-producing capacity of the HEME6 strain constructed in the present invention, fed-batch fermentation was performed while supplying glutamate as a nitrogen source.

The strain shown in Table 23 was used to inoculate 5 mL of LB medium (10 g/L NaCl, 10 g/L tryptone, 5 g/L yeast extract) supplemented with 25 μg/mL of kanamycin, 50 μg/mL of ampicillin and 100 μg/mL of streptomycin, and was then cultured at 37° C. and 220 rpm for 12 hours. For main culture for heme production, 1 mL of the pre-culture was transferred to 200 mL of fresh MR-Fe20 medium supplemented with 25 μg/mL of kanamycin, 50 of μg/mL ampicillin and 100 μg/mL of streptomycin, and then the cells were cultured in a 500-mL Erlenmeyer flask at 37° C. and 200 rpm for 12 hours. Next, the culture was inoculated into a 6.6-L Bioflo3000 fermenter (New Brunswick Scientific Co., Edison, N.J.) containing 1.8 L of MR-Fe20 medium (pH7.0; air-saturated with stirring at 200 rpm and supply of 2 L/min of air at 30° C.) supplemented with 25 μg/mL of kanamycin, 50 μg/mL of ampicillin, 100 μg/mL of streptomycin and 20 g/L of glucose. During fermentation, the temperature was maintained at 30° C., and the pH was maintained at 7.0 by 50% NH$_4$OH. In addition, the dissolved oxygen (DO) level was maintained at 40% of the initial DO level by increasing the agitation speed up to 1000 rpm. During the fed-batch fermentation, a feeding solution (700 g/L glucose, 8 g/L MgSO$_4$7H$_2$O, 20 mg/L FeSO$_4$7H$_2$O, 20 g/L glutamate) was supplied using a pH-stat method. When the OD$_{600}$ reached 5, 1 mM IPTG was added to the culture medium, and for analysis of heme production, sampling was performed at 8-hour intervals.

In order to analyze the production of heme, 1 mL of a sample was collected from the culture medium and centrifuged, and the collected cells were resuspended in 500 μL of 1 M NaOH aqueous solution and lysed by ultrasonic disruption. The prepared medium and lysed cell samples were filtered, and then the concentrations of heme therein were measured by a previously known method using HPLC (Lee et al., *J. Microbiol. Biotechnol.* 22, 1653-1658, 2012).

As a result, the largest amount of heme (a total of 228.46 mg/L) was produced at 64 hours, and 131.90 mg/L (57.734%) of the produced heme was detected in the medium. The OD$_{600}$ reached the maximum value (172.8) at 48 hours (FIG. 8 in graph (c)).

Example 6: Increased Production of Heme and Promotion of Extracellular Secretion of Heme by Overexpression of Heme Exporter 6-1: Construction of Strain Overexpressing Heme Exporter Gene=ABC In Example 5, it could be confirmed that as the total production of heme increased, the proportion of extracellularly secreted heme increased gradually. This supports the hypothesis postulated prior to the start of the present invention that when cytotoxic heme (Anzaldi et al., *Infect. Immun.* 78, 4977-4989, 2010) is overproduced, extracellular heme secretion by the heme exporter CcmABC (Schulz et al., *Proc. Natl. Acad. Sci. USA* 96, 6462-6467, 1999) can be promoted to secrete free heme to the extracellular space. In addition, it was concluded that when the ccmABC genes are overexpressed in the same context, the extracellular secretion of heme can further be promoted. Thus, a strain overexpressing the ccmABC genes was constructed through the following procedure.

(a) Construction of Plasmid pACYC-ccmABC

The plasmid pACYC-ccmABC was constructed which overexpresses the heme exporter-encoding ccmA gene (SEQ ID NO: 58), ccmB gene (SEQ ID NO: 59) and ccmC gene (SEQ ID NO: 60) through the following procedures.

The primers of SEQ ID NOs: 61 and 62, the primers of SEQ ID NOs: 63 and 64, and the primers of SEQ ID NOs: 65 and 66 were respectively used to amplify the ccmA, ccmB and ccmC genes from the genomic DNA of the *E. coli* BL21(DE3) strain.

At this time, the sequence of a ribosome binding site (RBS) was added to the 5' end of the amplified ccmC gene by the sequence of the ribosome binding site (RBS) contained in the primer of SEQ ID NO: 65 used in the amplification process.

TABLE 24

| SEQ ID NOs | Nucleotide sequences |
|---|---|
| SEQ ID NO: 61 | 5'-GGGAATTCCA TATGGGTATG CTTGAAGCCA GAGAGTT-3' |
| SEQ ID NO: 62 | 5'-CCGCTCGAGT CATGCGGCCC TCGTTT-3' |
| SEQ ID NO: 63 | 5'-CATGCCATGG TGTTCTGGCG CATT-3' |
| SEQ ID NO: 64 | 5'-CGCGGATCCT TATTGAATGC TGATTCGTAA C-3' |

TABLE 24-continued

| SEQ ID NOs | Nucleotide sequences |
|---|---|
| SEQ ID NO: 65 | 5'-CCGGAATTCA TAAAAGGAGG AAAATATATG TGGAAAACAC TGCATCAAC-3' |
| SEQ ID NO: 66 | 5'-ACGCGTCGAC TCATTTACGG CCTCTTTTCA G-3' |

The amplified sequences were cleaved with NcoI and BamHI, EcoRI and SalI, and NdeI and XhoI, respectively, and then sequentially inserted into a pACYCDuet-1 vector (Novagen, USA) cleaved with the same restriction enzymes, thereby constructing pACYC-ccmABC.

(b) Construction of Recombinant E. coli HEME7

The constructed pACYC-ccmABC plasmid was introduced together into the HEME6 strain shown in Table 23, thereby constructing E. coli HEME7 strain (Table 25).

TABLE 25

| Strain | Description |
|---|---|
| HEME7 | E. coli BL21(DE3) harboring pCDF-hemAL, pRSF-hemBCD, pET-hemEFGH and pACYC-ccmABC |

6-2: Extracellular Free Heme Production by Fed-Batch Fermentation of HEME7 Strain Supplied with $(NH_4)_2SO_4$ In order to confirm the heme-producing ability of the HEME7 strain overexpressing the heme exporter genes ccmABC, constructed in Example 6-1, fed-batch fermentation was performed while supplying $(NH_4)_2SO_4$ as a nitrogen source.

The strain shown in Table 25 was used to inoculate 5 mL of LB medium (10 g/L NaCl, 10 g/L tryptone, 5 g/L yeast extract) supplemented with 25 µg/mL of kanamycin, 50 µg/mL of ampicillin, 100 µg/mL of streptomycin, and 17 µg/mL chloramphenicol, and was then cultured at 37° C. and 220 rpm for 12 hours. For main culture for heme production, 1 mL of the pre-culture was transferred to 200 mL of fresh MR-Fe20 medium supplemented with 25 µg/mL of kanamycin, 50 of µg/mL ampicillin, 100 µg/mL of streptomycin, and 17 µg/mL chloramphenicol and then the cells were cultured in a 500-mL Erlenmeyer flask at 37° C. and 200 rpm for 12 hours. Next, the culture was transferred to a 6.6-L Bioflo3000 fermenter (New Brunswick Scientific Co., Edison, N.J.) containing 1.8 L of MR-Fe20 medium (pH7.0; air-saturated with stirring at 200 rpm and supply of 2 L/min of air at 30° C.) supplemented with 25 µg/mL of kanamycin, 50 µg/mL of ampicillin, 100 µg/mL of streptomycin, 17 µg/mL chloramphenicol, and 20 g/L of glucose. During fermentation, the temperature was maintained at 30° C., and the pH was maintained at 7.0 by 50% $NH_4OH$. In addition, the dissolved oxygen (DO) level was maintained at 40% of the initial DO level by increasing the agitation speed up to 1000 rpm. During the fed-batch fermentation, a feeding solution (700 g/L glucose, 8 g/L $MgSO_4 7H_2O$, 20 mg/L $FeSO_4 7H_2O$, 5 g/L $(NH_4)$ 2504) was supplied using a pH-stat method. When the $OD_{600}$ reached 5, 1 mM IPTG was added to the culture medium, and for analysis of heme production, sampling was performed at 8-hour intervals to confirm the production of heme.

Figure 9:
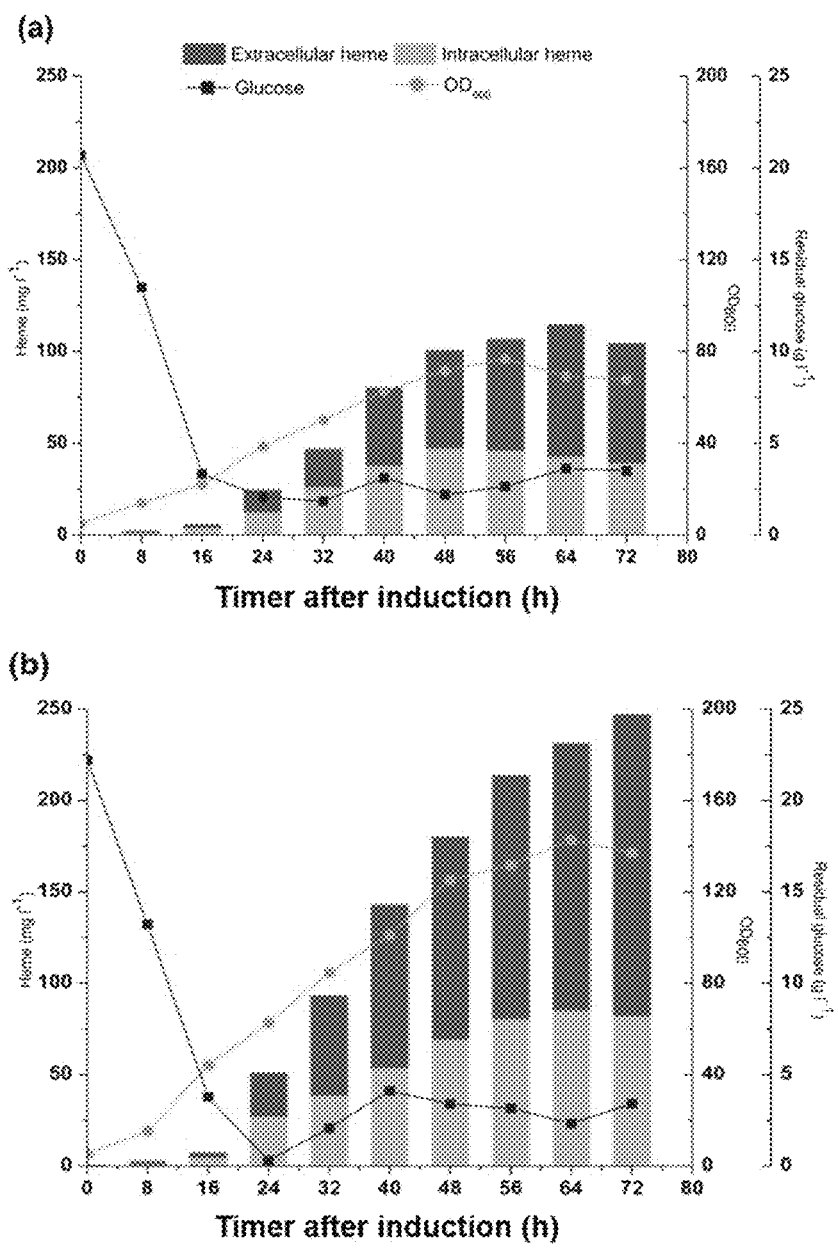
FIG. 9 shows the amount of heme produced by fed-batch culture of a HEME7 strain according to the present invention while changing the components introduced during the culture as follows: (a) 700 g/L glucose, 8 g/L $MgSO_4 \cdot 7H_2O$, 20 mg/L $FeSO_4 \cdot 7H_2O$, 5 g/L $(NH_4)_2SO_4$; and (b) 700 g/L glucose, 8 g/L $MgSO_4 \cdot 7H_2O$, 20 mg/L $FeSO_4 \cdot 7H_2O$, 20 g/L 1-glutamate.

As a result, the largest amount of heme (a total of 114.79 mg/L) was produced at 64 hours, and 71.91 mg/L (62.64%) of the produced heme was detected in the medium. The $OD_{600}$ reached the maximum value (76.9) at 56 hours (FIG. 9 in graph (a)). When the ccmABC genes were overexpressed as proposed in the hypothesis of this Example, the extracellular secretion rate of heme could be increased by 10.58% and the total production of heme could be increased by 9.89 mg/L, compared to the fed-batch fermentation results of Example 5-3.

6-3: Extracellular Free Heme Production by Fed-Batch Fermentation of HEME7 Strain Supplied with Glutamate In order to examine the highest heme production when the precursor of the C5 ALA biosynthetic pathway of the HEME7 strain overexpressing the heme exporter genes ccmABC, constructed in Example 6-1, was supplied, fed-batch fermentation was performed while supplying glutamate as a nitrogen source.

The strain shown in Table 25 was used to inoculate 5 mL of LB medium (10 g/L NaCl, 10 g/L tryptone, 5 g/L yeast extract) supplemented with 25 µg/mL of kanamycin, 50 µg/mL of ampicillin, 100 µg/mL of streptomycin, and 17 µg/mL chloramphenicol, and was then cultured at 37° C. and 220 rpm for 12 hours. For main culture for heme production, 1 mL of the pre-culture was transferred to 200 mL of fresh MR-Fe20 medium supplemented with 25 µg/mL of kanamycin, 50 of µg/mL ampicillin, 100 µg/mL of streptomycin, and 17 µg/mL chloramphenicol and then the cells were cultured in a 500-mL Erlenmeyer flask at 37° C. and 200 rpm for 12 hours. Next, the culture was transferred to a 6.6-L Bioflo3000 fermenter (New Brunswick Scientific Co., Edison, N.J.) containing 1.8 L of MR-Fe20 medium (pH7.0; air-saturated with stirring at 200 rpm and supply of 2 L/min of air at 30° C.) supplemented with 25 µg/mL of kanamycin, 50 µg/mL of ampicillin, 100 µg/mL of streptomycin, 17 µg/mL chloramphenicol, and 20 g/L of glucose. During fermentation, the temperature was maintained at 30° C., and the pH was maintained at 7.0 by 50% $NH_4OH$. In addition, the dissolved oxygen (DO) level was maintained at 40% of the initial DO level by increasing the agitation speed up to 1000 rpm. During the fed-batch fermentation, a feeding solution (700 g/L glucose, 8 g/L $MgSO_4 7H_2O$, 20 mg/L $FeSO_4 7H_2O$, 20 g/L glutamate) was supplied using a pH-stat method for continuous glucose supply. When the $OD_{600}$ reached 5, 1 mM IPTG was added to the culture medium, and for analysis of heme production, sampling was performed at 8-hour intervals to confirm the production of heme.

As a result, the largest amount of heme (a total of 246.69 mg/L) was produced at 72 hours, and 164.12 mg/L (66.529%) of the produced heme was detected in the medium. The $OD_{600}$ reached the maximum value (142.8) at 64 hours (FIG. 9b). When the ccmABC genes were overexpressed, the extracellular secretion rate of heme could be increased by 8.759% and the total production of heme could be increased by 18.23 mg/L, compared to the fed-batch fermentation results of Example 5-4.

Example 7: Production of Heme in Corynebacterium glutamicum

In order to examine whether the strategy used to develop the E. coli strain that produces and extracellularly secretes free heme may also be applied for the production of heme in other strains, the C5 ALA biosynthetic pathway was introduced into Corynebacterium glutamicum which is widely used for the production of amino acids including glutamic acid due to its proven harmlessness to the human body, and heme was produced.

C. glutamicum, an aerobic microorganism overexpressing glutamate, has the C5 biosynthetic pathway that produces ALA from glutamate and the heme biosynthetic pathway that produces heme from ALA, similar to E. coli. To overexpress the hemA and hemL genes of C. glutamicum, which correspond to the C5 biosynthetic pathway, the hemA and hemL genes were amplified from the genomic DNA of C. glutamicum ATCC 13032 using the primers of SEQ ID NOs: 67 and 68 and the primers of SEQ ID NOs: 69 and 70, respectively. In this process, two amino acids (lysine) were inserted between the second amino acid and the third amino acid of the protein expressed from the hemA gene, and thus the sequence of the hemA gene was modified such that the HemA protein would show resistance to negative feedback (HemA$^{fbr}$). The two amplified genes were cloned together into the EcoRI site of a pEKEx1 plasmid by Gibson assembly, thereby constructing a pEKEx1-hemAL plasmid which expresses the HemA$^{fbr}$ and HemL proteins when introduced into C. glutamicum.

TABLE 26

| SEQ ID NOs | Nucleotide sequences |
|---|---|
| SEQ ID NO: 67 | 5'-TGAGCGGATA CAATTTCAC ACAGGAAACA GAATTCATGG TGAGTAAGAA GGTACTCATC GTAGGGATGT CGCACA-3' |
| SEQ ID NO: 68 | 5'-GCGGATCGAG CCGTATTGGA CGATGTCATT GTTTCCTGTG TGAAATTACT CCCTCGTTTG TGTGGCAGAA-3' |
| SEQ ID NO: 69 | 5'-CACCTTCTGC CACACAAACG AGGGAGTAAT TTCACACAGG AAACAATGAC ATCGTCCAAT ACGGCTCGAT-3' |
| SEQ ID NO: 70 | 5'-GCCAAGCTTG GCTGCAGGTC GACGGATCCC CGGGAATTCT CATGATGCCT TCGCTTCTGC TGCT-3' |

In addition, in order to examine the overexpression of the hemB and hemH genes among the genes encoding the proteins involved in producing heme from ALA as shown in (a) of Example 2-1 above, a vector overexpressing the hemB and hemH genes was constructed. To this end, the hemB and hemH genes were amplified from the genomic DNA of C. glutamicum ATCC 13032 using the primers of SEQ ID NOs: 71 and 72 and the primers of SEQ ID NOs: 73 and 74, respectively. In addition, a pCES208-spc plasmid was amplified using the primers of SEQ ID NOs: 75 and 76, and then assembled with the amplified hemB and hemH genes by Gibson assembly, thereby constructing a pCES-hemBH plasmid.

TABLE 27

| SEQ ID NOs | Nucleotide sequences |
|---|---|
| SEQ ID NO: 71 | 5'-GCACCTTGGT TGGTAGGAGT AGCATGGGAT CCATGCATCA CCATCACCAT CATAGCACTT CTTCTGATTA CTCCCACG-3' |
| SEQ ID NO: 72 | 5'-TTGTTTCCTG TGTGAAATTA AGCGTTTCGC AGTGCGCGGG-3' |
| SEQ ID NO: 73 | 5'-TAATTTCACA CAGGAAACAA TGAATGAACG CACATCGGATGC-3' |

TABLE 27-continued

| SEQ ID NOs | Nucleotide sequences |
|---|---|
| SEQ ID NO: 74 | 5'-AATTATAATG GCCGGCTGGG CCTCTAGACT AGTTGGCAGC TGGCGCCGCT GA-3' |
| SEQ ID NO: 75 | 5'-TCTAGAGGCC CAGCCGGCCA TTATAATTAG-3' |
| SEQ ID NO: 76 | 5'-GGATCCCATG CTACTCCTAC CAACCAAGGT-3' |

The constructed pEKEx1-hemAL plasmid or two plasmids (pEKEx1-hemAL and pCES-hemBH) were introduced into the industrial C. glutamicum 5112 strain, thereby constructing C. glutamicum S112-AL and S112-AL-BH strains.

TABLE 28

| Strain | Description |
|---|---|
| S112-AL | C. glutamicum S112 harboring pEKEx1-hemAL |
| S112-AL-BH | C. glutamicum S112 harboring pEKEx1-hemAL and pCES-hemBH |

For flask culture for examining the heme-producing abilities of the two constructed C. glutamicum strains (S112-A1 and S112-AL-BH), each of the strains was used to inoculate 10 mL of a seed medium having the composition of Table 29 below, contained in a 250-mL baffled flask, and was then cultured at 30° C. and 200 rpm for about 12 hours until the OD$_{600}$ reached 20.

TABLE 29

| Component | Concentration |
|---|---|
| Glucose | 40.0 g/L |
| MgSO$_4$7H$_2$O | 0.4 g/L |
| FeSO$_4$7H$_2$O | 10.0 mg/L |
| MnSO$_4$5H$_2$O | 10.0 mg/L |
| KH$_2$PO$_4$ | 1.0 g/L |
| Urea | 4.0 g/L |
| Thiamine-HCl | 200 µg/L |
| Biotin | 50.0 µg/L |
| Soy bean hydrolysate | 55.0 mL/L |
| pH | 7.0 |

Next, 100 µL of the culture was inoculated into 10 mL of a main culture medium having the composition of Table 30 below, contained in a 250-mL baffled flask, and was then cultured at 30° C. and 200 rpm for 48 hours.

TABLE 30

| Component | Concentration |
|---|---|
| Glucose | 70.0 g/L |
| MgSO$_4$7H$_2$O | 0.4 g/L |
| FeSO$_4$7H$_2$O | 10.0 mg/L |
| MnSO$_4$5H$_2$O | 10.0 mg/L |
| (NH$_4$)$_2$SO$_4$ | 30.0 g/L |
| KH$_2$PO$_4$ | 1.0 g/L |
| Thiamine-HCl | 200 µg/L |
| Biotin | 50.0 µg/L |
| Soy bean hydrolysate | 55.0 mL/L |
| CaCO$_3$ | 50.0 g/L |
| pH | 8.0 |

As a result, it was confirmed that in C. glutamicum 5112 that does not overexpress the heme biosynthesis-related genes, heme was not produced, whereas, in the S112-AL and S112-AL-BH strains, heme accumulated in the cells in amounts of 0.77±0.23 and 1.64±0.30 mg/L (based on the culture volume), respectively. Therefore, it was confirmed that heme can be produced even in *C. glutamicum* by overexpressing the C5 biosynthetic pathway and the heme biosynthetic pathway.

INDUSTRIAL APPLICABILITY

According to the present invention, heme, an organometallic compound increasingly used as a health food or food supplement for the treatment of *porphyria*, can be extracellularly secreted and produced in high yield using the microorganism variant, but not conventional chemical synthesis or enzymatic synthesis, and thus a purification process required to use the produced heme can be performed in an environmentally friendly, economical and easy manner.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:

1. A metabolically engineered variant microorganism that secretes heme extracellularly, wherein the microorganism is modified by the introduction or overexpression of ccmABC genes encoding a heme exporter, wherein the microorganism comprises genes in a C5 biosynthetic pathway that produces 5-aminolevulinate (ALA) from glutamate, and genes in a pathway that synthesizes heme from ALA, wherein the genes in the C5 biosynthetic pathway comprise a gltX gene encoding glutamyl-tRNA synthase (GluRS), a hemA gene encoding glutamyl-tRNA reductase (GluTR), and a hemL gene encoding glutamate-1-semialdehyde 2,1-aminomutase (GSAM), wherein the genes in the pathway that synthesizes heme from ALA comprise a hemB gene encoding porphobilinogen synthase (PBGS), a hemC gene encoding porphobilinogen deaminase (PBGD), a hemD gene encoding uroporphyrinogen III synthase (UROS), a hemE gene encoding uroporphyrinogen III decarboxylase (UROD), a hemF gene encoding coproporphyrinogen III oxidase (CPO), a hemG gene encoding protoporphyrinogen oxidase (PPO), and a hemH gene encoding ferrochelatase (FECH), and wherein the microorganism is selected from the group consisting of *Escherichia coli*, *Bacillus* sp., *Corynebacterium* sp., *Lactobacillus* sp., *Lactococcus* sp., *Pseudomonas* sp., *Anacystis* sp., *Anabaena* sp., *Chlorobium* sp., *Chloroflexus* sp., *Clostridium* sp., Methanobacteria, *Propionibacterium* sp., *Rhodopseudomonas* sp., *Rhodobacter* sp., Rhodovulum sp., *Streptococcus* sp., *Saccharomyces* sp., *Schizosaccharomyces* sp., *Yarrowia* sp., and *Aspergillus* sp.

2. The metabolically engineered variant microorganism of claim 1, wherein the microorganism in the presence of a carbon source produces glutamic acid.

3. The metabolically engineered variant microorganism of claim 1, wherein the genes in the C5 biosynthetic pathway that produces 5-aminolevulinate (ALA) from glutamate, and the genes in the pathway that synthesizes heme from ALA, are overexpressed.

4. The metabolically engineered variant microorganism of claim 1, wherein the variant microorganism is further modified by deletion of a yfeXgene.

5. A method for producing heme comprising the steps of:
(a) culturing the metabolically engineered variant microorganism of claim 1 to produce heme; and
(b) recovering the produced heme.

6. The method of claim 5, wherein step (a) further comprises supplying a nitrogen source in the culturing.

7. A metabolically engineered variant microorganism that extracellularly secretes heme, wherein the microorganism is modified to overexpress ccmABC genes encoding a heme exporter, wherein the microorganism comprises genes in a C5 biosynthetic pathway that produces 5-aminolevulinate (ALA) from glutamate, and genes in a pathway that synthesizes heme from ALA, wherein at least one of the genes in the C5 biosynthetic pathway that produces 5-aminolevulinate (ALA) from glutamate and at least one of the genes in the pathway that synthesizes heme from ALA, are overexpressed;

wherein the genes in the C5 biosynthetic pathway comprise at least one gene selected from: a gltX gene encoding glutamyl-tRNA synthase (GluRS), a hemA gene encoding glutamyl-tRNA reductase (GluTR), and a hemL gene encoding glutamate-1-semialdehyde 2,1-aminomutase (GSAM);

wherein the genes in the pathway that synthesizes heme from ALA comprise at least one gene selected from: a hemB gene encoding porphobilinogen synthase (PBGS), a hemC gene encoding porphobilinogen deaminase (PBGD), a hemD gene encoding uroporphyrinogen III synthase (UROS), a hemE gene encoding uroporphyrinogen III decarboxylase (UROD), a hemF gene encoding coproporphyrinogen III oxidase (CPO), a hemG gene encoding protoporphyrinogen oxidase (PPO), and a hemH gene encoding ferrochelatase (FECH); and wherein the microorganism is further modified by deletion of a yfeX gene.

8. The metabolically engineered variant microorganism of claim 7, wherein the microorganism is selected from the group consisting of *Escherichia coli*, *Bacillus* sp., *Corynebacterium* sp., *Lactobacillus* sp., *Lactococcus* sp., *Pseudomonas* sp., *Anacystis* sp., *Anabaena* sp., *Chlorobium* sp., *Chloroflexus* sp., *Clostridium* sp., Methanobacteria, *Propionibacterium* sp., *Rhodopseudomonas* sp., *Rhodobacter* sp., Rhodovulum sp., *Streptococcus* sp., *Saccharomyces* sp., *Schizosaccharomyces* sp., *Yarrowia* sp., and *Aspergillus* sp.

9. The metabolically engineered variant microorganism of claim 1, wherein the microorganism is Corynebacterium glutamicum, and wherein the microorganism is modified to overexpress the hemA gene and the hemL gene in said the C5 biosynthetic pathway.

10. The metabolically engineered variant microorganism of claim 1, wherein the microorganism is Corynebacterium glutamicum, and wherein the microorganism is modified to overexpress the hemB gene and the hemH gene in the pathway that synthesizes heme from ALA.

11. The metabolically engineered variant microorganism of claim 1, wherein the microorganism is Corynebacterium glutamicum, and wherein the microorganism is modified to overexpress the hemA gene and the hemL gene in the C5 biosynthetic pathway, and to overexpress the hemB gene and the hemH gene in the pathway that synthesizes heme from ALA.

12. The metabolically engineered variant microorganism of claim 1, wherein the heme secreted extracellularly comprises free heme.

* * * * *

UNITED STATES PATENT AND TRADEMARK OFFICE
CERTIFICATE OF CORRECTION

PATENT NO. : 11,371,068 B2
APPLICATION NO. : 16/483430
DATED : June 28, 2022
INVENTOR(S) : Sang Yup Lee It is certified that error appears in the above-identified patent and that said Letters Patent is hereby corrected as shown below:

In the Specification

Column 4, Line 29, "MgSO$_4$.7H2O" should be -- MgSO$_4$·7H2O --.
Column 4, Line 30, "FeSO$_4$.7H$_2$O" should be -- FeSO$_4$·7H$_2$O --.
Column 4, Line 31, "MgSO$_4$.7H$_2$O" should be -- MgSO$_4$·7H$_2$O --.
Column 4, Line 31, "FeSO$_4$.7H$_2$O" should be -- FeSO$_4$·7H$_2$O --.
Column 4, Line 32, "MgSO$_4$.7H$_2$O" should be -- MgSO$_4$·7H$_2$O --.
Column 4, Line 33, "FeSO$_4$.7H$_2$O" should be -- FeSO$_4$·7H$_2$O --.
Column 4, Line 37, "MgSO$_4$.7H$_2$O" should be -- MgSO$_4$·7H$_2$O --.
Column 4, Line 38, "FeSO$_4$.7H$_2$O" should be -- FeSO$_4$·7H$_2$O --.
Column 4, Line 39, "MgSO$_4$.7H$_2$O" should be -- MgSO$_4$·7H$_2$O --.
Column 4, Line 39, "FeSO$_4$.7H$_2$O" should be -- FeSO$_4$·7H$_2$O --.
Column 8, Line 32, "pRSF-05" should be -- pRSF-C5 --.
Column 8, Line 35, "pRSF-05" should be -- pRSF-C5 --.
Column 9, Line 67, "pRSF-05" should be -- pRSF-C5 --.
Column 10, Line 11, "pRSF-05" should be -- pRSF-C5 --.
Column 10, Line 26, "g/L" should be -- 5 g/L --.
Column 11, Line 19, "FETES" should be -- FEMS --.
Column 14, Line 46, "diamgram" should be -- diagram --.
Column 19, Line 5, "(FIGS. 2 (diagram (d) and 3)" should be -- (FIGS. 2 (diagram (d)) and 3) --.
Column 19, Line 23, "of/dhA" should be -- of ldhA --.
Column 25, Line 20, "(FIGS. 2 (diagram (e) and 3)" should be -- (FIGS. 2 (diagram (e)) and 3) --.
Column 25, Line 35, "K$_2$HPO$_4$.3H$_2$O" should be -- K$_2$HPO$_4$·3H$_2$O --.
Column 29, Line 23, "FIG.8" should be -- FIG. 8 --.
Column 31, Line 61, "(NH$_4$) 2504)" should be -- (NH$_4$)$_2$SO$_4$) --.
Column 32, Line 54, "(FIG. 9b)" should be -- (FIG. 9 in graph (b)) --.
Column 34, Line 16, "5112" should be -- S112 --.
Column 34, Line 66, "5112" should be -- S112 --.
Column 74, Line 29, "in said the" should be -- in the --.

Signed and Sealed this
Thirteenth Day of September, 2022

*Katherine Kelly Vidal*
*Director of the United States Patent and Trademark Office*

SEQUENCE LISTING

```
<160> NUMBER OF SEQ ID NOS: 76

<210> SEQ ID NO 1
<211> LENGTH: 1224
<212> TYPE: DNA
<213> ORGANISM: Artificial Sequence
<220> FEATURE:
<223> OTHER INFORMATION: hemA-Rsp

<400> SEQUENCE: 1 atgattata acctggcact ggataccgcg ctgaatcgtc tgcataccga aggtcgttac      60
cgcacgttta ttgatatcga acgtcgcaaa ggcgccttcc cgaaagcaat gtggcgcaaa    120
ccggatggta gcgaaaaaga aattaccgtt tggtgcggca acgattatct gggtatgggc    180
cagcatccgg tggttctggg tgcgatgcac gaagccctgg atagtaccgg tgcaggcagc    240
ggcggtacgc gtaacattag cggcaccacg ctgtatcata aacgcctgga agcggaactg    300
gccgatctgc acggcaaaga agcggccctg gtgtttagct ctgcatacat cgcgaacgat    360
gccaccctga gcacgctgcc gcagctgatc ccgggtctgg tgattgttag cgataaactg    420
aaccatgcat ctatgattga aggtatccgt cgctctggca ccgaaaaaca tatcttcaaa    480
cacaacgatc tggatgatct gcgtcgcatc ctgacgagta ttggtaaaga tcgtccgatc    540
ctggttgcgt ttgaaagcgt gtattctatg gatggtgatt tcggccgcat tgaagaaatc    600
tgcgatattg cagatgaatt tggcgcgctg aaatatattg atgaagttca cgcggtgggc    660
atgtacggtc cgcgtggcgg tggcgtggca gaacgtgatg gtctgatgga tcgcatcgat    720
attatcaatg gcaccctggg caaagcctat ggcgttttcg gtggctacat tgcagcgagt    780
agcaaaatgt gtgatgccgt gcgcagctac gcaccgggtt ttatcttctc taccagtctg    840
ccgccggtgg ttgccgcagg tgcggccgca tctgttcgtc atctgaaagg cgatgtggaa    900
ctgcgcgaaa aacaccagac gcaggcgcgt attctgaaaa tgcgcctgaa aggtctgggc    960
ctgccgatta tcgatcatgg tagtcacatc gtgccggttc atgtgggcga tccggttcac   1020
tgcaaaatga ttagcgatat gctgctggaa cattttggta tctatgttca gccgattaac   1080
ttcccgaccg tgccgcgtgg cacggaacgt ctgcgcttta ccccgtctcc ggtgcatgat   1140
agtggcatga tcgatcacct ggttaaagcg atggatgtgc tgtggcagca ctgtgcactg   1200
aatcgcgcgg aagtggttgc ctaa                                          1224

<210> SEQ ID NO 2
<211> LENGTH: 28
<212> TYPE: DNA
<213> ORGANISM: Artificial Sequence
<220> FEATURE:
<223> OTHER INFORMATION: primer
```

```
<400> SEQUENCE: 2
catgccatgg attataacct ggcactgg                                           28

<210> SEQ ID NO 3
<211> LENGTH: 27
<212> TYPE: DNA
<213> ORGANISM: Artificial Sequence
<220> FEATURE:
<223> OTHER INFORMATION: primer

<400> SEQUENCE: 3
ccggaattct taggcaacca cttccgc                                            27

<210> SEQ ID NO 4
<211> LENGTH: 2280
<212> TYPE: DNA
<213> ORGANISM: Artificial Sequence
<220> FEATURE:
<223> OTHER INFORMATION: maeB gene

<400> SEQUENCE: 4
atggatgacc agttaaaaca aagtgcactt gatttccatg aatttccagt tccagggaaa        60
atccaggttt ctccaaccaa gcctctggca acacagcgcg atctggcgct ggcctactca       120
ccaggcgttg ccgcaccttg tcttgaaatc gaaaagacc cgttaaaagc ctacaaatat       180
accgcccgcg gtaacctggt ggcggtgatc tctaacggta cggcggtgct ggggttaggc       240
aacattggcg cgctggcagg caaaccggtg atggaaggca agggcgttct gtttaagaaa       300
ttcgccggga ttgatgtatt tgacattgaa gttgacgaac tcgacccgga caaatttatt       360
gaagttgtcg ccgcgctcga accaaccttc ggcggcatca acctcgaaga cattaaagcg       420
ccagaatgtt tctatattga acagaaactg cgcgagcgga tgaatattcc ggtattccac       480
gacgatcagc acggcacggc aattatcagc actgccgcca tcctcaacgg cttgcgcgtg       540
gtggagaaaa acatctccga cgtgcggatg gtggtttccg gcgcgggtgc cgcagcaatc       600
gcctgtatga acctgctggt agcgctgggt ctgcaaaaac ataacatcgt ggtttgcgat       660
tcaaaaggcg ttatctatca gggccgtgag ccaaacatgg cggaaaccaa agccgcatat       720
gcggtggtgg atgacggcaa acgtaccctc gatgatgtga ttgaaggcgc ggatatttc       780 ctgggctgtt ccggcccgaa agtgctgacc aggaaatgg tgaagaaaat ggctcgtgcg       840
ccaatgatcc tggcgctggc gaacccggaa ccggaaattc tgccgccgct ggcgaaagaa       900
gtgcgtccgg atgccatcat ttgcaccggt cgttctgact atccgaacca ggtgaacaac       960
gtcctgtgct ccccgttcat cttccgtggc gcgctggacg ttggcgcaac cgccatcaac      1020
gaagagatga aactggcggc ggtacgtgcg attgcagaac tcgcccatgc ggaacagagc      1080
gaagtggtgg cttcagcgta tggcgatcag gatctgagct ttggtccgga atacatcatt      1140
ccaaaaccgt ttgatccgcg cttgatcgtt aagatcgctc ctgcggtcgc taaagccgcg      1200
atggagtcgg gcgtggcgac tcgtccgatt gctgatttcg acgtctacat cgacaagctg      1260
actgagttcg tttacaaaac caacctgttt atgaagccga ttttctccca ggctcgcaaa      1320
gcgccgaagc gcgttgttct gccggaaggg gaagaggcgc gcgttctgca tgccactcag      1380
gaactggtaa cgctgggact ggcgaaaccg atccttatcg gtcgtccgaa cgtgatcgaa      1440
atgcgcattc agaaactggg cttgcagatc aaagcgagcg ttgattttga tcgtcaat       1500 aacgaatccg atcgcgctt taagagtac tggaccgaat acttccagat catgaagcgt      1560
cgcggcgtca ctcaggaaca ggcgcagcgg gcgctgatca gtaacccgac agtgatcggc      1620
```

```
gcgatcatgg ttcagcgtgg ggaagccgat gcaatgattt gcggtacggt gggtgattat    1680
catgaacatt ttagcgtggt gaaaaatgtc tttggttatc gcgatggcgt tcacaccgca    1740
ggtgccatga acgcgctgct gctgccgagt ggtaacacct ttattgccga tacatatgtt    1800
aatgatgaac cggatgcaga gagctggcg gagatcacct tgatggcggc agaaactgtc    1860
cgtcgttttg gtattgagcc gcgcgttgct ttgttgtcgc actccaactt tggttcttct    1920
gactgcccgt cgtcgagcaa aatgcgtcag gcgctggaac tggtcaggga acgtgcacca    1980
gaactgatga ttgatggtga aatgcacggc gatgcagcgc tggtggaagc gattcgcaac    2040
gaccgtatgc cggacagctc tttgaaaggt tccgccaata ttctggtgat gccgaacatg    2100
gaagctgccc gcattagtta caacttactg cgtgtttcca gctcggaagg tgtgactgtc    2160
ggcccggtgc tgatgggtgt ggcgaaaccg gttcacgtgt taacgccgat cgcatcggtg    2220
cgtcgtatcg tcaacatggt ggcgctggcc gtggtagaag cgcaaaccca accgctgtaa    2280
```

<210> SEQ ID NO 5
<211> LENGTH: 951
<212> TYPE: DNA
<213> ORGANISM: Artificial Sequence
<220> FEATURE:
<223> OTHER INFORMATION: coaA gene

<400> SEQUENCE: 5

```
atgagtataa aagagcaaac gttaatgacg ccttacctac agtttgaccg caaccagtgg     60
gcagctctgc gtgattccgt acctatgacg ttatcggaag atgagatcgc ccgtctcaaa    120
ggtattaatg aagatctctc gttagaagaa gttgccgaga tctatttacc tttgtcacgt    180
ttgctgaact tctatataag ctcgaatctg cgccgtcagg cagttctgga acagtttctt    240
ggtactaacg ggcaacgcat tccttacatt atcagtattg ctggcagtgt cgcggtgggg    300
aaaagtacaa ccgcccgtgt attgcaggcg ctattaagcc gttggccgga acatcgtcgt    360
gttgaactga tcactacaga tggcttcctt caccctaatc aggttctgaa agaacgtggt    420
ctgatgaaga agaaaggctt cccggaatcg tatgatatgc atcgcctggt gaagtttgtt    480
tccgatctca aatccggcgt gccaaacgtt acagcccctg tttactcgca tcttatttat    540
gatgtgatcc cggatggaga taaaaacggt tgttcagcctg atattttaat tcttgaaggg    600
ttaaatgtct tacagagcgg gatggattat ccacacgatc cacatcatgt atttgtttct    660
gattttgtcg atttttcgat atatgttgat gcaccggaag acttacttca gacgtggtat    720
atcaaccgtt ttctgaaatt ccgcgaaggg gcttttaccg acccggattc ctatttcat    780 aactacgcga aattaactaa agaagaagcg attaagactg ccatgacatt gtggaaagag    840
atcaactggc tgaacttaaa gcaaaatatt ctacctactc gtgagcgcgc cagtttaatc    900
ctgacgaaaa gtgctaatca tgcggtagaa gaggtcagac tacgcaaata a             951
```

<210> SEQ ID NO 6
<211> LENGTH: 31
<212> TYPE: DNA
<213> ORGANISM: Artificial Sequence
<220> FEATURE:
<223> OTHER INFORMATION: primer

<400> SEQUENCE: 6

```
gaagatctat ggatgaccag ttaaaacaaa g                                      31
```

<210> SEQ ID NO 7

```
<211> LENGTH: 27
<212> TYPE: DNA
<213> ORGANISM: Artificial Sequence
<220> FEATURE:
<223> OTHER INFORMATION: primer

<400> SEQUENCE: 7
ccgctcgagt tacagcggtt gggtttg                                              27

<210> SEQ ID NO 8
<211> LENGTH: 48
<212> TYPE: DNA
<213> ORGANISM: Artificial Sequence
<220> FEATURE:
<223> OTHER INFORMATION: primer

<400> SEQUENCE: 8
cgagctcata aaaggaggaa aatatatgag tataaaagag caaacgtt                       48

<210> SEQ ID NO 9
<211> LENGTH: 32
<212> TYPE: DNA
<213> ORGANISM: Artificial Sequence
<220> FEATURE:
<223> OTHER INFORMATION: primer

<400> SEQUENCE: 9
acgcgtcgac ttatttgcgt agtctgacct ct                                        32

<210> SEQ ID NO 10
<211> LENGTH: 1416
<212> TYPE: DNA
<213> ORGANISM: Artificial Sequence
<220> FEATURE:
<223> OTHER INFORMATION: gltX gene

<400> SEQUENCE: 10
atgaaaatca aaactcgctt cgcgccaagc ccaacaggct atctgcacgt tggcggcgcg         60
cgtactgctc tttactcctg cttttttgca cgtaaccacg gcggtgagtt cgtgctgcgt        120
attgaagaca ccgatcttga gcgttccacg ccggaagcta tcgaagccat tatggatggc        180
atgaactggc tgagcctgga gtgggatgaa ggtccgtact accagaccaa acgttttgat        240
cgctacaacg cggtgatcga tcagatgctg aagagggca ctgcttataa atgctattgc         300
tctaaagagc gcctggaagc gctgcgcgaa gagcaaatgg cgaaaggtga aagccgcgt         360
tatgacggtc gctgccgcca cagccatgag catcatgctg atgatgaacc gtgtgttgta        420
cgttttgcta acccgcagga aggttctgtt gttttttgacg atcagatccg tggtccgatc        480
gagttcagca accaggaact ggacgatctt attatccgcc gtaccgatgg ttccccaacc        540
tataacttct gtgtggttgt cgatgactgg gatatggaaa tcacccacgt tatccgtggc        600
gaagaccata tcaacaacac gccacgccag atcaacattc ttaaggccct gaaagcgccg        660
gtgccggttt acgcgcacgt ttctatgatc aatggcgatg acgtaaaaa actgtccaaa         720
cgtcacgggg cagtcagcgt aatgcagtat cgtgatgacg ttatttgcc agaagcactg         780
ctgaactatc tggtgcgtct gggctggtcc cacggcgatc aggaaatctt cactcgtgaa        840
gagatgatca atacttcac tttgaatgcc gtcagcaaat ctgccagtgc gttcaacacc         900
gacaagctgc tgtggctgaa ccatcactac attaacgcgc tgccgccgga gtatgttgct        960
actcacttac agtggcacat tgagcaggaa aatatcgata cccgtaacgg cccgcagctg       1020
gctgatctgg tgaaactgct gggcgaacgc tgcaagacgc tgaaagagat ggcacagagc       1080
```

```
tgccgttatt tctacgaaga ttttgctgag ttcgatgccg acgccgcgaa aaaacatctg    1140
cgtccggtag cgcgtcagcc gctggaagtg gttcgtgaca actggccgc gattactgac     1200 tggaccgctg aaaacgttca tcacgctatt caggcgacgg cggatgagct ggaagtgggt    1260
atgggtaaag ttggtatgcc gctgcgtgtc gccgtaaccg gtgcgggca gtctccagca    1320 ctggatgtta ccgttcacgc aattggtaag acccgcagta tcgagcgtat caacaaagcg    1380
ctggatttta ttgctgaacg cgaaaatcag cagtaa                              1416
```

<210> SEQ ID NO 11
<211> LENGTH: 1281
<212> TYPE: DNA
<213> ORGANISM: Artificial Sequence
<220> FEATURE:
<223> OTHER INFORMATION: hemL gene

<400> SEQUENCE: 11

```
atgagtaagt ctgaaaatct ttacagcgca gcgcgcgagc tgatccctgg cggtgtgaac    60
tcccctgttc gcgcctttac tggcgtgggc ggcactccac tgtttatcga aaaagcggac    120
ggcgcttatc tgtacgatgt tgatggcaaa gcctatatcg attatgtcgg ttcctgggg     180 ccgatggtgc tgggccataa ccatccggca atccgcaatg ccgtgattga agccgccgag    240
cgtggtttaa gctttggtgc accaaccgaa atggaagtga aaatggcgca actggtgact    300
gaactggtcc cgaccatgga tatggtgcgc atggtgaact ccggcaccga ggcgacgatg    360
agcgccatcc gcctggcccg tggttttacc ggtcgcgaca aaattattaa atttgaaggt    420
tgttaccacg gtcacgctga ctgcctgctg gtgaaagccg ttctggcgc actcacgtta    480 ggccagccaa actcgccggg cgttccggca gatttcgcca acataccctt aacctgtact    540
tataacgatc tggcttctgt acgcgccgcg tttgagcaat acccgcaaga gattgcctgt    600
attatcgtcg agccggtggc aggcaatatg aactgcgttc caccgctgcc agagttcctg    660
ccaggtctgc gtgcgctgtg cgacgaattt ggcgcattgc tgatcatcga tgaagtaatg    720
accggcttcc gcgtggcact ggctggcgca caggattatt acggtgtgga accggatctc    780
acctgcctgg gcaaaatcat cggcggtgga atgccggtag cgcattcgg tggtcgtcgt    840 gatgtaatgg atgcgctggc cccgacgggt ccggtctatc aggcgggtac gctttccggt    900
aacccaattg cgatggcagc gggttttgcc tgtctgaatg aagtcgcgca gccgggcgtt    960
cacgaaacgt tggatgagct gacatcacgt ctggcagaag gtctgctgga agcggcagaa    1020
gaagccggaa ttccgctggt cgttaaccac gttggcggca tgttcggtat tttcttacc    1080 gacgccgagt ccgtgacgtg ctatcaggat gtgatggcct gtgacgtgga acgctttaag    1140
cgtttcttcc atatgatgct ggacgaaggt gtttacctgg caccgtcagc gtttgaagcg    1200
ggctttatgt ccgtggcgca cagcatggaa gatatcaata acaccatcga tgctgcacgt    1260
cgggtgtttg cgaagttgtg a                                               1281
```

<210> SEQ ID NO 12
<211> LENGTH: 1263
<212> TYPE: DNA
<213> ORGANISM: Artificial Sequence
<220> FEATURE:
<223> OTHER INFORMATION: hemA/\fbr gene

<400> SEQUENCE: 12

```
atgaccaaga agctttttagc actcggtatc aaccataaaa cggcacctgt atcgctgcga    60
```

```
gaacgtgtat cgttttcgcc ggataagctc gatcaggcgc ttgacagcct gcttgcgcag    120
ccgatggtgc agggcggcgt ggtgctgtcg acgtgcaacc gcacggaact ttatcttagc    180
gttgaagagc aggataacct gcaagaggcg ttaatccgct ggctttgcga ttatcacaat    240
cttaatgaag aagatctgcg taaaagcctc tactggcatc aggataacga cgcggttagc    300
catttaatgc gtgttgccag cggcctggat tcattggttc ttggggagcc gcagatcctc    360
ggtcaggtta aaaagcgtt tgccgattcg caaaaggcc atatgaaggc cagcgaactg     420
gaacgcatgt tccagaaatc tttctctgta gcgaaacgcg ttcgcactga aacagatatc    480
ggtgccagcg ctgtgtctgt cgcttttgcg gcttgtacgc tggcgcggca gatctttgaa    540
tcgctctcta cggtcacagt gttgctggta ggcgcgggcg aaaccatcga gctggtagcg    600
cgtcatctgc gcgaacataa agtacagaag atgattatcg ccaaccgcac tcgcgaacgt    660
gcccaaatac tggcagatga agttggcgcg gaagtgattg ccctgagtga gatcgacgaa    720
cgtctgcgcg aagccgatat catcatcagt tccaccgcca gcccgttacc gattatcggg    780
aaaggcatgg tggagcgcgc attaaaaagc cgtcgcaacc aaccaatgct gttggtggat    840
attgccgttc cgcgcgatgt tgagccggaa gttggcaaac tggcgaatgc ttatctttat    900
agcgtggacg atctgcaaag catcatttcg cacaacctgg cgcagcgtaa agccgcagcg    960
gttgaggcgg aaactattgt cgctcaggaa accagcgaat ttatggcgtg gctgcgagca   1020
caaagcgcca gcgaaaccat cgcgagtat cgcagccagg cagagcaagt tcgcgatgag    1080
ttaaccgcca aagcgttagc ggcccttgag cagggcggcg acgcgcaagc cattatgcag   1140
gatctggcat ggaaactgac taaccgcttg atccatgcgc caacgaaatc acttcaacag   1200
gccgcccgtg acggggataa cgaacgcctg aatattctgc gcgacagcct cgggctggag   1260
tag                                                                 1263

<210> SEQ ID NO 13
<211> LENGTH: 31
<212> TYPE: DNA
<213> ORGANISM: Artificial Sequence
<220> FEATURE:
<223> OTHER INFORMATION: primer

<400> SEQUENCE: 13
ggaattccat atgaaaatca aaactcgctt c                                   31

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
ccgctcgagt tactgctgat tttcgcgt                                       28

<210> SEQ ID NO 15
<211> LENGTH: 51
<212> TYPE: DNA
<213> ORGANISM: Artificial Sequence
<220> FEATURE:
<223> OTHER INFORMATION: primer

<400> SEQUENCE: 15
cgagctcata aaaggaggaa aatatatgag taagtctgaa atctttaca g              51
```

```
<210> SEQ ID NO 16
<211> LENGTH: 37
<212> TYPE: DNA
<213> ORGANISM: Artificial Sequence
<220> FEATURE:
<223> OTHER INFORMATION: primer

<400> SEQUENCE: 16
aaggaaaaaa gcggccgctc acaacttcgc aaacacc                                   37

<210> SEQ ID NO 17
<211> LENGTH: 43
<212> TYPE: DNA
<213> ORGANISM: Artificial Sequence
<220> FEATURE:
<223> OTHER INFORMATION: primer

<400> SEQUENCE: 17
catgccatgg gtaccaagaa gcttttagca ctcggtatca acc                            43

<210> SEQ ID NO 18
<211> LENGTH: 27
<212> TYPE: DNA
<213> ORGANISM: Artificial Sequence
<220> FEATURE:
<223> OTHER INFORMATION: primer

<400> SEQUENCE: 18
cgcggatccc tactccagcc cgaggct                                              27

<210> SEQ ID NO 19
<211> LENGTH: 975
<212> TYPE: DNA
<213> ORGANISM: Artificial Sequence
<220> FEATURE:
<223> OTHER INFORMATION: hemB gene

<400> SEQUENCE: 19
atgacagact taatccaacg ccctcgtcgc ctgcgcaaat ctcctgcgct gcgcgctatg          60
tttgaagaga caacacttag ccttaacgac ctggtgttgc cgatctttgt tgaagaagaa         120
attgacgact acaaagccgt tgaagccatg ccaggtgtga tgcgcattcc agagaaacat         180
ctggcacgcg aaattgaacg catcgccaac gccggtattc gttccgtgat gactttcggc         240
atctctcacc ataccgatga aaccggcagc gatgcctggc gggaagatgg actggtggcg         300
cgaatgtcgc gcatctgcaa gcagaccgtg ccagaaatga tcgtcatgtc agacacctgc         360
ttctgcgaat acacatctca cggtcactgc ggtgtgctgt gcgagcatgg cgtcgacaac         420
gacgcgactc tggaaaattt aggcaagcaa gccgtggttg cagctgctgc aggcgcagac         480
ttcatcgccc cttctgccgc gatggacggc caggtacagg cgattcgcca ggcgctggac         540
gctgcgggct ttaaagatac ggcgattatg tcgtattcga ccaagttcgc ctcttccttt         600
tatggtccgt ccgtgaagc tgccggaagc gcattaaaag cgaccgcaa aagctatcag          660 atgaacccaa tgaaccgtcg tgaggcgatt cgtgagtcac tgctggatga agcccagggc         720
gcagactgtc tgatggttaa acctgccgga gcgtacctcg acatcgtgcg tgagctgcgt         780
gaacgtactg aattgccgat ggcgcgtat caggtgagcg tgagtacgc gatgattaag          840 ttcgccgcgc tggcgggtgc tatagatgaa gagaaagtcg tgctcgaaag cttaggttca         900
attaagcgtg cgggtgcgga tctgattttc agctactttg cgatggattt ggctgagaag         960
aagattctgc gttaa                                                         975
```

<210> SEQ ID NO 20
<211> LENGTH: 963
<212> TYPE: DNA
<213> ORGANISM: Artificial Sequence
<220> FEATURE:
<223> OTHER INFORMATION: hemH gene

<400> SEQUENCE: 20

```
atgcgtcaga ctaaaaccgg tatcctgctg gcaaacctgg gtacgcccga tgcccccaca      60
cctgaagcgg taaaacgcta tctgaaacaa ttttttaagcg acagacgcgt ggttgatacc    120
tcacggttgt tatggtggcc attgctgcgc ggcgtgattt tgccgctgcg ctcgccgcgt    180
gtggcgaagc tgtatgcctc tgtctggatg aaggtggcc cgccgctgat ggtttacagc      240
cgtcagcaac agcaggcgct ggcacaacgt ttaccggaga cgcccgtagc gctgggaatg    300
agctacggct cgccatcact ggaaagcgcc gtagatgaac tcctggcaga gcatgtagat    360
catattgtgg tgctgccgct ttatccgcaa tactcctgtt caacggtcgg tgcggtatgg    420
gatgaactgg cacgcattct ggcgcgcaaa cgtagcattc cggggatatc gtttattcgt    480
gattacgctg ataaccacga ttacattaat gcactggcga acagcgtacg cgcttctttt    540
gccaaacatg gcgaaccgga tctgctgctg ctctcttatc atggcattcc ccagcgttat    600
gcagatgaag gcgatgatta cccgcaacgt tgccgcacaa cgactcgcga actggcttcc    660
gcactgggga tggcaccgga aaagtgatg atgaccttc agtcgcgctt tggtcgggaa      720
ccctggctga tgccttatac cgacgaaacg ctgaaaatgc tcggagaaaa aggcgtaggt    780
catatacagg tgatgtgccc gggctttgct gcggattgtc tggagacgct ggaagagatt    840
gccgagcaaa accgtgaggt cttcctcggt gccggcggga aaaaatatga atatattcca    900
gcgcttaatg ccacgccgga acatattgaa atgatggcta atcttgttgc cgcgtatcgc    960
taa                                                                 963
```

<210> SEQ ID NO 21
<211> LENGTH: 31
<212> TYPE: DNA
<213> ORGANISM: Artificial Sequence
<220> FEATURE:
<223> OTHER INFORMATION: primer

<400> SEQUENCE: 21

```
ggaattccat atgacagact taatccaacg c                                    31
```

<210> SEQ ID NO 22
<211> LENGTH: 32
<212> TYPE: DNA
<213> ORGANISM: Artificial Sequence
<220> FEATURE:
<223> OTHER INFORMATION: primer

<400> SEQUENCE: 22

```
ccgctcgagt taacgcagaa tcttcttctc ag                                   32
```

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23

```
ggaattccat atgcgtcaga ctaaaaccgg                                      30
```

<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
ccgctcgagt tagcgatacg cggcaac       27

<210> SEQ ID NO 25
<211> LENGTH: 30
<212> TYPE: DNA
<213> ORGANISM: Artificial Sequence
<220> FEATURE:
<223> OTHER INFORMATION: primer

<400> SEQUENCE: 25
catgccatgg gtacagactt aatccaacgc    30

<210> SEQ ID NO 26
<211> LENGTH: 32
<212> TYPE: DNA
<213> ORGANISM: Artificial Sequence
<220> FEATURE:
<223> OTHER INFORMATION: primer

<400> SEQUENCE: 26
cgcggatcct taacgcagaa tcttcttctc ag   32

<210> SEQ ID NO 27
<211> LENGTH: 942
<212> TYPE: DNA
<213> ORGANISM: Artificial Sequence
<220> FEATURE:
<223> OTHER INFORMATION: hemC gene

<400> SEQUENCE: 27
atgttagaca atgttttaag aattgccaca cgccaaagcc cacttgcact ctggcaggca    60
cactatgtca agacaagtt gatggcgagc catccgggcc tggtcgttga actggtaccg   120
atggtgacgc gcggcgatgt gattcttgat acgccgctgg cgaaagtagg cggaaaaggc   180
ttatttgtta aagagctgga agtcgcgctc ctcgaaaatc gcgccgatat cgccgtacat   240
tcaatgaaag atgtgccggt tgaattcccg caaggtctgg gactggtcac tatttgtgag   300
cgtgaagatc ctcgcgatgc ctttgtgtcc aataactatg acaatctgga tgcgttaccg   360
gcaggcagta tcgtcgggac gtccagttta cgtcgccagt gccaactggc tgaacgccgc   420
ccggatctga ttatccgctc cctgcgaggc aacgtcggca ctcgcctgag taaactggat   480
aacggcgaat acgatgccat cattcttgcg gtagccggac taaaacgttt aggtctggag   540
tcccgcattc gcgccgcatt gccacccgag atttctcttc cggcggtagg acaaggtgcg   600
gtgggtattg aatgccgcct tgatgattct cgcactcgcg agctgcttgc cgcgctgaat   660
caccacgaaa ctgcactgcg cgttaccgca gaacgcgcca tgaatacccg tctcgaaggc   720
ggatgtcagg tgccaattgg tagctacgcc gagcttattg atggcgaaat ctggctgcgt   780
gcgttggtcg gcgcgccgga cggttcgcag attattcgcg gtgaacgccg cggtgcgccg   840
caagatgccg aacaaatggg gatttcgctg gcagaagagc tactgaataa cggcgcgcgc   900
gagatcctcg ctgaagtcta taacggagac gctccggcat ga                     942

<210> SEQ ID NO 28
<211> LENGTH: 741
<212> TYPE: DNA
<213> ORGANISM: Artificial Sequence
<220> FEATURE:
<223> OTHER INFORMATION: hemD gene

<400> SEQUENCE: 28

| | | | | | |
|---|---|---|---|---|---|
| atgagtatcc | tggtcacccg | cccgtctccc | gctggagaag | agttagtgag | ccgtctgcgc | 60 |
| acactggggc | aggtggcctg | gcattttcca | ctgattgagt | tttctccggg | tcgacaatta | 120 |
| ccacaacttg | ctgatcaact | ggcggcgctg | ggggagagcg | atctgttgtt | tgccctctcg | 180 |
| caacacgcgg | ttgcttttgc | ccaatcacag | ctgcatcagc | aagatcgtaa | atggccccga | 240 |
| ctacctgatt | atttcgccat | ggacgcacc | accgcactgg | cactacatac | cgtaagcgga | 300 |
| cagaagattc | tctacccgca | ggatcgggaa | atcagcgaag | tcttgctaca | attacctgaa | 360 |
| ttacaaaata | ttgcgggcaa | acgtgcgctg | atattacgtg | gcaatggcgg | tcgtgagcta | 420 |
| attggggata | ccctgacggc | gcgcggtgct | gaggtcactt | tttgtgaatg | ttatcaacga | 480 |
| tgcgcaatcc | attacgatgg | tgcagaagaa | gcgatgcgct | ggcaatcccg | cgaggtgacg | 540 |
| acggtcgttg | ttaccagcgg | tgaaatgttg | cagcaactct | ggtcgctgat | cccacaatgg | 600 |
| tatcgtgagc | actggttact | acactgtcga | ctattggtcg | tcagtgagcg | tttggcgaaa | 660 |
| ctcgcccggg | aactgggctg | gcaagacatt | aaggtcgccg | ataacgctga | caacgatgcg | 720 |
| cttttacggg | cattacaata | a | | | | 741 |

<210> SEQ ID NO 29
<211> LENGTH: 1065
<212> TYPE: DNA
<213> ORGANISM: Artificial Sequence
<220> FEATURE:
<223> OTHER INFORMATION: hemE gene

<400> SEQUENCE: 29

| | | | | | |
|---|---|---|---|---|---|
| atgaccgaac | ttaaaaacga | tcgttatctg | cgggcgctgc | tgcgccagcc | cgttgatgtc | 60 |
| actccagtat | ggatgatgcg | ccaggcgggt | cgctatctac | cggaatataa | agccacgcgc | 120 |
| gcccaggcgg | gcgattttat | gtcgctgtgc | aaaaacgccg | agctggcgtg | cgaagtgact | 180 |
| ttgcaaccgc | tgcgtcgcta | cccgctggat | gcggcgatcc | tcttttccga | tatcctcacc | 240 |
| gtgccggacg | cgatggggtt | agggctctat | tttgaagccg | gagaaggtcc | gcgttttacc | 300 |
| tcgccagtca | cctgcaaagc | cgacgtcgat | aaactgccaa | ttccggaccc | ggaagatgag | 360 |
| ctgggttacg | tgatgaacgc | ggtgcgtacc | attcgtcgcg | aactgaaagg | cgaagtgccg | 420 |
| ctgattggtt | tttccggcag | cccgtggacg | ctggcgacct | acatggtgga | aggcggcagc | 480 |
| agcaaagcgt | tcaccgtgat | caaaaaaatg | atgtatgccg | atccgcaggc | gctgcacgct | 540 |
| ctactcgata | aactggcgaa | aagcgtcact | ttgtatctga | atgcgcagat | taaagccggt | 600 |
| gctcaggcag | tgatgatttt | cgacacctgg | ggcggtgtgc | ttaccgggcg | cgattatcaa | 660 |
| cagttctcgc | tctattacat | gcataaaatt | gttgatggtt | tactgcgtga | aaacgacggt | 720 |
| cgccgcgtac | cggtcacgct | gtttaccaaa | ggcggcggac | agtggctgga | agcgatggca | 780 |
| gaaaccggtt | gcgatgcgtt | gggcctcgac | tggacaacgg | atatcgccga | tgcgcgccgc | 840 |
| cgtgtgggca | ataaagtcgc | gttgcagggt | aatatggatc | cgtcgatgct | gtacgctccg | 900 |
| cctgcccgca | ttgaagaaga | agtagcgact | atacttgcag | gtttcggtca | cggcgaaggt | 960 |
| catgtcttta | accttggtca | cggcattcat | caggatgtgc | cgccagaaca | tgctggcgta | 1020 |

```
ttcgtggagg cagtgcatcg actgtctgaa caatatcacc gctaa          1065
```

<210> SEQ ID NO 30
<211> LENGTH: 900
<212> TYPE: DNA
<213> ORGANISM: Artificial Sequence
<220> FEATURE:
<223> OTHER INFORMATION: hemF gene

<400> SEQUENCE: 30

```
atgaaacccg acgcacacca ggttaaacag tttctgctca accttcagga tacgatttgt    60
cagcagctga ccgccgtcga tggcgcagaa tttgtcgaag atagttggca gcgcgaagct   120
ggcggcggcg ggcgtagtcg ggtgttgcgt aatggtggtg ttttcgaaca ggcaggcgtc   180
aacttttcgc atgtccacgg tgaggcgatg cctgcttccg ccaccgctca tcgcccggaa   240
cttgccgggc gcagtttcga ggcgatgggc gtttcactgg tagtgcatcc gcataacccg   300
tatgttccca ccagccacgc gaatgtgcgg ttttttattg ccgaaaaacc gggtgccgat   360
cccgtctggt ggtttggcgg cggcttcgat ttaacccctt tctatggttt tgaagaagac   420
gccattcact ggcaccgcac cgcccgtgac ctgtgcctgc catttggtga agacgtttat   480
ccccgttaca aaaagtggtg cgacgattac ttctacctca acatcgcaa cgaacagcgc   540
ggtattggcg gctgttctt tgatgatctg aacacgccag atttcgacca ctgttttgcc   600
tttatgcagg cggtaggcaa aggctacacc gacgcttatt accaattgt agagcgacgt   660
aaagcgatgg cctacggcga gcgcgagcgc aattttcagc tctaccgtcg cggtcgttat   720
gtcgagttca atctggtctg ggatcgcggc acgctgtttg gcctgcaaac tggcgggcgc   780
accgagtcta tcctgatgtc aatgccgcca ctggtacgct gggaatatga ttatcagcca   840
aaagatggca gcccagaagc ggcgttaagt gagtttatta aggtcaggga ttgggtgtaa   900
```

<210> SEQ ID NO 31
<211> LENGTH: 546
<212> TYPE: DNA
<213> ORGANISM: Artificial Sequence
<220> FEATURE:
<223> OTHER INFORMATION: hemG gene

<400> SEQUENCE: 31

```
gtgaaaacat taattctttt ctcaacaagg gacggacaaa cgcgcgagat tgcctcctac    60
ctggcttcgg aactgaaaga actggggatc caggcggatg tcgccaatgt gcaccgcatt   120
gaagaaccac agtgggaaaa ctatgaccgt gtggtcattg gtgcttctat cgctatggt   180
cactaccatt cagcgttcca ggaatttgtc aaaaaacatg cgacgcggct gaattcgatg   240
ccgagcgcct tttactccgt gaatctggtg gcgcgcaaac cggagaagcg tactccacag   300
accaacagct acgcgcgcaa gtttctgatg aactcgcaat ggcgtcccga tcgctgcgcg   360
gtcattgccg gggcgctgcg ttacccacgt tatcgctggt acgaccgttt tatgatcaag   420
ctgattatga agatgtcagg cggtgaaacg gatacgcgca agaagttgt ctataccgat   480
tgggagcagg tggcgaattt cgcccgagaa atcgcccatt taaccgacaa accgacgctg   540
aaataa                                                              546
```

<210> SEQ ID NO 32
<211> LENGTH: 38
<212> TYPE: DNA
<213> ORGANISM: Artificial Sequence
<220> FEATURE:

```
<223> OTHER INFORMATION: primer

<400> SEQUENCE: 32
catgccatgg gtatgttaga caatgtttta agaattgc                           38

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
cgcggatcct catgccggag cgtctc                                        26

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
catgccatgg gtatgagtat cctggtcacc cg                                 32

<210> SEQ ID NO 35
<211> LENGTH: 31
<212> TYPE: DNA
<213> ORGANISM: Artificial Sequence
<220> FEATURE:
<223> OTHER INFORMATION: primer

<400> SEQUENCE: 35
cgcggatcct tattgtaatg cccgtaaaag c                                  31

<210> SEQ ID NO 36
<211> LENGTH: 34
<212> TYPE: DNA
<213> ORGANISM: Artificial Sequence
<220> FEATURE:
<223> OTHER INFORMATION: primer

<400> SEQUENCE: 36
catgccatgg gtatgaccga acttaaaaac gatc                               34

<210> SEQ ID NO 37
<211> LENGTH: 31
<212> TYPE: DNA
<213> ORGANISM: Artificial Sequence
<220> FEATURE:
<223> OTHER INFORMATION: primer

<400> SEQUENCE: 37
ccggaattct tagcggtgat attgttcaga c                                  31

<210> SEQ ID NO 38
<211> LENGTH: 30
<212> TYPE: DNA
<213> ORGANISM: Artificial Sequence
<220> FEATURE:
<223> OTHER INFORMATION: primer

<400> SEQUENCE: 38
catgccatgg gtatgaaacc cgacgcacac                                    30
```

```
<210> SEQ ID NO 39
<211> LENGTH: 29
<212> TYPE: DNA
<213> ORGANISM: Artificial Sequence
<220> FEATURE:
<223> OTHER INFORMATION: primer

<400> SEQUENCE: 39
cgcggatcct tacacccaat ccctgacct                                      29

<210> SEQ ID NO 40
<211> LENGTH: 38
<212> TYPE: DNA
<213> ORGANISM: Artificial Sequence
<220> FEATURE:
<223> OTHER INFORMATION: primer

<400> SEQUENCE: 40
catgccatgg gtgtgaaaac attaattctt ttctcaac                            38

<210> SEQ ID NO 41
<211> LENGTH: 28
<212> TYPE: DNA
<213> ORGANISM: Artificial Sequence
<220> FEATURE:
<223> OTHER INFORMATION: primer

<400> SEQUENCE: 41
cgagctctta tttcagcgtc ggtttgtc                                       28

<210> SEQ ID NO 42
<211> LENGTH: 37
<212> TYPE: DNA
<213> ORGANISM: Artificial Sequence
<220> FEATURE:
<223> OTHER INFORMATION: primer

<400> SEQUENCE: 42
gggaattcca tatgttagac aatgttttaa gaattgc                             37

<210> SEQ ID NO 43
<211> LENGTH: 25
<212> TYPE: DNA
<213> ORGANISM: Artificial Sequence
<220> FEATURE:
<223> OTHER INFORMATION: primer

<400> SEQUENCE: 43
gaagatcttc atgccggagc gtctc                                          25

<210> SEQ ID NO 44
<211> LENGTH: 46
<212> TYPE: DNA
<213> ORGANISM: Artificial Sequence
<220> FEATURE:
<223> OTHER INFORMATION: primer

<400> SEQUENCE: 44
gaagatctat aaaaggagga aaatatgga gtatcctggt cacccg                    46

<210> SEQ ID NO 45
<211> LENGTH: 31
<212> TYPE: DNA
<213> ORGANISM: Artificial Sequence
<220> FEATURE:
<223> OTHER INFORMATION: primer
```

```
<400> SEQUENCE: 45
ccgctcgagt tattgtaatg cccgtaaaag c                              31

<210> SEQ ID NO 46
<211> LENGTH: 31
<212> TYPE: DNA
<213> ORGANISM: Artificial Sequence
<220> FEATURE:
<223> OTHER INFORMATION: primer

<400> SEQUENCE: 46
catgccatgg gtaccgaact taaaaacgat c                              31

<210> SEQ ID NO 47
<211> LENGTH: 29
<212> TYPE: DNA
<213> ORGANISM: Artificial Sequence
<220> FEATURE:
<223> OTHER INFORMATION: primer

<400> SEQUENCE: 47
cgagctctta gcggtgatat tgttcagac                                 29

<210> SEQ ID NO 48
<211> LENGTH: 43
<212> TYPE: DNA
<213> ORGANISM: Artificial Sequence
<220> FEATURE:
<223> OTHER INFORMATION: primer

<400> SEQUENCE: 48
cgagctcata aaaggaggaa aatatatgaa acccgacgca cac                 43

<210> SEQ ID NO 49
<211> LENGTH: 30
<212> TYPE: DNA
<213> ORGANISM: Artificial Sequence
<220> FEATURE:
<223> OTHER INFORMATION: primer

<400> SEQUENCE: 49
aaaactgcag ttacacccaa tccctgacct                                30

<210> SEQ ID NO 50
<211> LENGTH: 54
<212> TYPE: DNA
<213> ORGANISM: Artificial Sequence
<220> FEATURE:
<223> OTHER INFORMATION: primer

<400> SEQUENCE: 50
aaaactgcag ataaaaggag gaaatatgt gaaaacatta attcttttct caac      54

<210> SEQ ID NO 51
<211> LENGTH: 39
<212> TYPE: DNA
<213> ORGANISM: Artificial Sequence
<220> FEATURE:
<223> OTHER INFORMATION: primer

<400> SEQUENCE: 51
aaggaaaaaa gcggccgctt atttcagcgt cggtttgtc                      39

<210> SEQ ID NO 52
<211> LENGTH: 71
```

```
<212> TYPE: DNA
<213> ORGANISM: Artificial Sequence
<220> FEATURE:
<223> OTHER INFORMATION: primer

<400> SEQUENCE: 52 tattttagt agcttaaatg tgattcaaca tcactggaga aagtcttatg taggtgacac    60
tatagaacgc g                                                        71

<210> SEQ ID NO 53
<211> LENGTH: 70
<212> TYPE: DNA
<213> ORGANISM: Artificial Sequence
<220> FEATURE:
<223> OTHER INFORMATION: primer

<400> SEQUENCE: 53
ctcccctggg ttgcagggga gcggcaagat taaaccagtt cgttcgggca tagtggatct   60
gatgggtacc                                                          70

<210> SEQ ID NO 54
<211> LENGTH: 71
<212> TYPE: DNA
<213> ORGANISM: Artificial Sequence
<220> FEATURE:
<223> OTHER INFORMATION: primer

<400> SEQUENCE: 54
gctgttttgt aacccgccaa atcggcggta acgaaagagg ataaaccgtg taggtgacac   60
tatagaacgc g                                                        71

<210> SEQ ID NO 55
<211> LENGTH: 70
<212> TYPE: DNA
<213> ORGANISM: Artificial Sequence
<220> FEATURE:
<223> OTHER INFORMATION: primer

<400> SEQUENCE: 55
gcagcgcaaa gctgcggatg atgacgagat tactgctgct gtgcagactg tagtggatct   60
gatgggtacc                                                          70

<210> SEQ ID NO 56
<211> LENGTH: 71
<212> TYPE: DNA
<213> ORGANISM: Artificial Sequence
<220> FEATURE:
<223> OTHER INFORMATION: primer

<400> SEQUENCE: 56
tcaacaatgc cacggattgc gtggcattct tattttcagg aggaacaatg taggtgacac   60
tatagaacgc g                                                        71

<210> SEQ ID NO 57
<211> LENGTH: 70
<212> TYPE: DNA
<213> ORGANISM: Artificial Sequence
<220> FEATURE:
<223> OTHER INFORMATION: primer

<400> SEQUENCE: 57
ctggccttta atcaatgaat cagaaacgct tacagcgcca tcaacttgtc tagtggatct   60
```
gatgggtacc                                                                    70

<210> SEQ ID NO 58
<211> LENGTH: 624
<212> TYPE: DNA
<213> ORGANISM: Artificial Sequence
<220> FEATURE:
<223> OTHER INFORMATION: ccmA gene

<400> SEQUENCE: 58
gtgggtatgc ttgaagccag agagttactt tgtgagcggg atgaacgaac cttatttagt      60
ggcttgtcat ttacgctgaa cgcaggagag tgggtacaaa tcaccggtag caacggcgcg     120
gggaagacaa cgcttctccg tttgctgacg gggttgtctc gccctgacgc aggcgaggtt     180
ctctggcaag ggcagccctt gcatcaggta cgcgacagct accatcaaaa cctgttatgg     240
ataggccatc agccggggat caaaacccgg ctgacggcgt tagaaaatct gcactttttat    300
catcgcgatg gcgataccgc acaatgtctg gaagccctgg cgcaggccgg gcttgccgga     360
ttcgaagata ttcctgtaaa tcagctctcg gccgggcaac aacgccgcgt cgctttagcg     420
cgtctgtggc tgacccgtgc cacgttatgg atcctcgacg agcctttta cgcgattgac       480
gttaacggcg tcgatcgtct gacccagcgt atggcgcagc atacggagca ggggggggatt    540
gtgattctga ctaccccacca gccgctcaac gttgctgaaa gtaaaattcg ccgcatttca    600
ctgacgcaaa cgagggccgc atga                                            624

<210> SEQ ID NO 59
<211> LENGTH: 663
<212> TYPE: DNA
<213> ORGANISM: Artificial Sequence
<220> FEATURE:
<223> OTHER INFORMATION: ccmB gene

<400> SEQUENCE: 59
atgatgttct ggcgcatttt ccgtcttgag ctgcgtgtag cgtttcgcca tagcgccgaa      60
atcgccaacc cgctgtggtt cttcctgatt gtaattaccc ttttccgct cagtatcggt      120
ccggagccgc aactgctggc gcgtattgca ccgggcatta tctgggttgc tgcgctgctt     180
tcatccttgc tggcgctgga acgactgttc cgtgacgatt gcaggacgg cagtcttgaa      240
caattgatgt tgttgccgtt acccttgccc gccgttgtgc tggcgaaggt gatggcgcac     300
tggatggtaa ccggtctgcc gttactcatc cttttcgccac tggtagcaat gctactggga     360
atggatgttt atggctggca agtgatggcg ctgacgctgc tgctgggaac gcctacgctt     420
ggctttctcg gtgcaccggg tgtggcgttg acagtgggac ttaagcgcgg tggtgtgctg     480
ctcagcatac tggtgttacc gctgactatc ccattactca tctttgccac cgccgcgatg     540
gacgcggctt ccatgcattt gcccgttgac gggtatctgg caattttagg gcgcgttgctg    600
gcaggcaccg cgacattaag tccttttgcg acggcggcag cgttacgaat cagcattcaa     660
taa                                                                   663

<210> SEQ ID NO 60
<211> LENGTH: 738
<212> TYPE: DNA
<213> ORGANISM: Artificial Sequence
<220> FEATURE:
<223> OTHER INFORMATION: ccmC gene

<400> SEQUENCE: 60
atgtggaaaa cactgcatca actggcgatc ccaccacggc tgtatcaaat ctgtggctgg      60

```
tttataccgt ggctggcaat tgccagtgtg gtcgtgctta ccgtcggctg gatctgggga    120
ttcggctttg ctccggctga ttatcagcag ggaaatagct accgcattat ctacctgcat    180
gtgcctgcgg cgatctggtc gatgggcatt tatgcatcaa tggcagtggc agcgtttatt    240
ggccttgtct ggcagatgaa aatggccaac ctggcggtgg cggcgatggc ccccattggt    300
gccgtgttta cctttattgc cctggttacc ggctctgcat ggggaaaacc gatgtggggc    360
acctggtggg tatgggatgc acgtctgact tctgaactgg tgctgctgtt tttgtatgtg    420
ggtgtgattg ccctgtggca cgccttcgac daccgccgtc tggcgggccg tgcggcaggt    480
atcctggtgc tgattggcgt ggtgaatctg ccgattattc attactccgt ggagtggtgg    540
aacaccctgc atcagggatc aacgcggatg cagcaaagta tcgatccggc gatgcgttcg    600
ccgctgcgct ggtcgatttt tggcttcctg ctcctgtctg ccacgctgac gctgatgcgg    660
atgcgtaatt tgattttgct gatggaaaaa cgccgtccgt gggtgagtga actgatactg    720
aaaagaggcc gtaaatga                                                 738
```

```
<210> SEQ ID NO 61
<211> LENGTH: 37
<212> TYPE: DNA
<213> ORGANISM: Artificial Sequence
<220> FEATURE:
<223> OTHER INFORMATION: primer

<400> SEQUENCE: 61
gggaattcca tatgggtatg cttgaagcca gagagtt                            37

<210> SEQ ID NO 62
<211> LENGTH: 26
<212> TYPE: DNA
<213> ORGANISM: Artificial Sequence
<220> FEATURE:
<223> OTHER INFORMATION: primer

<400> SEQUENCE: 62
ccgctcgagt catgcggccc tcgttt                                        26

<210> SEQ ID NO 63
<211> LENGTH: 24
<212> TYPE: DNA
<213> ORGANISM: Artificial Sequence
<220> FEATURE:
<223> OTHER INFORMATION: primer

<400> SEQUENCE: 63
catgccatgg tgttctggcg catt                                          24

<210> SEQ ID NO 64
<211> LENGTH: 31
<212> TYPE: DNA
<213> ORGANISM: Artificial Sequence
<220> FEATURE:
<223> OTHER INFORMATION: primer

<400> SEQUENCE: 64
cgcggatcct tattgaatgc tgattcgtaa c                                  31

<210> SEQ ID NO 65
<211> LENGTH: 49
<212> TYPE: DNA
<213> ORGANISM: Artificial Sequence
<220> FEATURE:
```

<223> OTHER INFORMATION: primer

<400> SEQUENCE: 65
ccggaattca taaaaggagg aaaatatatg tggaaaacac tgcatcaac         49

<210> SEQ ID NO 66
<211> LENGTH: 31
<212> TYPE: DNA
<213> ORGANISM: Artificial Sequence
<220> FEATURE:
<223> OTHER INFORMATION: primer

<400> SEQUENCE: 66
acgcgtcgac tcatttacgg cctcttttca g                            31

<210> SEQ ID NO 67
<211> LENGTH: 76
<212> TYPE: DNA
<213> ORGANISM: Artificial Sequence
<220> FEATURE:
<223> OTHER INFORMATION: primer

<400> SEQUENCE: 67
tgagcggata acaatttcac acaggaaaca gaattcatgg tgagtaagaa ggtactcatc    60
gtagggatgt cgcaca                                                    76

<210> SEQ ID NO 68
<211> LENGTH: 70
<212> TYPE: DNA
<213> ORGANISM: Artificial Sequence
<220> FEATURE:
<223> OTHER INFORMATION: primer

<400> SEQUENCE: 68
gcggatcgag ccgtattgga cgatgtcatt gtttcctgtg tgaaattact ccctcgtttg    60
tgtggcagaa                                                           70

<210> SEQ ID NO 69
<211> LENGTH: 70
<212> TYPE: DNA
<213> ORGANISM: Artificial Sequence
<220> FEATURE:
<223> OTHER INFORMATION: primer

<400> SEQUENCE: 69
caccttctgc cacacaaacg agggagtaat tcacacagg aaacaatgac atcgtccaat     60
acggctcgat                                                           70

<210> SEQ ID NO 70
<211> LENGTH: 64
<212> TYPE: DNA
<213> ORGANISM: Artificial Sequence
<220> FEATURE:
<223> OTHER INFORMATION: primer

<400> SEQUENCE: 70
gccaagcttg gctgcaggtc gacggatccc cgggaattct catgatgcct tcgcttctgc    60
tgct                                                                 64

<210> SEQ ID NO 71
<211> LENGTH: 78
<212> TYPE: DNA
<213> ORGANISM: Artificial Sequence

```
<220> FEATURE:
<223> OTHER INFORMATION: primer

<400> SEQUENCE: 71
gcaccttggt tggtaggagt agcatgggat ccatgcatca ccatcaccat catagcactt     60
cttctgatta ctcccacg                                                  78

<210> SEQ ID NO 72
<211> LENGTH: 40
<212> TYPE: DNA
<213> ORGANISM: Artificial Sequence
<220> FEATURE:
<223> OTHER INFORMATION: primer

<400> SEQUENCE: 72
ttgtttcctg tgtgaaatta agcgtttcgc agtgcgcggg                           40

<210> SEQ ID NO 73
<211> LENGTH: 42
<212> TYPE: DNA
<213> ORGANISM: Artificial Sequence
<220> FEATURE:
<223> OTHER INFORMATION: primer

<400> SEQUENCE: 73
taatttcaca caggaaacaa tgaatgaacg cacatcggat gc                        42

<210> SEQ ID NO 74
<211> LENGTH: 52
<212> TYPE: DNA
<213> ORGANISM: Artificial Sequence
<220> FEATURE:
<223> OTHER INFORMATION: primer

<400> SEQUENCE: 74
aattataatg gccggctggg cctctagact agttggcagc tggcgccgct ga             52

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75
tctagaggcc cagccggcca ttataattag                                     30

<210> SEQ ID NO 76
<211> LENGTH: 30
<212> TYPE: DNA
<213> ORGANISM: Artificial Sequence
<220> FEATURE:
<223> OTHER INFORMATION: primer

<400> SEQUENCE: 76
ggatcccatg ctactcctac caaccaaggt                                     30
```